(12) United States Patent
Bullington et al.

(10) Patent No.: US 12,576,204 B2
(45) Date of Patent: Mar. 17, 2026

(54) SYSTEMS AND METHODS FOR DELIVERING A FLUID TO A PATIENT WITH REDUCED CONTAMINATION

(71) Applicant: Magnolia Medical Technologies, Inc., Seattle, WA (US)

(72) Inventors: Gregory J. Bullington, Seattle, WA (US); Richard G. Patton, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

(21) Appl. No.: 19/175,750

(22) Filed: Apr. 10, 2025

(65) Prior Publication Data

US 2025/0235613 A1    Jul. 24, 2025

Related U.S. Application Data

(60) Continuation of application No. 18/931,922, filed on Oct. 30, 2024, which is a continuation of application (Continued)

(51) Int. Cl.
*A61M 5/168* (2006.01)
*A61B 5/15* (2006.01)
(Continued)

(52) U.S. Cl.
CPC ..... *A61M 5/16827* (2013.01); *A61B 5/15003* (2013.01); *A61B 5/150213* (2013.01);
(Continued)

(58) Field of Classification Search
CPC ... A61B 5/1438; A61B 5/15003; A61B 5/154; A61B 5/150366; A61B 5/1427;
(Continued)

(56) References Cited

U.S. PATENT DOCUMENTS 2,674,265 A    4/1954    Lee
2,697,435 A    12/1954   Benjamin
(Continued)

FOREIGN PATENT DOCUMENTS

AT    310345 B    9/1973
AU    736156 B2   7/2001
(Continued)

OTHER PUBLICATIONS

Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.
(Continued)

*Primary Examiner* — Jason E Flick
(74) *Attorney, Agent, or Firm* — Cooley LLP

(57) ABSTRACT

An apparatus includes a cannula assembly, a housing, a fluid reservoir, a flow control mechanism, and an actuator. The housing includes an inlet port removably coupled to the cannula assembly and defines an inner volume. The fluid reservoir is fluidically coupled to the housing and configured to receive and isolate a volume of bodily fluid from a patient. The flow control mechanism is at least partially disposed in the inner volume. The actuator is operably coupled to the flow control mechanism and is configured to move the flow control mechanism between a first configuration, in which bodily fluid can flow, via a fluid flow path defined by the flow control mechanism, from the cannula assembly, through the inlet port and into the fluid reservoir, to a second configuration, in which the fluid reservoir is fluidically isolated from the cannula assembly.

30 Claims, 32 Drawing Sheets

Related U.S. Application Data

No. 18/399,007, filed on Dec. 28, 2023, now Pat. No. 12,133,968, which is a continuation of application No. 16/789,034, filed on Feb. 12, 2020, now Pat. No. 11,890,452, which is a continuation of application No. 16/255,055, filed on Jan. 23, 2019, now Pat. No. 10,596,315, which is a continuation of application No. 15/899,856, filed on Feb. 20, 2018, now Pat. No. 10,220,139, which is a continuation of application No. 14/838,794, filed on Aug. 28, 2015, now Pat. No. 9,931,466, which is a division of application No. 14/049,326, filed on Oct. 9, 2013, now Pat. No. 9,149,576.

(60) Provisional application No. 61/712,468, filed on Oct. 11, 2012.

(51) Int. Cl.
    *A61B 5/154*     (2006.01)
    *A61M 5/148*     (2006.01)

(52) U.S. Cl.
    CPC .. *A61B 5/150221* (2013.01); *A61B 5/150236* (2013.01); *A61B 5/150244* (2013.01); *A61B 5/150259* (2013.01); *A61B 5/150389* (2013.01); *A61B 5/150503* (2013.01); *A61B 5/150992* (2013.01); *A61B 5/154* (2013.01); *A61M 5/148* (2013.01)

(58) Field of Classification Search
    CPC ........ A61B 5/150755; A61B 5/150992; A61B 5/153; A61B 5/155; A61B 10/0045; A61B 5/1405; A61M 1/0209; A61M 1/02; A61M 1/0236; A61M 1/30; A61M 1/38; A61M 5/16827
    See application file for complete search history.

(56) References Cited

U.S. PATENT DOCUMENTS

| | | | |
|---|---|---|---|
| 2,707,953 A | 5/1955 | Ryan | |
| 2,847,995 A | 8/1958 | Adams | |
| 2,876,769 A | 3/1959 | Cordova | |
| 2,952,258 A | 9/1960 | Chandler | |
| 2,992,974 A | 7/1961 | Belcove et al. | |
| 3,013,557 A | 12/1961 | Pallotta | |
| 3,098,016 A | 7/1963 | Sam et al. | |
| 3,382,865 A | 5/1968 | Worrall, Jr. | |
| 3,405,706 A | 10/1968 | Paul | |
| 3,467,021 A | 9/1969 | Green, Jr. | |
| 3,467,095 A | 9/1969 | Ross | |
| 3,494,351 A | 2/1970 | Horn | |
| 3,494,352 A | 2/1970 | Russo et al. | |
| 3,577,980 A | 5/1971 | Cohen | |
| 3,596,652 A | 8/1971 | Winkelman | |
| 3,604,410 A | 9/1971 | Whitacre | |
| 3,635,798 A | 1/1972 | Kirkham et al. | |
| 3,640,267 A | 2/1972 | Hurtig et al. | |
| 3,648,684 A | 3/1972 | Barnwell et al. | |
| 3,650,093 A | 3/1972 | Rosenberg | |
| 3,680,558 A | 8/1972 | Kapelowitz | |
| 3,696,806 A | 10/1972 | Sausse | |
| 3,705,018 A | 12/1972 | Taylor | |
| 3,730,168 A | 5/1973 | McWhorter | |
| 3,741,197 A | 6/1973 | Sanz et al. | |
| 3,749,084 A | 7/1973 | Cucchiara | |
| 3,777,773 A | 12/1973 | Tolbert | |
| 3,779,383 A | 12/1973 | Ayres | |
| 3,803,810 A | 4/1974 | Rosenberg | |
| 3,817,240 A | 6/1974 | Ayres | |
| 3,831,602 A | 8/1974 | Broadwin | |
| 3,834,372 A | 9/1974 | Turney | |
| 3,835,835 A | 9/1974 | Thompson et al. | |
| 3,848,579 A | 11/1974 | Villa | |
| 3,848,581 A | 11/1974 | Cinqualbre et al. | |
| 3,859,998 A | 1/1975 | Thomas et al. | |
| 3,874,367 A | 4/1975 | Ayres | |
| 3,886,930 A | 6/1975 | Ryan | |
| 3,890,203 A | 6/1975 | Mehl | |
| 3,890,968 A | 6/1975 | Pierce et al. | |
| 3,937,211 A | 2/1976 | Merten | |
| 3,943,917 A | 3/1976 | Johansen | |
| 3,945,380 A | 3/1976 | Dabney et al. | |
| 3,960,139 A | 6/1976 | Bailey | |
| 3,978,846 A * | 9/1976 | Bailey | A61B 5/150389 604/125 |
| 3,996,923 A | 12/1976 | Guerra | |
| 4,056,101 A | 11/1977 | Geissler et al. | |
| 4,057,050 A | 11/1977 | Sarstedt | |
| 4,062,360 A | 12/1977 | Bentley | |
| 4,063,460 A | 12/1977 | Svensson | |
| 4,077,395 A | 3/1978 | Woolner | |
| 4,106,491 A | 8/1978 | Guerra | |
| 4,106,497 A | 8/1978 | Percarpio | |
| 4,133,304 A | 1/1979 | Bailey | |
| 4,133,863 A | 1/1979 | Koenig | |
| 4,150,089 A | 4/1979 | Linet | |
| 4,154,229 A | 5/1979 | Nugent | |
| 4,166,450 A | 9/1979 | Abramson | |
| 4,190,426 A | 2/1980 | Ruschke | |
| 4,193,400 A | 3/1980 | Loveless et al. | |
| 4,202,764 A | 5/1980 | Afflerbaugh et al. | |
| 4,206,282 A | 6/1980 | Hochstein | |
| 4,207,870 A * | 6/1980 | Eldridge | A61B 5/150732 604/167.03 |
| 4,210,173 A | 7/1980 | Choksi et al. | |
| 4,212,308 A | 7/1980 | Percarpio | |
| 4,226,236 A | 10/1980 | Genese | |
| 4,238,207 A | 12/1980 | Ruschke | |
| 4,257,416 A | 3/1981 | Prager | |
| 4,275,730 A | 6/1981 | Hussein | |
| 4,298,358 A | 11/1981 | Ruschke | |
| 4,312,362 A | 1/1982 | Kaufman | |
| 4,317,456 A | 3/1982 | Percarpio | |
| 4,327,746 A | 5/1982 | Feaster | |
| 4,340,067 A | 7/1982 | Rattenborg | |
| 4,340,068 A | 7/1982 | Kaufman | |
| 4,349,035 A | 9/1982 | Thomas et al. | |
| 4,354,507 A | 10/1982 | Raitto | |
| 4,370,987 A | 2/1983 | Bazell et al. | |
| 4,373,535 A | 2/1983 | Martell | |
| 4,398,544 A | 8/1983 | Nugent et al. | |
| 4,411,275 A | 10/1983 | Raitto | |
| 4,412,548 A | 11/1983 | Hoch | |
| 4,416,290 A | 11/1983 | Lutkowski | |
| 4,416,291 A | 11/1983 | Kaufman | |
| 4,425,235 A | 1/1984 | Cornell et al. | |
| 4,436,098 A | 3/1984 | Kaufman | |
| 4,444,203 A | 4/1984 | Engelman | |
| 4,459,997 A | 7/1984 | Sarstedt | |
| 4,496,458 A | 1/1985 | Lee | |
| 4,509,534 A | 4/1985 | Tassin, Jr. | |
| 4,551,131 A | 11/1985 | Miles et al. | |
| 4,581,014 A | 4/1986 | Millerd et al. | |
| 4,608,996 A | 9/1986 | Brown | |
| 4,626,248 A | 12/1986 | Scheller | |
| 4,654,027 A | 3/1987 | Dragan et al. | |
| 4,657,027 A | 4/1987 | Paulsen | |
| 4,657,160 A | 4/1987 | Woods et al. | |
| 4,673,386 A | 6/1987 | Gordon | |
| 4,676,256 A | 6/1987 | Golden | |
| 4,679,571 A | 7/1987 | Frankel et al. | |
| 4,690,154 A | 9/1987 | Woodford et al. | |
| 4,699,612 A | 10/1987 | Hamacher | |
| 4,703,763 A | 11/1987 | McAlister et al. | |
| 4,705,497 A | 11/1987 | Shitaokoshi et al. | |
| 4,714,461 A | 12/1987 | Gabel | |
| 4,715,854 A | 12/1987 | Vaillancourt | |
| 4,772,273 A | 9/1988 | Alchas | |
| 4,820,287 A | 4/1989 | Leonard | |
| 4,838,855 A | 6/1989 | Lynn | |

(56) References Cited

U.S. PATENT DOCUMENTS

| 4,865,583 | A | 9/1989 | Tu |
|---|---|---|---|
| 4,879,098 | A | 11/1989 | Oberhardt et al. |
| 4,886,072 | A | 12/1989 | Percarpio et al. |
| 4,890,627 | A | 1/1990 | Haber et al. |
| 4,904,240 | A | 2/1990 | Hoover |
| 4,936,315 | A | 6/1990 | Lineback |
| 4,980,297 | A | 12/1990 | Haynes et al. |
| 4,988,339 | A | 1/1991 | Vadher |
| 5,009,847 | A | 4/1991 | Solomons |
| 5,027,827 | A | 7/1991 | Cody et al. |
| 5,032,116 | A | 7/1991 | Peterson et al. |
| 5,032,288 | A | 7/1991 | Columbus et al. |
| 5,035,688 | A | 7/1991 | Inui |
| 5,045,185 | A | 9/1991 | Ohnaka et al. |
| 5,049,138 | A | 9/1991 | Chevalier et al. |
| 5,052,403 | A | 10/1991 | Haber et al. |
| 5,054,498 | A | 10/1991 | Melet |
| 5,066,284 | A | 11/1991 | Mersch et al. |
| 5,084,034 | A | 1/1992 | Zanotti |
| 5,097,842 | A | 3/1992 | Bonn |
| 5,100,394 | A | 3/1992 | Dudar et al. |
| 5,108,927 | A | 4/1992 | Dorn |
| 5,116,323 | A | 5/1992 | Kreuzer et al. |
| 5,122,129 | A | 6/1992 | Olson et al. |
| 5,126,054 | A | 6/1992 | Matkovich |
| 5,135,489 | A | 8/1992 | Jepson et al. |
| 5,147,329 | A | 9/1992 | Brannon |
| 5,208,160 | A | 5/1993 | Kikyotani et al. |
| 5,222,502 | A | 6/1993 | Kurose |
| 5,269,317 | A | 12/1993 | Bennett |
| 5,286,279 | A | 2/1994 | Wu |
| 5,330,464 | A | 7/1994 | Mathias et al. |
| 5,334,162 | A | 8/1994 | Harris |
| 5,354,537 | A | 10/1994 | Moreno |
| 5,360,011 | A | 11/1994 | McCallister |
| 5,372,143 | A | 12/1994 | Bernes et al. |
| 5,395,339 | A | 3/1995 | Talonn et al. |
| 5,417,673 | A | 5/1995 | Gordon |
| 5,429,610 | A | 7/1995 | Vaillancourt |
| 5,431,811 | A | 7/1995 | Tusini et al. |
| 5,439,022 | A | 8/1995 | Summers et al. |
| 5,439,450 | A | 8/1995 | Haedt |
| 5,450,856 | A | 9/1995 | Norris |
| 5,451,321 | A | 9/1995 | Matkovich |
| 5,454,786 | A | 10/1995 | Harris |
| 5,466,228 | A | 11/1995 | Evans |
| 5,472,605 | A | 12/1995 | Zuk, Jr. |
| 5,485,854 | A | 1/1996 | Hollister |
| 5,507,299 | A | 4/1996 | Roland |
| 5,520,193 | A | 5/1996 | Suzuki et al. |
| 5,522,804 | A | 6/1996 | Lynn |
| 5,573,510 | A | 11/1996 | Isaacson |
| 5,573,951 | A | 11/1996 | Gombrich et al. |
| 5,575,777 | A | 11/1996 | Cover et al. |
| 5,577,513 | A | 11/1996 | Van Vlasselaer |
| 5,603,700 | A | 2/1997 | Daneshvar |
| 5,632,906 | A | 5/1997 | Ishida et al. |
| 5,634,893 | A | 6/1997 | Rishton |
| 5,649,912 | A | 7/1997 | Peterson |
| 5,658,271 | A | 8/1997 | Loubser |
| 5,685,846 | A | 11/1997 | Michaels, Jr. |
| 5,691,486 | A | 11/1997 | Behringer et al. |
| 5,749,857 | A | 5/1998 | Cuppy |
| 5,759,160 | A | 6/1998 | Neese et al. |
| 5,762,633 | A | 6/1998 | Whisson |
| 5,772,608 | A | 6/1998 | Dhas |
| 5,785,682 | A | 7/1998 | Grabenkort |
| 5,811,658 | A | 9/1998 | Van Driel et al. |
| 5,824,001 | A | 10/1998 | Erskine |
| 5,857,983 | A | 1/1999 | Douglas et al. |
| 5,865,803 | A | 2/1999 | Major |
| 5,865,812 | A | 2/1999 | Correia |
| 5,871,699 | A | 2/1999 | Ruggeri |
| 5,873,841 | A | 2/1999 | Brannon |
| 5,876,926 | A | 3/1999 | Beecham |
| 5,882,318 | A | 3/1999 | Boyde |
| 5,911,705 | A | 6/1999 | Howell |
| 5,922,551 | A | 7/1999 | Durbin et al. |
| RE36,273 | E | 8/1999 | Brannon |
| 5,947,932 | A | 9/1999 | Desecki et al. |
| 5,961,472 | A | 10/1999 | Swendson et al. |
| 5,971,956 | A | 10/1999 | Epstein |
| 5,980,830 | A | 11/1999 | Savage et al. |
| 6,001,307 | A | 12/1999 | Naka et al. |
| 6,010,633 | A | 1/2000 | Zuk, Jr. et al. |
| 6,013,037 | A | 1/2000 | Brannon |
| 6,016,712 | A | 1/2000 | Warden et al. |
| 6,050,957 | A | 4/2000 | Desch |
| 6,103,271 | A | 8/2000 | Morrison et al. |
| 6,106,509 | A | 8/2000 | Loubser |
| 6,126,643 | A | 10/2000 | Vaillancouert |
| 6,159,164 | A | 12/2000 | Neese et al. |
| 6,171,493 | B1 | 1/2001 | Zia et al. |
| 6,190,855 | B1 | 2/2001 | Herman et al. |
| 6,210,909 | B1 | 4/2001 | Guirguis |
| 6,224,561 | B1 | 5/2001 | Swendson et al. |
| 6,254,581 | B1 | 7/2001 | Scott |
| 6,296,020 | B1 | 10/2001 | McNeely et al. |
| 6,299,131 | B1 | 10/2001 | Ryan |
| 6,306,614 | B1 | 10/2001 | Romaschin et al. |
| 6,325,975 | B1 | 12/2001 | Naka et al. |
| 6,328,726 | B1 | 12/2001 | Ishida et al. |
| 6,355,023 | B1 | 3/2002 | Roth et al. |
| 6,364,847 | B1 | 4/2002 | Shulze et al. |
| 6,364,890 | B1 | 4/2002 | Lum et al. |
| 6,368,306 | B1 | 4/2002 | Koska |
| 6,387,086 | B2 | 5/2002 | Mathias et al. |
| 6,398,743 | B1 | 6/2002 | Halseth et al. |
| 6,403,381 | B1 | 6/2002 | Mann et al. |
| 6,440,725 | B1 | 8/2002 | Pourahmadi et al. |
| 6,478,775 | B1 | 11/2002 | Galt et al. |
| 6,506,182 | B2 | 1/2003 | Estabrook et al. |
| 6,511,439 | B1 | 1/2003 | Tabata et al. |
| 6,520,948 | B1 | 2/2003 | Mathias et al. |
| 6,569,117 | B1 | 5/2003 | Ziv et al. |
| 6,592,555 | B1 | 7/2003 | Wen-Pi et al. |
| 6,592,613 | B1 | 7/2003 | Ishida et al. |
| 6,626,884 | B1 | 9/2003 | Dillon et al. |
| 6,629,959 | B2 | 10/2003 | Kuracina et al. |
| 6,638,252 | B2 | 10/2003 | Moulton et al. |
| 6,638,263 | B1 | 10/2003 | Theeuwes et al. |
| 6,648,835 | B1 | 11/2003 | Shemesh |
| 6,692,479 | B2 | 2/2004 | Kraus et al. |
| 6,695,004 | B1 | 2/2004 | Raybuck |
| 6,712,963 | B2 | 3/2004 | Schick |
| 6,716,187 | B1 | 4/2004 | Jorgensen et al. |
| 6,716,396 | B1 | 4/2004 | Anderson et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,772,513 | B1 | 8/2004 | Frye-Mason et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 6,979,323 | B2 | 12/2005 | Rogers et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,141,097 | B2 | 11/2006 | Leahey |
| 7,211,074 | B2 | 5/2007 | Sansoucy |
| 7,241,281 | B2 | 7/2007 | Coelho et al. |
| 7,264,608 | B2 | 9/2007 | Bischof et al. |
| 7,306,736 | B2 | 12/2007 | Collins et al. |
| 7,314,452 | B2 | 1/2008 | Madonia |
| 7,316,662 | B2 | 1/2008 | Delnevo et al. |
| 7,335,188 | B2 | 2/2008 | Graf |
| 7,351,228 | B2 | 4/2008 | Keane et al. |
| 7,384,416 | B2 | 6/2008 | Goudaliez et al. |
| 7,435,231 | B2 | 10/2008 | Mathias et al. |
| 7,461,671 | B2 | 12/2008 | Ehwald et al. |
| 7,479,131 | B2 | 1/2009 | Mathias et al. |

(56)             References Cited

U.S. PATENT DOCUMENTS

| | | |
|---|---|---|
| 7,544,324 B2 | 6/2009 | Tung et al. |
| 7,614,857 B2 | 11/2009 | Fuechslin et al. |
| 7,615,033 B2 | 11/2009 | Leong |
| 7,618,407 B2 | 11/2009 | Demay et al. |
| 7,648,491 B2 | 1/2010 | Rogers |
| 7,666,166 B1 | 2/2010 | Emmert et al. |
| 7,744,573 B2 | 6/2010 | Gordon et al. |
| 7,766,879 B2 | 8/2010 | Tan et al. |
| 7,896,817 B2 | 3/2011 | Garrison |
| 7,914,508 B2 | 3/2011 | Engstrom |
| 7,923,053 B2 | 4/2011 | Kitching et al. |
| 7,963,950 B2 | 6/2011 | Madonia |
| 8,070,725 B2 | 12/2011 | Christensen |
| 8,109,157 B2 | 2/2012 | Kanayama et al. |
| RE43,283 E | 3/2012 | Ishida et al. |
| 8,197,420 B2 | 6/2012 | Patton |
| 8,206,318 B2 | 6/2012 | Uchiyama et al. |
| 8,231,546 B2 | 7/2012 | Patton |
| 8,282,605 B2 | 10/2012 | Tan et al. |
| 8,287,499 B2 | 10/2012 | Miyasaka |
| 8,337,418 B2 | 12/2012 | Patton |
| 8,349,254 B2 | 1/2013 | Hoshino et al. |
| 8,356,644 B2 | 1/2013 | Chong et al. |
| 8,377,040 B2 | 2/2013 | Burkholz et al. |
| 8,382,712 B2 | 2/2013 | Kim |
| 8,383,044 B2 | 2/2013 | Davis et al. |
| 8,412,300 B2 | 4/2013 | Sonderegger |
| 8,523,826 B2 | 9/2013 | Layton, Jr. |
| 8,535,241 B2 | 9/2013 | Bullington et al. |
| 8,540,663 B2 | 9/2013 | Davey et al. |
| 8,568,371 B2 | 10/2013 | Siopes et al. |
| 8,574,203 B2 | 11/2013 | Stout et al. |
| 8,603,009 B2 | 12/2013 | Tan et al. |
| 8,647,286 B2 | 2/2014 | Patton |
| 8,679,063 B2 | 3/2014 | Stout et al. |
| 8,747,779 B2 | 6/2014 | Sprague et al. |
| 8,772,046 B2 | 7/2014 | Fraden et al. |
| 8,795,198 B2 | 8/2014 | Tan et al. |
| 8,808,202 B2 | 8/2014 | Brancazio |
| 8,827,958 B2 | 9/2014 | Bierman et al. |
| 8,864,684 B2 | 10/2014 | Bullington et al. |
| 8,876,734 B2 | 11/2014 | Patton |
| 8,992,505 B2 | 3/2015 | Thorne, Jr. et al. |
| 9,022,950 B2 | 5/2015 | Bullington et al. |
| 9,022,951 B2 | 5/2015 | Bullington et al. |
| 9,060,724 B2 | 6/2015 | Bullington et al. |
| 9,060,725 B2 | 6/2015 | Bullington et al. |
| 9,138,572 B2 | 9/2015 | Zeytoonian et al. |
| 9,149,576 B2 | 10/2015 | Bullington et al. |
| 9,155,495 B2 | 10/2015 | Bullington et al. |
| 9,204,864 B2 | 12/2015 | Bullington et al. |
| 9,205,198 B2 | 12/2015 | Py |
| 9,233,208 B2 | 1/2016 | Tekeste |
| RE45,896 E | 2/2016 | Stout et al. |
| 9,314,201 B2 | 4/2016 | Burkholz et al. |
| 9,320,459 B2 | 4/2016 | Chin et al. |
| 9,855,001 B2 | 1/2018 | Patton |
| 9,855,002 B2 | 1/2018 | Patton |
| 9,855,386 B2 | 1/2018 | Close et al. |
| 9,861,306 B2 | 1/2018 | Patton |
| 9,872,645 B2 | 1/2018 | Patton |
| 9,877,674 B2 | 1/2018 | Holmes et al. |
| 9,877,675 B2 | 1/2018 | Baid |
| 9,895,092 B2 | 2/2018 | Burkholz |
| 9,931,466 B2 | 4/2018 | Bullington et al. |
| 9,950,084 B2 | 4/2018 | Bullington et al. |
| 9,999,383 B2 | 6/2018 | Bullington et al. |
| 10,022,530 B2 | 7/2018 | Tekeste |
| 10,028,687 B2 | 7/2018 | Patton |
| 10,028,688 B2 | 7/2018 | Patton |
| 10,028,689 B2 | 7/2018 | Patton |
| 10,039,483 B2 | 8/2018 | Bullington et al. |
| 10,045,724 B2 | 8/2018 | Patton |
| 10,052,053 B2 | 8/2018 | Patton |
| 10,080,516 B2 | 9/2018 | Ellis et al. |
| 10,086,142 B2 | 10/2018 | Tekeste |
| 10,206,613 B2 | 2/2019 | Bullington et al. |
| 10,220,139 B2 | 3/2019 | Bullington et al. |
| 10,251,590 B2 | 4/2019 | Bullington et al. |
| 10,265,007 B2 | 4/2019 | Bullington et al. |
| 10,292,633 B2 | 5/2019 | Bullington et al. |
| 10,299,713 B2 | 5/2019 | Patton |
| 10,433,779 B2 | 10/2019 | Bullington et al. |
| 10,596,315 B2 | 3/2020 | Bullington et al. |
| 10,624,977 B2 | 4/2020 | Bullington et al. |
| 10,736,554 B2 | 8/2020 | Bullington et al. |
| 10,772,548 B2 | 9/2020 | Bullington et al. |
| 10,813,579 B2 | 10/2020 | Baid |
| 10,827,964 B2 | 11/2020 | Rogers et al. |
| 10,856,791 B2 | 12/2020 | McHale et al. |
| 10,881,343 B2 | 1/2021 | Bullington et al. |
| 10,888,262 B2 | 1/2021 | Russ et al. |
| 10,912,506 B2 | 2/2021 | Bullington et al. |
| 11,076,787 B2 | 8/2021 | Bullington et al. |
| 11,234,626 B2 | 2/2022 | Bullington et al. |
| 11,259,727 B2 | 3/2022 | Bullington et al. |
| 11,311,218 B2 | 4/2022 | Bullington et al. |
| 11,317,838 B2 | 5/2022 | Bullington et al. |
| 11,318,459 B2 | 5/2022 | Shi et al. |
| 11,395,611 B2 | 7/2022 | Bullington et al. |
| 11,395,612 B2 | 7/2022 | Bullington et al. |
| 11,419,531 B2 | 8/2022 | Bullington et al. |
| 11,529,081 B2 | 12/2022 | Bullington et al. |
| 11,589,786 B2 | 2/2023 | Bullington et al. |
| 11,607,159 B2 | 3/2023 | Bullington et al. |
| 11,653,863 B2 | 5/2023 | Bullington et al. |
| 11,660,030 B2 | 5/2023 | Bullington et al. |
| 11,737,693 B2 | 8/2023 | Bullington et al. |
| 11,786,155 B2 | 10/2023 | Bullington et al. |
| 11,789,017 B2 | 10/2023 | Bullington et al. |
| 11,819,329 B2 | 11/2023 | Bullington et al. |
| 11,857,321 B2 | 1/2024 | Bullington et al. |
| 11,890,452 B2 | 2/2024 | Bullington et al. |
| 11,903,709 B2 | 2/2024 | Bullington et al. |
| 11,903,710 B2 | 2/2024 | Bullington et al. |
| 11,998,332 B2 | 6/2024 | Bullington et al. |
| 12,083,234 B2 | 9/2024 | Bullington et al. |
| 12,133,968 B2 | 11/2024 | Bullington et al. |
| 12,150,763 B2 | 11/2024 | Bullington et al. |
| 12,186,080 B2 | 1/2025 | Bullington et al. |
| 12,193,816 B2 | 1/2025 | Bullington et al. |
| 12,471,815 B2 | 11/2025 | Bullington et al. |
| 12,471,816 B2 | 11/2025 | Bullington et al. |
| 2001/0031932 A1 | 10/2001 | Blake et al. |
| 2001/0039058 A1 | 11/2001 | Iheme et al. |
| 2002/0002349 A1 | 1/2002 | Flaherty et al. |
| 2002/0004647 A1 | 1/2002 | Leong |
| 2002/0107469 A1 | 8/2002 | Bolan et al. |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0055381 A1 | 3/2003 | Wilkinson |
| 2003/0069543 A1 | 4/2003 | Carpenter et al. |
| 2003/0105414 A1 | 6/2003 | Leong |
| 2003/0208151 A1* | 11/2003 | Kraus ............... A61B 5/15003 |
| | | 604/4.01 |
| 2004/0000309 A1 | 1/2004 | Alston |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0073171 A1 | 4/2004 | Rogers et al. |
| 2004/0124389 A1 | 7/2004 | Phillips |
| 2004/0127816 A1 | 7/2004 | Galvao |
| 2004/0147855 A1 | 7/2004 | Marsden |
| 2005/0004524 A1 | 1/2005 | Newby et al. |
| 2005/0010136 A1 | 1/2005 | Restelli et al. |
| 2005/0054949 A1 | 3/2005 | McKinnon et al. |
| 2005/0082218 A1 | 4/2005 | Verri et al. |
| 2005/0131344 A1 | 6/2005 | Godaire |
| 2005/0148993 A1 | 7/2005 | Mathias et al. |
| 2005/0154368 A1 | 7/2005 | Lim et al. |
| 2005/0161112 A1 | 7/2005 | Ehwald et al. |
| 2005/0199077 A1 | 9/2005 | Prybella et al. |

(56) References Cited

U.S. PATENT DOCUMENTS

| | | |
|---|---|---|
| 2005/0240161 A1 | 10/2005 | Crawford |
| 2005/0245885 A1 | 11/2005 | Brown |
| 2005/0273019 A1 | 12/2005 | Conway et al. |
| 2005/0277848 A1 | 12/2005 | Graf |
| 2005/0281713 A1 | 12/2005 | Hampsch et al. |
| 2005/0283125 A1 | 12/2005 | Barkhahn et al. |
| 2006/0009713 A1 | 1/2006 | Flaherty |
| 2006/0018790 A1 | 1/2006 | Naka et al. |
| 2006/0111667 A1 | 5/2006 | Matsuura et al. |
| 2006/0155212 A1 | 7/2006 | Madonia |
| 2006/0251622 A1 | 11/2006 | Suzuki et al. |
| 2006/0287639 A1 | 12/2006 | Sharp |
| 2007/0083162 A1 | 4/2007 | O'Reagan et al. |
| 2007/0088279 A1 | 4/2007 | Shue et al. |
| 2007/0100250 A1 | 5/2007 | Kline |
| 2007/0119508 A1 | 5/2007 | West et al. |
| 2007/0172389 A1 | 7/2007 | Wilding et al. |
| 2007/0191716 A1 | 8/2007 | Goldberger et al. |
| 2007/0232956 A1 | 10/2007 | Harman et al. |
| 2007/0287948 A1 | 12/2007 | Sakiewicz |
| 2008/0086085 A1 | 4/2008 | Brown |
| 2008/0108954 A1 | 5/2008 | Mathias et al. |
| 2008/0114304 A1 | 5/2008 | Nalesso et al. |
| 2008/0145933 A1 | 6/2008 | Patton |
| 2008/0167577 A1 | 7/2008 | Weilbacher et al. |
| 2008/0185056 A1 | 8/2008 | Diodati et al. |
| 2008/0200837 A1 | 8/2008 | Frazier et al. |
| 2008/0254471 A1 | 10/2008 | Bordano |
| 2008/0255523 A1 | 10/2008 | Grinberg |
| 2008/0312576 A1 | 12/2008 | McKinnon et al. |
| 2008/0319346 A1 | 12/2008 | Crawford et al. |
| 2009/0076441 A1 | 3/2009 | Sebban |
| 2009/0173685 A1 | 7/2009 | Imai et al. |
| 2009/0177117 A1 | 7/2009 | Amano et al. |
| 2009/0192447 A1 | 7/2009 | Andersen et al. |
| 2009/0215159 A1 | 8/2009 | Kirby |
| 2009/0227896 A1 | 9/2009 | Alvin Tan et al. |
| 2009/0259201 A1 | 10/2009 | Hwang et al. |
| 2009/0301317 A1 | 12/2009 | Andrews |
| 2009/0306601 A1 | 12/2009 | Shaw et al. |
| 2010/0010372 A1 | 1/2010 | Brown et al. |
| 2010/0042048 A1 | 2/2010 | Christensen |
| 2010/0057004 A1 | 3/2010 | Christensen et al. |
| 2010/0094171 A1 | 4/2010 | Conway et al. |
| 2010/0152681 A1 | 6/2010 | Mathias |
| 2010/0185134 A1 | 7/2010 | Houwen et al. |
| 2010/0234768 A1 | 9/2010 | Uchiyama et al. |
| 2010/0240964 A1 | 9/2010 | Sterling et al. |
| 2010/0252118 A1 | 10/2010 | Fraden et al. |
| 2010/0255589 A1 | 10/2010 | Saiki et al. |
| 2010/0268118 A1 | 10/2010 | Schweiger |
| 2010/0286513 A1 | 11/2010 | Pollard, Jr. et al. |
| 2010/0298671 A1 | 11/2010 | Asakura et al. |
| 2011/0009717 A1 | 1/2011 | Davis et al. |
| 2011/0046602 A1 | 2/2011 | Grimm et al. |
| 2011/0092856 A1 | 4/2011 | Freeman et al. |
| 2011/0125058 A1 | 5/2011 | Levinson et al. |
| 2011/0178427 A1 | 7/2011 | Tan et al. |
| 2011/0198221 A1 | 8/2011 | Angelescu |
| 2011/0288441 A1 | 11/2011 | Taguchi |
| 2011/0306856 A1 | 12/2011 | Rule et al. |
| 2011/0306899 A1 | 12/2011 | Brown et al. |
| 2011/0313318 A1 | 12/2011 | Rule et al. |
| 2011/0319859 A1 | 12/2011 | Zeytoonian et al. |
| 2012/0004619 A1 | 1/2012 | Stephens et al. |
| 2012/0016266 A1 | 1/2012 | Burkholz |
| 2012/0017999 A1 | 1/2012 | Velschow |
| 2012/0022404 A1 | 1/2012 | Fojtik |
| 2012/0029494 A1 | 2/2012 | Wittenberger et al. |
| 2012/0035540 A1 | 2/2012 | Ferren et al. |
| 2012/0095367 A1 | 4/2012 | Patton |
| 2012/0123297 A1 | 5/2012 | Brancazio |
| 2012/0215131 A1 | 8/2012 | Patton |
| 2012/0226239 A1 | 9/2012 | Green |
| 2012/0245042 A1 | 9/2012 | Liu et al. |
| 2012/0265099 A1 | 10/2012 | Goodnow, II et al. |
| 2012/0265128 A1 | 10/2012 | Kolln |
| 2012/0277697 A1 | 11/2012 | Haghgooie et al. |
| 2012/0323142 A1 | 12/2012 | Allen et al. |
| 2013/0023792 A1 | 1/2013 | Markey et al. |
| 2013/0085514 A1 | 4/2013 | Lee et al. |
| 2013/0116599 A1 | 5/2013 | Bullington et al. |
| 2013/0158506 A1 | 6/2013 | Harris et al. |
| 2013/0289420 A1 | 10/2013 | Pfeiffer et al. |
| 2013/0295602 A1 | 11/2013 | Fowler et al. |
| 2013/0317391 A1 | 11/2013 | Bullington et al. |
| 2014/0008366 A1 | 1/2014 | Genosar |
| 2014/0051062 A1 | 2/2014 | Vanapalli et al. |
| 2014/0066880 A1 | 3/2014 | Prince et al. |
| 2014/0081172 A1 | 3/2014 | Patton |
| 2014/0107564 A1 | 4/2014 | Bullington et al. |
| 2014/0124542 A1 | 5/2014 | Kojima et al. |
| 2014/0128775 A1 | 5/2014 | Andreae et al. |
| 2014/0155781 A1 | 6/2014 | Bullington et al. |
| 2014/0155782 A1 | 6/2014 | Bullington et al. |
| 2014/0163419 A1 | 6/2014 | Bullington et al. |
| 2014/0188002 A1 | 7/2014 | Close et al. |
| 2014/0208978 A1 | 7/2014 | Sunder et al. |
| 2014/0221873 A1 | 8/2014 | Hayakawa et al. |
| 2014/0257249 A1 | 9/2014 | Witt |
| 2014/0276039 A1 | 9/2014 | Cowan et al. |
| 2014/0305196 A1 | 10/2014 | Ellis et al. |
| 2014/0336536 A1 | 11/2014 | Brancazio |
| 2015/0011847 A1 | 1/2015 | Hayden |
| 2015/0011910 A1 | 1/2015 | Bullington et al. |
| 2015/0018715 A1 | 1/2015 | Walterspiel |
| 2015/0025454 A1 | 1/2015 | Wetzel et al. |
| 2015/0025455 A1 | 1/2015 | Shetty et al. |
| 2015/0025456 A1 | 1/2015 | Shetty et al. |
| 2015/0073304 A1 | 3/2015 | Millerd |
| 2015/0094615 A1 | 4/2015 | Patton |
| 2015/0151298 A1 | 6/2015 | Hobbs et al. |
| 2015/0257691 A1 | 9/2015 | Bullington et al. |
| 2015/0314105 A1 | 11/2015 | Gasparyan et al. |
| 2015/0342510 A1 | 12/2015 | Bullington et al. |
| 2015/0351678 A1 | 12/2015 | Bullington et al. |
| 2016/0008579 A1 | 1/2016 | Burkholz et al. |
| 2016/0038068 A1 | 2/2016 | Chickering, III et al. |
| 2016/0038684 A1 | 2/2016 | Lum et al. |
| 2016/0081606 A1 | 3/2016 | Russ et al. |
| 2016/0089070 A1 | 3/2016 | Russ et al. |
| 2016/0174888 A1 | 6/2016 | Berthier et al. |
| 2016/0174948 A1 | 6/2016 | Kato et al. |
| 2016/0213294 A1 | 7/2016 | Patton |
| 2016/0257586 A1 | 9/2016 | Shaamsundarr |
| 2016/0361006 A1 | 12/2016 | Bullington et al. |
| 2016/0367177 A1 | 12/2016 | Edelhauser et al. |
| 2017/0059552 A1 | 3/2017 | Campton et al. |
| 2017/0071519 A1 | 3/2017 | Gelfand et al. |
| 2017/0153165 A1 | 6/2017 | Nwadigo |
| 2017/0227536 A1 | 8/2017 | Matsuura |
| 2017/0276679 A1 | 9/2017 | Chapman et al. |
| 2017/0327867 A1 | 11/2017 | Dohale et al. |
| 2018/0092584 A1 | 4/2018 | Bullington et al. |
| 2018/0160958 A1 | 6/2018 | Baid |
| 2018/0242890 A1 | 8/2018 | Chickering, III et al. |
| 2018/0321270 A1 | 11/2018 | Iwashita et al. |
| 2018/0353117 A1 | 12/2018 | Bullington et al. |
| 2019/0000367 A1 | 1/2019 | Lundquist et al. |
| 2019/0049442 A1 | 2/2019 | Guirguis |
| 2019/0076074 A1 | 3/2019 | Bullington et al. |
| 2019/0150818 A1 | 5/2019 | Bullington et al. |
| 2019/0175087 A1 | 6/2019 | Bullington et al. |
| 2019/0209066 A1 | 7/2019 | Bullington et al. |
| 2019/0365303 A1 | 12/2019 | Bullington et al. |
| 2020/0060595 A1 | 2/2020 | Bullington et al. |
| 2020/0060596 A1 | 2/2020 | Patton |
| 2021/0186392 A1 | 6/2021 | Bullington et al. |
| 2021/0290123 A1 | 9/2021 | Sawyer |
| 2021/0353193 A1 | 11/2021 | Bullington et al. |
| 2021/0361207 A1 | 11/2021 | Rogers et al. |
| 2022/0151525 A1 | 5/2022 | Bullington et al. |
| 2022/0151526 A1 | 5/2022 | Bullington et al. |
| 2022/0151527 A1 | 5/2022 | Bullington et al. |

(56) References Cited

U.S. PATENT DOCUMENTS

| | | | |
|---|---|---|---|
| 2022/0175284 A1 | 6/2022 | Bullington et al. |
| 2022/0183600 A1 | 6/2022 | Bullington et al. |
| 2022/0304600 A1 | 9/2022 | Hammer |
| 2022/0304601 A1 | 9/2022 | Bullington et al. |
| 2022/0304664 A1 | 9/2022 | Hammer |
| 2022/0361786 A1 | 11/2022 | Bullington et al. |
| 2022/0369971 A1 | 11/2022 | Bullington et al. |
| 2023/0172502 A1 | 6/2023 | Bullington et al. |
| 2023/0190157 A1 | 6/2023 | Bullington et al. |
| 2023/0363674 A1 | 11/2023 | Bullington et al. |
| 2023/0417746 A1 | 12/2023 | Bullington et al. |
| 2024/0041370 A1 | 2/2024 | Bullington et al. |
| 2024/0057908 A1 | 2/2024 | Bullington et al. |
| 2024/0065590 A1 | 2/2024 | Bullington et al. |
| 2024/0138734 A1 | 5/2024 | Bullington et al. |
| 2024/0164670 A1 | 5/2024 | Patton |
| 2024/0315620 A1 | 9/2024 | Bullington et al. |
| 2024/0315621 A1 | 9/2024 | Bullington et al. |
| 2024/0315622 A1 | 9/2024 | Bullington et al. |
| 2024/0315623 A1 | 9/2024 | Bullington et al. |
| 2024/0315624 A1 | 9/2024 | Bullington et al. |
| 2025/0082235 A1 | 3/2025 | Bullington et al. |
| 2025/0120628 A1 | 4/2025 | Bullington et al. |
| 2025/0235133 A1 | 7/2025 | Bullington et al. |
| 2025/0275697 A1 | 9/2025 | Bullington et al. |

FOREIGN PATENT DOCUMENTS

| | | | |
|---|---|---|---|
| BR | 112012025546 A2 | 6/2016 |
| CA | 1264275 A | 1/1990 |
| CN | 86103696 A | 1/1987 |
| CN | 2115767 U | 9/1992 |
| CN | 1713928 A | 12/2005 |
| CN | 1784186 A | 6/2006 |
| CN | 1901955 A | 1/2007 |
| CN | 2907683 Y | 6/2007 |
| CN | 1325126 C | 7/2007 |
| CN | 101060871 A | 10/2007 |
| CN | 101309641 A | 11/2008 |
| CN | 101352357 A | 1/2009 |
| CN | 101437450 A | 5/2009 |
| CN | 101564301 A | 10/2009 |
| CN | 101631498 A | 1/2010 |
| CN | 101676001 A | 3/2010 |
| CN | 101785676 A | 7/2010 |
| CN | 101801445 A | 8/2010 |
| CN | 201617841 U | 11/2010 |
| CN | 102421362 A | 4/2012 |
| CN | 102548524 A | 7/2012 |
| CN | 102811754 A | 12/2012 |
| CN | 102971040 A | 3/2013 |
| CN | 103027727 A | 4/2013 |
| CN | 101626803 B | 8/2013 |
| CN | 103477201 A | 12/2013 |
| CN | 103619386 A | 3/2014 |
| CN | 104902817 A | 9/2015 |
| CN | 104955392 A | 9/2015 |
| CN | 104971390 A | 10/2015 |
| CN | 104981203 A | 10/2015 |
| CN | 105090005 A | 11/2015 |
| CN | 105612346 A | 5/2016 |
| CN | 105813669 A | 7/2016 |
| CN | 107736901 A | 2/2018 |
| CN | 107874786 A | 4/2018 |
| CN | 209916854 U | 1/2020 |
| CN | 111132602 A | 5/2020 |
| CN | 111771054 A | 10/2020 |
| DE | 7203008 U | 5/1972 |
| DE | 2203858 A1 | 5/1973 |
| DE | 2541494 A1 | 3/1977 |
| DE | 2203858 B2 | 10/1977 |
| DE | 2946660 A1 | 5/1981 |
| DE | 3403957 A1 | 8/1985 |
| DE | 4026732 A1 | 2/1992 |
| DE | 29913417 U1 | 12/2000 |

| | | | |
|---|---|---|---|
| DE | 10038026 A1 | 2/2001 |
| DE | 10134913 A1 | 2/2003 |
| DE | 10134913 C2 | 6/2003 |
| DE | 10243129 A1 | 4/2004 |
| DE | 69632870 T2 | 7/2005 |
| DE | 102009057792 B4 | 8/2016 |
| EP | 0181957 A1 | 5/1986 |
| EP | 0207304 A1 | 1/1987 |
| EP | 0448795 A2 | 10/1991 |
| EP | 0208053 B1 | 12/1991 |
| EP | 0329786 B1 | 1/1993 |
| EP | 0486059 B1 | 1/1997 |
| EP | 1144026 B1 | 7/2004 |
| EP | 1505159 B1 | 5/2008 |
| EP | 1980204 A1 | 10/2008 |
| EP | 2254472 A2 | 12/2010 |
| EP | 1381438 B1 | 5/2012 |
| EP | 2254472 B1 | 5/2016 |
| EP | 2854643 B1 | 11/2016 |
| EP | 1487369 B1 | 5/2017 |
| EP | 2986218 B1 | 12/2017 |
| EP | 3634212 A4 | 3/2021 |
| EP | 2178585 B1 | 4/2021 |
| EP | 3938108 B1 | 8/2023 |
| ES | 2564496 T3 | 3/2016 |
| FR | 2110516 A5 | 6/1972 |
| FR | 2691364 B1 | 8/1999 |
| FR | 2833175 B1 | 5/2004 |
| FR | 2851167 B1 | 10/2005 |
| GB | 1506449 A | 4/1978 |
| GB | 1562686 A | 3/1980 |
| IE | 904353 A1 | 10/1991 |
| IL | 128709 A | 9/2004 |
| JP | S4846180 A | 7/1973 |
| JP | S5397289 A | 8/1978 |
| JP | S56109643 A | 8/1981 |
| JP | S5789869 A | 6/1982 |
| JP | S6458241 A | 3/1989 |
| JP | H0363570 A | 3/1991 |
| JP | H05501071 A | 3/1993 |
| JP | H0551222 B2 | 8/1993 |
| JP | H06500403 A | 1/1994 |
| JP | H0716219 A | 1/1995 |
| JP | H0910302 A | 1/1997 |
| JP | H0951947 A | 2/1997 |
| JP | H09229828 A | 9/1997 |
| JP | H10153531 A | 6/1998 |
| JP | H10211274 A | 8/1998 |
| JP | H1156821 A | 3/1999 |
| JP | H1176397 A | 3/1999 |
| JP | H11197236 A | 7/1999 |
| JP | 2001159630 A | 6/2001 |
| JP | 2001161668 A | 6/2001 |
| JP | 2001276181 A | 10/2001 |
| JP | 3231086 B2 | 11/2001 |
| JP | 2002116201 A | 4/2002 |
| JP | 2002272710 A | 9/2002 |
| JP | 2002528159 A | 9/2002 |
| JP | 2003126068 A | 5/2003 |
| JP | 2005237617 A | 9/2005 |
| JP | 2006026327 A | 2/2006 |
| JP | 3813974 B2 | 8/2006 |
| JP | 2007175534 A | 7/2007 |
| JP | 2008149076 A | 7/2008 |
| JP | 2008206734 A | 9/2008 |
| JP | 2009525819 A | 7/2009 |
| JP | 2009536554 A | 10/2009 |
| JP | 4382322 B2 | 12/2009 |
| JP | 2010514501 A | 5/2010 |
| JP | 2010524505 A | 7/2010 |
| JP | 2010189415 A | 9/2010 |
| JP | 4573538 B2 | 11/2010 |
| JP | 2010536014 A | 11/2010 |
| JP | 2011512987 A | 4/2011 |
| JP | 4861649 B2 | 1/2012 |
| JP | 4869910 B2 | 2/2012 |
| JP | 5344252 B2 | 11/2013 |
| JP | 5620541 B2 | 11/2014 |
| JP | 2015014552 A | 1/2015 |

(56) References Cited

FOREIGN PATENT DOCUMENTS

| | | | |
|---|---|---|---|
| JP | 2015519145 | A | 7/2015 |
| JP | 2015215355 | A | 12/2015 |
| JP | 2016500278 | A | 1/2016 |
| JP | 2016504075 | A | 2/2016 |
| JP | 2016520827 | A | 7/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 6242386 | B2 | 12/2017 |
| JP | 2018034009 | A | 3/2018 |
| JP | 2018110967 | A | 7/2018 |
| JP | 2018525191 | A | 9/2018 |
| JP | 2020513906 | A | 5/2020 |
| JP | 2020121167 | A | 8/2020 |
| JP | 7204742 | B2 | 1/2023 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO-1986005568 | A1 | 9/1986 |
| WO | WO-1990004351 | A1 | 5/1990 |
| WO | WO-8403213 | A1 | 10/1990 |
| WO | WO-1991018632 | A1 | 12/1991 |
| WO | WO-1992016144 | A1 | 10/1992 |
| WO | WO-1994007415 | A1 | 4/1994 |
| WO | WO-1994012093 | A1 | 6/1994 |
| WO | WO-1994015665 | A1 | 7/1994 |
| WO | WO-1995011712 | A1 | 5/1995 |
| WO | WO-1995016395 | A1 | 6/1995 |
| WO | WO-1995021639 | A1 | 8/1995 |
| WO | WO-1995024176 | A1 | 9/1995 |
| WO | WO-1996021853 | A1 | 7/1996 |
| WO | WO-1997018845 | A1 | 5/1997 |
| WO | WO-1997045714 | A1 | 12/1997 |
| WO | WO-1998034532 | A1 | 8/1998 |
| WO | WO-1998046136 | A1 | 10/1998 |
| WO | WO-1999013925 | A1 | 3/1999 |
| WO | WO-9929232 | A1 | 6/1999 |
| WO | WO-1999048425 | A1 | 9/1999 |
| WO | WO-1999055232 | A1 | 11/1999 |
| WO | WO-2000024313 | A1 | 5/2000 |
| WO | WO-2000040291 | A1 | 7/2000 |
| WO | WO-2000041624 | A1 | 7/2000 |
| WO | WO-2001008546 | A2 | 2/2001 |
| WO | WO-2001091829 | A2 | 12/2001 |
| WO | WO-2002028457 | A1 | 4/2002 |
| WO | WO-2002045813 | A1 | 6/2002 |
| WO | WO-2002051520 | A1 | 7/2002 |
| WO | WO-2003008012 | A2 | 1/2003 |
| WO | WO-2003041767 | A1 | 5/2003 |
| WO | WO-2003047660 | A1 | 6/2003 |
| WO | WO-2003078964 | A2 | 9/2003 |
| WO | WO-2003085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO-2005068011 | A1 | 7/2005 |
| WO | WO-2006031500 | A2 | 3/2006 |
| WO | WO-2006124634 | A1 | 11/2006 |
| WO | WO-2007033319 | A1 | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO-2008101025 | A1 | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A2 | 8/2010 |
| WO | WO-2011030282 | A1 | 3/2011 |
| WO | WO-2011050110 | A1 | 4/2011 |
| WO | WO-2011069145 | A2 | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO-2012012127 | A2 | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015091818 | A1 | 6/2015 |
| WO | WO-2016027782 | A1 | 2/2016 |
| WO | WO-2016201406 | A1 | 12/2016 |
| WO | WO-2017041087 | A1 | 3/2017 |
| WO | WO-2018227191 | A1 | 12/2018 |
| WO | WO-2019055487 | A1 | 3/2019 |
| WO | WO-2019113505 | A1 | 6/2019 |
| WO | WO-2019232196 | A1 | 12/2019 |
| WO | WO-2020163744 | A1 | 8/2020 |
| WO | WO-2020185914 | A1 | 9/2020 |
| WO | WO-2021119487 | A1 | 6/2021 |
| WO | WO-2022203747 | A1 | 9/2022 |

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.

Barnard, D. R. & Arthur, M. M., "Fibronectin (cold insoluble globulin) in the neonate," Clinical and Laboratory Observations, 102(3): 453-455 (1983).

Bauman et al., "Don't Stick Me Again! Reducing Blood Culture Contamination," INOVA Fairfax Medical Campus, Emergency Department (2019), 1 page.

Baxter, "IV Tubing and Access Devices" authored by and published by Baxter, dated Nov. 6, 2006, 105 pages.

BD Medical Surgical Systems Catalogue (Canadian Version), BD Medical, 2010, 51 pages.

BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.

BD Vacutainer Passive Shielding Blood Collection Needle Brochure; Becton Dickinson and Company (2005), 2 pages.

Bell et al., Effectiveness of a Novel Specimen Collection System in Reducing Blood Culture Contamination Rates, J. Emergency Nursing, vol. 44, No. 6, 570 (Nov. 2018), 6 pages.

Blakeney, "Reduction of Blood Culture Contaminations Using Initial Specimen Diversion Device," Beebe Healthcare (Jun. 2018), 1 page.

Brecher, M. E. et al., "Bacterial Contamination of Blood Components," Clinical Microbiology Reviews, 18(1):195-204 (2005).

Brownfield et al., "Emergency Department Observes 83% Reduction in Blood Culture Contamination with Initial Specimen Diversion Technology Adoption," Am. J. Infection Control, vol. 49, S14, ADS 34 (Jun. 2021), 1 page.

Bruneau, Cecile, et al.; "Efficacy of a new collection procedure for preventing bacterial contamination of whole-blood donations," Transfusion (2001); 41(1):74-81.

Calam, R. R., "Recommended 'Order of Draw' for Collecting Blood Specimens Into Additive-Containing Tubes," Letter to the Editor, Clinical Chemistry, 28(6):1399 (1982), 1 page.

Cartridge and Test Information, Abbott, Art: 714258-010 Rev. Date: Aug. 15, 2016, 6 pages.

Challiner, A. et al., Queen Alexandra Hospital, Portsmouth P06 3LY, "Venous/arterial blood management protection system," Anaesthesia, Correspondence (Feb. 1992); 47(2), p. 169.

Chamarthy, P., et al.; "Mixing Characteristics in a Serpentine Micro-Channel," IMECE2004-61902; Proceedings of the ASME 2004 International Mechanical Engineering Congress and Exposi-

(56)          References Cited

OTHER PUBLICATIONS tion. Fluids Engineering. Anaheim, California, USA; Nov. 13-19, 2004, pp. 253-261; Exhibit 4; 10 pages.

Chang et al., "Impact of Blood Culture Diversion Device and Molecular Pathogen Identification on Vancomycin Use," San Antonio Military Medical Center (2016), 1 page.

Claim Construction Order, Document 75, *Magnolia Medical Technologies, Inc.* v. *Kurin, Inc.,* C.A. 19-00097-CFC-CJB (D. Del.), filed May 20, 2020, 4 pages.

Claim Construction Order in *Retractable Technologies, Inc., and Thomas Shaw* v. *Becton Dickinson & Co.,* Civil Action No. 2:07-CV-250 (OF) (Jan. 20, 2009), 32 pages.

De Korte, D. et al., "Diversion of first blood volume results in a reduction of bacterial contamination for whole-blood collections," Vox Sanguinis, 83:13-16 (2002).

De Korte, D. et al., "Effects of skin disinfection method, deviation bag, and bacterial screening on clinical safety of platelet transfusions in the Netherlands," Transfusion, 46:476-485 (2006).

Declaration of Dr. Erik K. Antonsson, Ph.D., P.E., NAE, dated Dec. 5, 2024, 138 pages.

Declaration of Dr. Erik K. Antonsson, Ph.D., P.E., NAE (Mar. 21, 2023); 137 pages.

Declaration of Dr. Erik K. Antonsson, Ph.D., P.E., NAE, U.S. Pat. No. 11,529,081, dated Jan. 20, 2025, 164 pages.

Declaration of Dr. Erik K. Antonsson, Ph.D., P.E., NAE, U.S. Pat. No. 11,653,863, dated Jan. 20, 2025, 169 pages.

Declaration of Dr. Erik K. Antonsson, Ph.D., P.E., NAE, U.S. Pat. No. 11,903,709, dated Jan. 20, 2025, 161 pages.

Declaration of Dr. Morten Jensen under 37 C.F.R. § 1.132, Oct. 10, 2023, 400 pages.

Declaration of Professor Steven T. Wereley, PH.D., *Magnolia Medical Technologies, Inc.* v. *Kurin, Inc.,* C.A. 24-01124-CFC (D. Del.), Document # 181, dated Apr. 14, 2025, 37 pages.

Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.

Edwards Lifesciences, "Conservation. Safety. Simplicity. Edwards VAMP and VAMP Jr. Systems," 2002 Brochure. Retrieved from the Internet (Sep. 11, 19) https://www.medline.com/media/catalog/Docs/MKT/VAMPSYSTEMBROCHURE.PDF, 4 pages.

Ernst, D. J. et al., "NCCLS simplifies the order of draw: a brief history," MLO, pp. 26-27 (2004).

Exhibit 01—Defendant's Invalidity Contentions, Invalidity Claim Chart—U.S. Pat. No. 9,855,001 vs Barnard NPL, Aug. 30, 2019, 8 pages.

Exhibit 02—Defendant's Invalidity Contentions, Invalidity Claim Chart—U.S. Pat. No. 9,855,001 vs BD Needle NPL, Aug. 30, 2019, 7 pages.

Exhibit 03—Defendant's Invalidity Contentions, Invalidity Claim Chart—U.S. Pat. No. 9,855,001 vs U.S. Pat. No. 6,626,884, Aug. 30, 2019, 11 pages.

Exhibit 04—Defendant's Invalidity Contentions, Invalidity Claim Chart—U.S. Pat. No. 9,855,001 vs U.S. Pat. Pub. No. 2005/161112, Aug. 30, 2019, 22 pages.

Exhibit 05—Defendant's Invalidity Contentions, Invalidity Claim Chart—U.S. Pat. No. 9,855,001 vs U.S. Pat. No. 4,673,386, Aug. 30, 2019, 21 pages.

Exhibit 06—Defendant's Invalidity Contentions, Invalidity Claim Chart—U.S. Pat. No. 9,855,001 vs U.S. Pat. No. 4,904,240, Aug. 30, 2019, 15 pages.

Exhibit 07—Defendant's Invalidity Contentions, Invalidity Claim Chart—U.S. Pat. No. 9,855,001 vs Leukotrap NPL, Aug. 30, 2019, 38 pages.

Exhibit 09—Defendant's Invalidity Contentions, Invalidity Claim Chart—U.S. Pat. No. 9,855,001 vs U.S. Pat. No. 4,106,497, Aug. 30, 2019, 22 pages.

Exhibit 10—Defendant's Invalidity Contentions, Invalidity Claim Chart—U.S. Pat. No. 9,855,001 vs Stopcock-Syringe NPL, Aug. 30, 2019, 85 pages.

Exhibit 11—Defendant's Invalidity Contentions, Invalidity Claim Chart—U.S. Pat. No. 9,855,001 vs Ziegler NPL, Aug. 30, 2019, 8 pages.

Exhibit 12—Defendant's Invalidity Contentions, Invalidity Claim Chart—U.S. Pat. No. 10,028,689 vs Barnard NPL, Aug. 30, 2019, 12 pages.

Exhibit 13—Defendant's Invalidity Contentions, Invalidity Claim Chart—U.S. Pat. No. 10,028,689 vs U.S. Pat. No. 6,626,884, Aug. 30, 2019, 29 pages.

Exhibit 14—Defendant's Invalidity Contentions, Invalidity Claim Chart—U.S. Pat. No. 10,028,689 vs U.S. Pat. Pub. No. 2005/161112, Aug. 30, 2019, 48 pages.

Exhibit 15—Defendant's Invalidity Contentions, Invalidity Claim Chart—U.S. Pat. No. 10,028,689 vs U.S. Pat. No. 4,673,386, Aug. 30, 2019, 44 pages.

Exhibit 16—Defendant's Invalidity Contentions, Invalidity Claim Chart—U.S. Pat. No. 10,028,689 vs U.S. Pat. No. 4,904,240, Aug. 30, 2019, 31 pages.

Exhibit 17—Defendant's Invalidity Contentions, Invalidity Claim Chart—U.S. Pat. No. 10,028,689 vs Leukotrap NPL, Aug. 30, 2019, 113 pages.

Exhibit 19—Defendant's Invalidity Contentions, Invalidity Claim Chart—U.S. Pat. No. 10,028,689 vs U.S. Pat. No. 4,106,497, Aug. 30, 2019, 38 pages.

Exhibit 20—Defendant's Invalidity Contentions, Invalidity Claim Chart—U.S. Pat. No. 10,028,689 vs Stopcock-Syringe NPL, Aug. 30, 2019, 268 pages.

Exhibit 21—Defendant's Invalidity Contentions, Invalidity Claim Chart—U.S. Pat. No. 10,220,139 vs U.S. Pat. No. 6,626,884, Aug. 30, 2019, 35 pages.

Exhibit 22—Defendant's Invalidity Contentions, Invalidity Claim Chart—U.S. Pat. No. 10,220,139 vs U.S. Pat. Pub. No. 2005/161112, Aug. 30, 2019, 46 pages.

Exhibit 23—Defendant's Invalidity Contentions, Invalidity Claim Chart—U.S. Pat. No. 10,220,139 vs U.S. Pat. No. 4,207,870, Aug. 30, 2019, 20 pages.

Exhibit 24—Defendant's Invalidity Contentions, Invalidity Claim Chart—U.S. Pat. No. 10,220,139 vs U.S. Pat. No. 6,506,182, Aug. 30, 2019, 15 pages.

Exhibit 25—Defendant's Invalidity Contentions, Invalidity Claim Chart—U.S. Pat. No. 10,220,139 vs U.S. Pat. No. 4,673,386, Aug. 30, 2019, 53 pages.

Exhibit 26—Defendant's Invalidity Contentions, Invalidity Claim Chart—U.S. Pat. No. 10,220,139 vs U.S. Pat. No. 4,904,240, Aug. 30, 2019, 39 pages.

Exhibit 27—Defendant's Invalidity Contentions, Invalidity Claim Chart—U.S. Pat. No. 10,220,139 vs Leukotrap NPL, Aug. 30, 2019, 115 pages.

Exhibit 29—Defendant's Invalidity Contentions, Invalidity Claim Chart—U.S. Pat. No. 10,220,139 vs U.S. Pat. No. 4,106,497, Aug. 30, 2019, 45 pages.

Exhibit 30—Defendant's Invalidity Contentions, Invalidity Claim Chart—U.S. Pat. No. 10,220,139 vs Stopcock-Syringe NPL, Aug. 30, 2019, 246 pages.

Exhibit 31—Defendant's Invalidity Contentions, Invalidity Claim Chart—U.S. Pat. No. 10,220,139 vs U.S. Pat. No. 4,349,035, Aug. 30, 2019, 26 pages.

Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.

Exhibit 33—Defendant's Invalidity Contentions, Invalidity Claim Chart—U.S. Pat. No. 10,039,483 vs Barnard NPL, Aug. 30, 2019, 14 pages.

Exhibit 34—Defendant's Invalidity Contentions, Invalidity Claim Chart—U.S. Pat. No. 10,039,483 vs U.S. Pat. No. 6,626,884, Aug. 30, 2019, 22 pages.

Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.

Exhibit 36—Defendant's Invalidity Contentions, Invalidity Claim Chart—U.S. Pat. No. 10,039,483 vs U.S. Pat. No. 4,673,386, Aug. 30, 2019, 47 pages.

(56)  References Cited

OTHER PUBLICATIONS

Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Exhibit A to Magnolia Medical Technologies, Inc.'s Frist Amended Disclosure of Asserted Claims and Infringement Contentions, served May 28, 2024 in *Magnolia Medical Technologies, Inc. v. Kurin, Inc.;* Case No. 3-24-cv-00428 (S.D. Cal.), 240 pages.
Exhibit A1—Defendant's Invalidity Contentions, Invalidity Claim Chart—U.S. Pat. No. 9,855,002 vs U.S. Patent Publication No. 2005/0161112 A1, Jul. 29, 2024, 234 pages.
Exhibit A10—Defendant's Invalidity Contentions, Invalidity Claim Chart—U.S. Pat. No. 9,855,002 vs PortSyringe NPL, Jul. 29, 2024, 230 pages.
Exhibit A11—Defendant's Invalidity Contentions, Invalidity Claim Chart—U.S. Pat. No. 9,855,002 vs U.S. Pat. No. 4,056,101 NPL, Jul. 29, 2024, 111 pages.
Exhibit A12—Defendant's Invalidity Contentions, Invalidity Claim Chart—U.S. Pat. No. 9,855,002 vs U.S. Pat. No. 5,947,932, Jul. 29, 2024, 156 pages.
Exhibit A2—Defendant's Invalidity Contentions, Invalidity Claim Chart—U.S. Pat. No. 9,855,002 vs Japanese Patent Publication No. H10-2112742, Jul. 29, 2024, 281 pages.
Exhibit A3—Defendant's Invalidity Contentions, Invalidity Claim Chart—U.S. Pat. No. 9,855,002 vs U.S. Patent Publication No. 2007/0119508, Jul. 29, 2024, 368 pages.
Exhibit A4—Defendant's Invalidity Contentions, Invalidity Claim Chart—U.S. Pat. No. 9,855,002 vs U.S. Pat. No. 5,573,951, Jul. 29, 2024, 258 pages.
Exhibit A5—Defendant's Invalidity Contentions, Invalidity Claim Chart—U.S. Pat. No. 9,855,002 vs U.S. Pat. No. 6,626,884, Jul. 29, 2024, 116 pages.
Exhibit A6—Defendant's Invalidity Contentions, Invalidity Claim Chart—U.S. Pat. No. 9,855,002 vs U.S. Pat. No. 4,673,386, Jul. 29, 2024, 145 pages.
Exhibit A7—Defendant's Invalidity Contentions, Invalidity Claim Chart—U.S. Pat. No. 9,855,002 vs U.S. Pat. No. 4,904,240, Jul. 29, 2024, 147 pages.
Exhibit A8—Defendant's Invalidity Contentions, Invalidity Claim Chart—U.S. Pat. No. 9,855,002 vs Leukotrap NPL, Jul. 29, 2024, 144 pages.
Exhibit A9—Defendant's Invalidity Contentions, Invalidity Claim Chart—U.S. Pat. No. 9,855,002 vs U.S. Pat. No. 4,106,497, Jul. 29, 2024, 194 pages.
Exhibit B to Magnolia Medical Technologies, Inc.'s Frist Amended Disclosure of Asserted Claims and Infringement Contentions, served May 28, 2024 in *Magnolia Medical Technologies, Inc. v. Kurin, Inc.;* Case No. 3-24-cv-00428 (S.D. Cal.), 213 pages.
Exhibit B1—Defendant's Invalidity Contentions, Invalidity Claim Chart—U.S. Pat. No. 10,052,053 vs U.S. Patent Publication No. 2005/0161112 A1, Jul. 29, 2024, 237 pages.
Exhibit B10—Defendant's Invalidity Contentions, Invalidity Claim Chart—U.S. Pat. No. 10,052,053 vs PortSyringe NPL, Jul. 29, 2024, 229 pages.
Exhibit B11—Defendant's Invalidity Contentions, Invalidity Claim Chart—U.S. Pat. No. 10,052,053 vs U.S. Pat. No. 4,056,101 NPL, Jul. 29, 2024, 107 pages.
Exhibit B12—Defendant's Invalidity Contentions, Invalidity Claim Chart—U.S. Pat. No. 10,052,053 vs U.S. Pat. No. 5,947,932, Jul. 29, 2024, 154 pages.
Exhibit B2—Defendant's Invalidity Contentions, Invalidity Claim Chart—U.S. Pat. No. 10,052,053 vs Japanese Patent Publication No. H10-2112742, Jul. 29, 2024, 265 pages.
Exhibit B3—Defendant's Invalidity Contentions, Invalidity Claim Chart—U.S. Pat. No. 10,052,053 vs U.S. Patent Publication No. 2007/0119508, Jul. 29, 2024, 373 pages.
Exhibit B4—Defendant's Invalidity Contentions, Invalidity Claim Chart—U.S. Pat. No. 10,052,053 vs U.S. Pat. No. 5,573,951, Jul. 29, 2024, 264 pages.
Exhibit B5—Defendant's Invalidity Contentions, Invalidity Claim Chart—U.S. Pat. No. 10,052,053 vs U.S. Pat. No. 6,626,884, Jul. 29, 2024, 125 pages.
Exhibit B6—Defendant's Invalidity Contentions, Invalidity Claim Chart—U.S. Pat. No. 10,052,053 vs U.S. Pat. No. 4,673,386, Jul. 29, 2024, 146 pages.
Exhibit B7—Defendant's Invalidity Contentions, Invalidity Claim Chart—U.S. Pat. No. 10,052,053 vs U.S. Pat. No. 4,904,240, Jul. 29, 2024, 143 pages.
Exhibit B8—Defendant's Invalidity Contentions, Invalidity Claim Chart—U.S. Pat. No. 10,052,053 vs Leukotrap NPL, Jul. 29, 2024, 136 pages.
Exhibit B9—Defendant's Invalidity Contentions, Invalidity Claim Chart—U.S. Pat. No. 10,052,053 vs U.S. Pat. No. 4,106,497, Jul. 29, 2024, 191 pages.
Exhibit C to Magnolia's First Amended Disclosure of Asserted Claims and Infringement Contentions, *Magnolia Medical Technologies, Inc. v. Kurin, Inc.,* C.A. 3-24-cv-00428 (S.D. Cal.), served May 28, 2024, 250 pages.
Exhibit C1—Defendant's Invalidity Contentions, Invalidity Claim Chart—U.S. Pat. No. 11,529,081 vs U.S. Patent Publication No. 2005/0161112 A1, Jul. 29, 2024, 363 pages.
Exhibit C2—Defendant's Invalidity Contentions, Invalidity Claim Chart—U.S. Pat. No. 11,529,081 vs U.S. Pat. No. 9,855,002 and U.S. Pat. No. 10,052,053, Jul. 29, 2024, 488 pages.
Exhibit C3—Defendant's Invalidity Contentions, Invalidity Claim Chart—U.S. Pat. No. 11,529,081 vs U.S. Pat. No. 4,312,362, Jul. 29, 2024, 354 pages.
Exhibit C4—Defendant's Invalidity Contentions, Invalidity Claim Chart—U.S. Pat. No. 11,529,081 vs Kurin Lock NPL, Jul. 29, 2024, 361 pages.
Exhibit C5—Defendant's Invalidity Contentions, Invalidity Claim Chart—U.S. Pat. No. 11,529,081 vs U.S. Pat. No. 4,207,870, Jul. 29, 2024, 230 pages.
Exhibit C6—Defendant's Invalidity Contentions, Invalidity Claim Chart—U.S. Pat. No. 11,529,081 vs U.S. Patent Publication No. 2018/0177445, Jul. 29, 2024, 479 pages.
Exhibit C7—Defendant's Invalidity Contentions, Invalidity Claim Chart—U.S. Pat. No. 11,529,081 vs U.S. Pat. No. 9,820,682, Jul. 29, 2024, 338 pages.
Exhibit D to Magnolia's First Amended Disclosure of Asserted Claims and Infringement Contentions, *Magnolia Medical Technologies, Inc. v. Kurin, Inc.,* C.A. 3-24-cv-00428 (S.D. Cal.), served May 28, 2024, 222 pages.
Exhibit D1—Defendant's Invalidity Contentions, Invalidity Claim Chart—U.S. Pat. No. 11,653,863 vs U.S. Patent Publication No. 2005/0161112 A1, Jul. 29, 2024, 369 pages.
Exhibit D2—Defendant's Invalidity Contentions, Invalidity Claim Chart—U.S. Pat. No. 11,653,863 vs U.S. Pat. No. 9,855,002 and U.S. Pat. No. 10,052,053, Jul. 29, 2024, 481 pages.
Exhibit D3—Defendant's Invalidity Contentions, Invalidity Claim Chart—U.S. Pat. No. 11,653,863 vs U.S. Pat. No. 4,312,362, Jul. 29, 2024, 334 pages.
Exhibit D4—Defendant's Invalidity Contentions, Invalidity Claim Chart—U.S. Pat. No. 11,653,863 vs Kurin Lock NPL, Jul. 29, 2024, 363 pages.
Exhibit D5—Defendant's Invalidity Contentions, Invalidity Claim Chart—U.S. Pat. No. 11,653,863 vs U.S. Pat. No. 4,207,870, Jul. 29, 2024, 219 pages.

(56)  References Cited

OTHER PUBLICATIONS

Exhibit D6—Defendant's Invalidity Contentions, Invalidity Claim Chart—U.S. Pat. No. 11,653,863 vs U.S. Patent Publication No. 2018/0177445, Jul. 29, 2024, 447 pages.
Exhibit D7—Defendant's Invalidity Contentions, Invalidity Claim Chart—U.S. Pat. No. 11,653,863 vs U.S. Pat. No. 9,820,682, Jul. 29, 2024, 309 pages.
Exhibit E to Magnolia's First Amended Disclosure of Asserted Claims and Infringement Contentions, *Magnolia Medical Technologies, Inc.* v. *Kurin, Inc.,* C.A. 3-24-cv-00428 (S.D. Cal.), served May 28, 2024, 239 pages.
Exhibit E1—Defendant's Invalidity Contentions, Invalidity Claim Chart—U.S. Pat. No. 11,903,709 vs U.S. Patent Publication No. 2005/0161112 A1, Jul. 29, 2024, 442 pages.
Exhibit E2—Defendant's Invalidity Contentions, Invalidity Claim Chart—U.S. Pat. No. 11,903,709 vs U.S. Pat. No. 9,855,002 and U.S. Pat. No. 10,052,053, Jul. 29, 2024, 517 pages.
Exhibit E3—Defendant's Invalidity Contentions, Invalidity Claim Chart—U.S. Pat. No. 11,903,709 vs U.S. Pat. No. 4,312,362, Jul. 29, 2024, 438 pages.
Exhibit E4—Defendant's Invalidity Contentions, Invalidity Claim Chart—U.S. Pat. No. 11,903,709 vs Kurin Lock NPL, Jul. 29, 2024, 365 pages.
Exhibit E5—Defendant's Invalidity Contentions, Invalidity Claim Chart—U.S. Pat. No. 11,903,709 vs U.S. Pat. No. 4,207,870, Jul. 29, 2024, 351 pages.
Exhibit E6—Defendant's Invalidity Contentions, Invalidity Claim Chart—U.S. Pat. No. 11,903,709 vs U.S. Patent Publication No. 2018/0177445, Jul. 29, 2024, 559 pages.
Exhibit E7—Defendant's Invalidity Contentions, Invalidity Claim Chart—U.S. Pat. No. 11,903,709 vs U.S. Pat. No. 9,820,682, Jul. 29, 2024, 419 pages.
Extended European Search Report for European Application No. 16808502.5, mailed Jan. 23, 2019, 5 pages.
Extended European Search Report for European Application No. 17204012.3, mailed Feb. 14, 2018, 7 pages.
Extended European Search Report for European Application No. 17206745.6, mailed Feb. 19, 2018, 8 pages.
Extended European Search Report for European Application No. 18188136.8, mailed May 16, 2019, 9 pages.
Extended European Search Report for European Application No. 18855938.9, mailed Aug. 2, 2021, 7 pages.
Extended European Search Report for European Application No. 18885543.1, mailed Oct. 8, 2021, 8 pages.
Extended European Search Report for European Application No. 19156636.3, mailed Aug. 27, 2019, 7 pages.
Extended European Search Report for European Application No. 19190772.4, mailed Feb. 10, 2020, 7 pages.
Extended European Search Report for European Application No. 20176877.7, mailed Dec. 1, 2020, 9 pages.
Extended European Search Report for European Application No. 20207898.6, mailed Aug. 30, 2021, 8 pages.
Extended European Search Report for European Application No. 21167069.0, mailed Nov. 10, 2021, 9 pages.
Extended European Search Report for European Application No. 21167625.9, mailed Oct. 8, 2021, 7 pages.
Extended European Search Report for European Application No. 21197514, mailed Mar. 30, 2022.
Extended European Search Report for European Application No. 22158983.1, mailed Aug. 1, 2022, 9 pages.
Extended European Search Report for European Application No. 22172183.0, mailed Sep. 11, 2022, 7 pages.
Extended European Search Report for European Application No. 22194769.0, mailed Feb. 28, 2023, 9 pages.
Extended European Search Report for European Application No. 22210589.2, mailed Apr. 17, 2023, 6 pages.
Extended European Search Report for European Application No. 23153164.1, mailed Aug. 7, 2023, 8 pages.
Extended European Search Report for European Application No. 23171135.9, mailed Oct. 30, 2023, 8 pages.

Extended European Search Report for European Application No. 23182529.0, mailed Dec. 19, 2023, 13 pages.
Extended European Search Report for European Application No. 23209844.2, mailed Mar. 20, 2024, 9 pages.
Extended European Search Report for European Application No. 23217471.4, mailed May 22, 2024, 8 pages.
Extended European Search Report for European Application No. 23218666.8 mailed Apr. 18, 2024, 9 pages.
Extended European Search Report for European Application No. 24217446.4, mailed Apr. 17, 2025, 8 pages.
File History of U.S. Appl. No. 15/432,310, filed Feb. 14, 2017, 246 pages.
File History of U.S. Appl. No. 15/829,023, filed Dec. 1, 2017, 348 pages.
File History of U.S. Appl. No. 17/883,339, filed Aug. 8, 2022, 484 pages.
File History of U.S. Appl. No. 17/883,340, filed May 23, 2023, 801 pages.
File History of U.S. Appl. No. 18/130,207, filed Apr. 3, 2023, 476 pages.
File History of U.S. Appl. No. 15/832,091, filed Dec. 5, 2017, 360 pages.
File History of U.S. Appl. No. 60/969,394, filed Aug. 31, 2007, Inventor Humes; 95 pages; Exhibit 181-3.
First Amended Complaint, Document 5, *Magnolia Medical Technologies, Inc.* v. *Kurin, Inc.,* C.A. 19-00097-CFC-CJB (D. Del.), filed Mar. 7, 2019, 40 pages.
Garstecki, P., et al.; "Formation of droplets and bubbles in a microfluidic T-junction-scaling and mechanism of break-up," Lab Chip; 6(3):437-446 (Mar. 2006).
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
Gottlieb, T., "Hazards of Bacterial Contamination of Blood Products," Anaesth Intens Care, 21:20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, pp. 575-589 (2003).
International Search Report and Written Opinion for International Application No. PCT/US2007/087951, mailed May 16, 2008, 8 pages.
International Search Report and Written Opinion for International Application No. PCT/US2013/043289, mailed Oct. 24, 2013, 15 pages.
International Search Report and Written Opinion for International Application No. PCT/US2013/052493, mailed Nov. 27, 2013, 7 pages.
International Search Report and Written Opinion for International Application No. PCT/US2013/063975, mailed Mar. 20, 2014, 16 pages.
International Search Report and Written Opinion for International Application No. PCT/US2013/071491, mailed Aug. 5, 2014, 9 pages.
International Search Report and Written Opinion for International Application No. PCT/US2013/072563, mailed Feb. 7, 2014, 11 pages.
International Search Report and Written Opinion for International Application No. PCT/US2013/073080, mailed Feb. 18, 2014, 14 pages.
International Search Report and Written Opinion for International Application No. PCT/US2016/037160, mailed Sep. 30, 2016, 15 pages.
International Search Report and Written Opinion for International Application No. PCT/US2018/036910, mailed Sep. 4, 2018, 13 pages.
International Search Report and Written Opinion for International Application No. PCT/US2018/050621, mailed Nov. 26, 2018, 11 pages.

(56) References Cited

OTHER PUBLICATIONS

International Search Report and Written Opinion for International Application No. PCT/US2018/064561, mailed Feb. 11, 2019, 9 pages.

International Search Report and Written Opinion for International Application No. PCT/US2019/034626, mailed Aug. 22, 2019, 16 pages.

International Search Report and Written Opinion for International Application No. PCT/US2020/022125, mailed May 26, 2020, 17 pages.

Kim, J. Y. et al., "The Sum of the Parts is Greater Than the Whole: Reducing Blood Culture Contamination," Annals of Internal Medicine, 154:202-203 (2011).

Kurin blood culture collection; Device Description; KUR-MAG-DE000147; pp. 1-9; Exhibit 181-6 (2025).

Kurin's Post-Trial Motion for Judgment as a Matter of Law Regarding Indefiniteness, Document 451, *Magnolia Medical Technologies, Inc.* v. *Kurin, Inc.,* C.A. 19-00097-CFC-CJB (D. Del.), filed Sep. 9, 2022, 24 pages.

Lanteri et al., "Reduction of Blood Culture Contaminations in the Emergency Department," Department of Emergency Medicine, San Antonio Military Medical Center (2016), 1 page.

Levin, P. D. et al., "Use of the Nonwire Central Line Hub to Reduce Blood Culture Contamination," Chest, 143(3):640-645 (2013).

Li, Y., et al.; "Direct labeling and visualization of blood vessels with lipophilic carbocyanine dye Dil," Nature Protocols; 3(11):1703-1708 (2008).

Litigation Search Report CRU 3999 for Reexamination Application No. 90/019,177 dated Mar. 23, 2023, 95 pages.

Liumbruno, G. M. et al., "Reduction of the risk of bacterial contamination of blood components through diversion of the first part of the donation of blood and blood components," Blood Transfus., 7:86-93 (2009).

Magnolia's Answer Brief in Opposition to Kurin's Post-Trial Motion for Judgment as a Matter of Law Regarding Indefiniteness, Document 463, *Magnolia Medical Technologies, Inc.* v. *Kurin, Inc.,* C.A. 19-00097-CFC-CJB (D. Del.), filed Sep. 30, 2022, 25 pages.

Magnolia's Answering Brief in Opposition to Kurin's Motion for Summary Judgement (No. 3) of Noninfringement of All Asserted Claims (Redacted), Document 389, *Magnolia Medical Technologies, Inc.* v. *Kurin, Inc.,* C.A. 19-00097-CFC-CJB (D. Del.), Filed Jul. 14, 2021, 15 pages.

Magnolia's Corrected Opening Claim Construction Brief, *Magnolia Medical Technologies, Inc.* v. *Kurin, Inc.,* C.A. 24-01124-CFC (D. Del.), dated Nov. 7, 2024, 32 pages.

Magnolia's Supplemental Claim Construction Brief, *Magnolia Medical Technologies, Inc.* v. *Kurin, Inc.,* C.A. 24-01124-CFC (D. Del.), Document # 180, dated Apr. 14, 2025, 30 pages.

Marshall, L.A., et al.; "An injection molded microchip for nucleic acid purification from 25 microliter samples using isotachophoresis," J Chromatogr A.; 1331; pp. 139-142 (Feb. 2014).

Mayer, G. A, "A Method for the Reliable Determination of Clotting Time in Whole Blood," Can Med Assoc J., 72(12):927-929 (1955).

McDonald, C. P., "Interventions Implemented to Reduce the Risk of Transmission of Bacteria by Transfusion in the English National Blood Service," Transfus Med Hemother, 38:255-258 (2011).

McDonald, C.P.; "Bacterial risk reduction by improved donor arm disinfection, diversion and bacterial screening," Transfus Med., (2006); 16(6):381-396.

Meissner, G. F. et al., "A Method Based on the Use of Whole Venous Blood in Capillary Tubes," American Journal of Clinical Pathology, 33(2):29-31 (1963).

Memorandum Opinion in Support of Judgment of Non-infringement as a Matter of Law, Document 536, *Magnolia Medical Technologies, Inc.* v. *Kurin, Inc.,* C.A. 19-00097-CFC-CJB (D. Del.), May 14, 2024, 21 pages.

Memorandum Opinion on Kurin's Motion for Judgment as a Matter of Law Regarding Indefiniteness, Document 514, *Magnolia Medical Technologies, Inc.* v. *Kurin, Inc.,* C.A. 19-00097-CFC-CJB, filed Aug. 4, 2023, 38 pages.

Murphy, M., "Better Blood Transfusion," Journal of the Intensive Core Society, 4(3):78-80 (2003).

Napolitano, M. et al., "Quality control of bacterial contamination of blood components: the feasibility of diversion system testing," Blood Transfus, 2:231-232 (2004).

Nielsen et al., "Initial Specimen Diversion Device Reduces Blood Culture Contamination and Vancomycin Use in Academic Medical Centre," J. Hospital Infection, vol. 120:127-133 (Feb. 2022).

Norberg, A et al., "Contamination Rates of Blood Cultures Obtained by Dedicated Phlebotomy vs Intravenous Catheter," JAMA, 289(6):726-729 (2003).

Office Action for Australian Application No. 2018279941, mailed Mar. 20, 2023, 3 pages.

Office Action for Australian Application No. 2018334138, mailed Jun. 24, 2023, 3 pages.

Office Action for Australian Application No. 2020218544, mailed Jul. 31, 2024, 3 pages.

Office Action for Australian Application No. 2020234829, mailed Nov. 15, 2024, 3 pages.

Office Action for Australian Application No. 2022200818, mailed May 11, 2023, 4 pages.

Office Action for Australian Application No. 2024203105, mailed Jan. 21, 2025, 3 pages.

Office Action for Australian Application No. 2024203140, mailed Apr. 8, 2025, 4 pages.

Office Action for Canadian Application No. 2932536, mailed Nov. 8, 2019, 6 pages.

Office Action for Canadian Application No. 2932536, mailed Oct. 23, 2020, 6 pages.

Office Action for Canadian Application No. 3066670, mailed Oct. 4, 2024, 4 pages.

Office Action for Canadian Application No. 3074105, mailed Nov. 15, 2024, 5 pages.

Office Action for Canadian Application No. 3087992, mailed Mar. 20, 2025, 4 pages.

Office Action for Canadian Application No. 3120161, mailed Jun. 20, 2022, 4 pages.

Office Action for Canadian Application No. 3129065, mailed Feb. 11, 2025, 3 pages.

Office Action for Canadian Application No. 3136331, mailed Feb. 21, 2023, 4 pages.

Office Action for Canadian Application No. 3183294, mailed Aug. 19, 2024, 5 pages.

Office Action for Chinese Application No. 201380040468.7, mailed Jun. 30, 2016, with English Translation, 9 pages.

Office Action for Chinese Application No. 201380072185.0, mailed Sep. 28, 2016, with English Translation, 17 pages.

Office Action for Chinese Application No. 201811146373.4, mailed Apr. 8, 2025, with English translation, 18 pages.

Office Action for Chinese Application No. 201811146373.4, mailed Aug. 25, 2021, with English language translation, 10 pages.

Office Action for Chinese Application No. 201811146373.4, mailed Jan. 29, 2022, with English language translation, 21 pages.

Office Action for Chinese Application No. 201811146373.4, mailed Nov. 4, 2020, with English language translation, 17 pages.

Office Action for Chinese Application No. 201880050862.1, mailed Mar. 14, 2022, with English translation, 19 pages.

Office Action for Chinese Application No. 201880066848.0, mailed Apr. 20, 2022, with English Translation, 10 pages.

Office Action for Chinese Application No. 201880088771.7, mailed Sep. 3, 2021, with English translation, 17 pages.

Office Action for Chinese Application No. 202080025953.7, mailed Aug. 28, 2024, with English language translation, 26 pages.

Office Action for Chinese Application No. 202080025953.7, mailed Dec. 17, 2024, with English language translation, 22 pages.

Office Action for Chinese Application No. 202080025953.7, mailed Jan. 9, 2024, with English translation, 27 pages.

Office Action for Chinese Application No. 202080033513.6, mailed Oct. 9, 2022, with English translation, 19 pages.

Office Action for European Application No. 17206745.6, mailed Feb. 18, 2020, 4 pages.

Office Action for European Application No. 20709440.0, mailed Feb. 18, 2025, 6 pages.

(56)　　　　　References Cited

OTHER PUBLICATIONS

Office Action for European Application No. 20716348.6, mailed Jul. 12, 2022, 7 pages.
Office Action for Ex Parte Reexamination for U.S. Appl. No. 90/019,177, mailed Aug. 9, 2023, 11 pages.
Office Action for Ex Parte Reexamination for U.S. Appl. No. 90/019,177, mailed Dec. 1, 2023, 19 pages.
Office Action for Indian Application No. 202017008581, mailed Mar. 8, 2022, with English translation, 7 pages.
Office Action for Israeli Application No. 285289, mailed May 6, 2024, 4 pages.
Office Action for Israeli Application No. 286263, mailed May 12, 2024, 4 pages.
Office Action for Israeli Application No. 309638, mailed Jul. 16, 2024, 3 pages.
Office Action for Japanese Application No. 2015-545813, mailed Jul. 4, 2017, with English Translation, 14 pages.
Office Action for Japanese Application No. 2018-081980, mailed Feb. 21, 2019, with English Translation, 9 pages.
Office Action for Japanese Application No. 2018-081980, mailed Jan. 30, 2020, 11 pages.
Office Action for Japanese Application No. 2018-086721, mailed Mar. 15, 2019, with English Translation, 6 pages.
Office Action for Japanese Application No. 2019-230734, mailed Jan. 22, 2021, with English Translation, 9 pages.
Office Action for Japanese Application No. 2019-230734, mailed Jan. 5, 2022, with English Translation, 6 pages.
Office Action for Japanese Application No. 2020-075727, mailed Jul. 21, 2021, with English translation, 37 pages.
Office Action for Japanese Application No. 2020-094488, mailed Aug. 2, 2021, with English Translation, 4 pages.
Office Action for Japanese Application No. 2020-094488, mailed Mar. 31, 2022, with English Translation, 6 pages.
Office Action for Japanese Application No. 2020-511930, mailed Aug. 23, 2022, with English translation, 9 pages.
Office Action for Japanese Application No. 2020-517772, mailed Dec. 26, 2022, with English Translation, 6 pages.
Office Action for Japanese Application No. 2020-517772, mailed Mar. 14, 2022, with English Translation, 13 pages.
Office Action for Japanese Application No. 2020-550048, mailed Aug. 5, 2022, with English Translation, 5 pages.
Office Action for Japanese Application No. 2020-566232 mailed Apr. 12, 2023, with English translation, 27 pages.
Office Action for Japanese Application No. 2021-546225, mailed Dec. 19, 2023, with English translation, 11 pages.
Office Action for Japanese Application No. 2021-552145, mailed Jan. 15, 2024, with English Translation, 9 pages.
Office Action for Japanese Application No. 2022-074696 mailed Feb. 20, 2023, with English translation, 11 pages.
Office Action for Japanese Application No. 2022-184274, mailed Jun. 14, 2024, with English Translation, 4 pages.
Office Action for Japanese Application No. 2022-184274, mailed Oct. 27, 2023, with English translation, 6 pages.
Office Action for Japanese Application No. 2022-212405, mailed Jun. 20, 2024, with English translation, 6 pages.
Office Action for Japanese Application No. 2023-075104 mailed Feb. 29, 2024, with English Translation, 9 pages.
Office Action for Japanese Application No. 2024-020482 mailed Mar. 11, 2025, with English Translation, 16 pages.
Office Action for United Kingdom Application No. GB 1805101.1, mailed May 25, 2018, 8 pages.
Office Action for U.S. Appl. No. 11/955,635, mailed Dec. 3, 2010, 11 pages.
Office Action for U.S. Appl. No. 11/955,635, mailed Jul. 22, 2010, 11 pages.
Office Action for U.S. Appl. No. 13/335,241, mailed Apr. 20, 2012, 12 pages.
Office Action for U.S. Appl. No. 13/458,508, mailed Jul. 24, 2012, 13 pages.

Office Action for U.S. Appl. No. 13/675,295, mailed May 23, 2013, 15 pages.
Office Action for U.S. Appl. No. 13/952,964, mailed Mar. 20, 2015, 11 pages.
Office Action for U.S. Appl. No. 13/954,528, mailed Mar. 17, 2014, 10 pages.
Office Action for U.S. Appl. No. 14/049,326, mailed Apr. 24, 2015, 10 pages.
Office Action for U.S. Appl. No. 14/089,267, mailed Jun. 19, 2014, 13 pages.
Office Action for U.S. Appl. No. 14/096,826, mailed Jul. 26, 2017, 12 pages.
Office Action for U.S. Appl. No. 14/096,826, mailed Mar. 8, 2018, 14 pages.
Office Action for U.S. Appl. No. 14/493,796, mailed Jan. 27, 2015, 7 pages.
Office Action for U.S. Appl. No. 14/494,208, mailed Jan. 27, 2015, 7 pages.
Office Action for U.S. Appl. No. 14/498,102, mailed Oct. 17, 2017, 20 pages.
Office Action for U.S. Appl. No. 14/498,102, mailed Sep. 24, 2018, 18 pages.
Office Action for U.S. Appl. No. 14/662,676, mailed Sep. 5, 2018, 25 pages.
Office Action for U.S. Appl. No. 14/712,437 mailed Oct. 25, 2018, 20 pages.
Office Action for U.S. Appl. No. 14/728,318, mailed Jul. 18, 2019, 27 pages.
Office Action for U.S. Appl. No. 14/838,794, mailed Aug. 3, 2017, 8 pages.
Office Action for U.S. Appl. No. 14/926,784, mailed Jan. 15, 2019, 15 pages.
Office Action for U.S. Appl. No. 14/926,784, mailed Jan. 21, 2020, 17 pages.
Office Action for U.S. Appl. No. 14/926,784, mailed May 25, 2018, 15 pages.
Office Action for U.S. Appl. No. 15/088,842, mailed Nov. 23, 2016, 20 pages.
Office Action for U.S. Appl. No. 15/180,454, mailed Apr. 1, 2020, 28 pages.
Office Action for U.S. Appl. No. 15/180,454, mailed Jan. 21, 2021, 24 pages.
Office Action for U.S. Appl. No. 15/180,454, mailed Jul. 25, 2019, 27 pages.
Office Action for U.S. Appl. No. 15/432,310, mailed Apr. 12, 2017, 14 pages.
Office Action for U.S. Appl. No. 15/435,684, mailed Jun. 12, 2017, 19 pages.
Office Action for U.S. Appl. No. 15/448,891, mailed Jun. 16, 2017, 25 pages.
Office Action for U.S. Appl. No. 15/457,082, mailed Jun. 15, 2017, 22 pages.
Office Action for U.S. Appl. No. 15/829,015, mailed Feb. 6, 2018, 24 pages.
Office Action for U.S. Appl. No. 15/829,018, mailed Feb. 16, 2018, 13 pages.
Office Action for U.S. Appl. No. 15/829,023, mailed Feb. 7, 2018, 25 pages.
Office Action for U.S. Appl. No. 15/832,055, mailed Feb. 8, 2018, 21 pages.
Office Action for U.S. Appl. No. 15/832,087, mailed Feb. 7, 2018, 24 pages.
Office Action for U.S. Appl. No. 15/832,091, mailed Feb. 22, 2018, 16 pages.
Office Action for U.S. Appl. No. 15/854,273, mailed Jan. 13, 2020, 13 pages.
Office Action for U.S. Appl. No. 15/854,273, mailed Mar. 15, 2019, 19 pages.
Office Action for U.S. Appl. No. 15/854,273, mailed Sep. 7, 2018, 15 pages.
Office Action for U.S. Appl. No. 16/004,955, mailed Feb. 16, 2021, 28 pages.

(56) References Cited

OTHER PUBLICATIONS

Office Action for U.S. Appl. No. 16/129,066, mailed Sep. 3, 2020, 13 pages.
Office Action for U.S. Appl. No. 16/213,005, mailed Feb. 3, 2021, 15 pages.
Office Action for U.S. Appl. No. 16/255,055, mailed Mar. 18, 2019, 16 pages.
Office Action for U.S. Appl. No. 16/255,058, mailed Mar. 30, 2021, 16 pages.
Office Action for U.S. Appl. No. 16/274,835, mailed Feb. 12, 2021, 17 pages.
Office Action for U.S. Appl. No. 16/299,962, mailed Dec. 26, 2019, 14 pages.
Office Action for U.S. Appl. No. 16/299,962, mailed Dec. 9, 2020, 15 pages.
Office Action for U.S. Appl. No. 16/299,962, mailed Jun. 15, 2021, 17 pages.
Office Action for U.S. Appl. No. 16/299,962, mailed May 2, 2019, 14 pages.
Office Action for U.S. Appl. No. 16/376,745, mailed May 14, 2021, 13 pages.
Office Action for U.S. Appl. No. 16/379,128, mailed Apr. 26, 2022, 14 pages.
Office Action for U.S. Appl. No. 16/426,380, mailed May 7, 2021, 28 pages.
Office Action for U.S. Appl. No. 16/426,380, mailed Oct. 30, 2020, 29 pages.
Office Action for U.S. Appl. No. 16/789,034, mailed Feb. 9, 2023, 11 pages.
Office Action for U.S. Appl. No. 16/815,526, mailed Aug. 18, 2022, 13 pages.
Office Action for U.S. Appl. No. 16/934,975, mailed Oct. 6, 2022, 18 pages.
Office Action for U.S. Appl. No. 17/136,882, mailed Apr. 19, 2024, 8 pages.
Office Action for U.S. Appl. No. 17/136,882, mailed Dec. 31, 2024, 6 pages.
Office Action for U.S. Appl. No. 17/136,882, mailed Jun. 9, 2023, 11 pages.
Office Action for U.S. Appl. No. 17/136,882, mailed Nov. 8, 2023, 11 pages.
Office Action for U.S. Appl. No. 17/138,056, mailed Dec. 21, 2022, 11 pages.
Office Action for U.S. Appl. No. 17/388,971, mailed Nov. 23, 2021, 19 pages.
Office Action for U.S. Appl. No. 17/388,979, mailed Dec. 8, 2021, 21 pages.
Office Action for U.S. Appl. No. 17/390,249 mailed Nov. 8, 2023, 9 pages.
Office Action for U.S. Appl. No. 17/403,500, mailed Jul. 28, 2023, 28 pages.
Office Action for U.S. Appl. No. 17/403,500, mailed May 20, 2024, 28 pages.
Office Action for U.S. Appl. No. 17/403,500, mailed Nov. 13, 2024, 27 pages.
Office Action for U.S. Appl. No. 17/403,500, mailed Sep. 27, 2022, 29 pages.
Office Action for U.S. Appl. No. 17/516,887, mailed Jan. 13, 2025, 42 pages.
Office Action for U.S. Appl. No. 17/525,682, mailed Feb. 7, 2022, 12 pages.
Office Action for U.S. Appl. No. 17/532,382, mailed Feb. 7, 2022, 10 pages.
Office Action for U.S. Appl. No. 17/583,791, mailed Dec. 23, 2024, 19 pages.
Office Action for U.S. Appl. No. 17/591,237, mailed Aug. 25, 2023, 25 pages.
Office Action for U.S. Appl. No. 17/591,237, mailed Aug. 4, 2022, 26 pages.

Office Action for U.S. Appl. No. 17/591,237, mailed Feb. 16, 2023, 34 pages.
Office Action for U.S. Appl. No. 17/591,237, mailed Jan. 24, 2025, 34 pages.
Office Action for U.S. Appl. No. 17/591,237, mailed May 3, 2022, 20 pages.
Office Action for U.S. Appl. No. 17/591,239, mailed Aug. 23, 2023, 23 pages.
Office Action for U.S. Appl. No. 17/591,239, mailed Aug. 4, 2022, 26 pages.
Office Action for U.S. Appl. No. 17/591,239, mailed Feb. 17, 2023, 34 pages.
Office Action for U.S. Appl. No. 17/591,239, mailed Jan. 24, 2025, 32 pages.
Office Action for U.S. Appl. No. 17/591,239, mailed May 3, 2022, 21 pages.
Office Action for U.S. Appl. No. 17/684,920, mailed Jan. 31, 2023, 9 pages.
Office Action for U.S. Appl. No. 17/684,920, mailed Jul. 11, 2022, 12 pages.
Office Action for U.S. Appl. No. 17/710,389, mailed Jun. 16, 2022, 25 pages.
Office Action for U.S. Appl. No. 17/710,401, mailed Jul. 6, 2022, 22 pages.
Office Action for U.S. Appl. No. 17/710,411, mailed Jul. 6, 2022, 22 pages.
Office Action for U.S. Appl. No. 17/863,605, mailed Nov. 28, 2023, 15 pages.
Office Action for U.S. Appl. No. 18/227,185, mailed Apr. 18, 2024, 18 pages.
Office Action for U.S. Appl. No. 18/227,185, mailed Oct. 31, 2024, 17 pages.
Office Action for U.S. Appl. No. 18/240,178, mailed Feb. 27, 2025, 12 pages.
Office Action for U.S. Appl. No. 18/240,178, mailed Jun. 12, 2024, 16 pages.
Office Action for U.S. Appl. No. 18/380,259, mailed Jan. 29, 2024, 33 pages.
Office Action for U.S. Appl. No. 18/380,259, mailed Oct. 16, 2024, 15 pages.
Office Action for U.S. Appl. No. 18/381,369, mailed Nov. 28, 2023, 16 pages.
Office Action for U.S. Appl. No. 18/399,007, mailed Mar. 7, 2024, 8 pages.
Office Action for U.S. Appl. No. 18/407,010, mailed Mar. 13, 2024, 8 pages.
Office Action for U.S. Appl. No. 18/407,010, mailed Sep. 6, 2024, 11 pages.
Office Action for U.S. Appl. No. 18/675,824, mailed Jul. 26, 2024, 13 pages.
Office Action for U.S. Appl. No. 18/676,186, mailed Aug. 5, 2024, 13 pages.
Office Action for U.S. Appl. No. 18/680,331, mailed Mar. 25, 2025, 8 pages.
Office Action for U.S. Appl. No. 18/680,348, mailed Mar. 25, 2025, 7 pages.
Office Action for U.S. Appl. No. 18/680,377, mailed Mar. 26, 2025, 12 pages.
Office Action for U.S. Appl. No. 18/680,439, mailed Mar. 31, 2025, 8 pages.
Office Action for U.S. Appl. No. 18/680,466, mailed Dec. 30, 2024, 7 pages.
Office Action for U.S. Appl. No. 18/960,441, mailed Jan. 17, 2025, 8 pages.
Office Action for U.S. Appl. No. 18/990,547, mailed Jan. 31, 2025, 10 pages.
Opening Expert Report of Dr. Juan G. Santiago Regarding Infringement of U.S. Pat. No. 9,855,001 and U.S. Pat. No. 10,039,483 (Redacted), Document 242, *Magnolia Medical Technologies, Inc.* v. *Kurin, Inc.,* C.A. 19-00097-CFC-CJB (D. Del.), filed Jan. 20, 2021, 555 pages.
Order Granting Request for Ex Parte Reexamination for U.S. Appl. No. 90/019,177, mailed Apr. 26, 2023, 16 pages.

(56)          References Cited

OTHER PUBLICATIONS

Order Granting Request for Ex Parte Reexamination for U.S. Appl. No. 90/019,823, dated Feb. 24, 2025, 16 pages.
Order Granting Request for Ex Parte Reexamination for U.S. Appl. No. 90/019,824, dated Feb. 24, 2025, 18 pages.
Order Granting Request for Ex Parte Reexamination for U.S. Appl. No. 90/019,825, dated Feb. 25, 2025, 15 pages.
Order of Draw for Multiple Tube Collections, LabNotes, a newsletter from BD Diagnostics,—Preanalytical Systems, 17(1):3 (2007), 1 page.
Original Claims of U.S. Appl. No. 14/712,431, filed May 14, 2015. 6 pages.
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Partial Judgment of Non-Infringement of U.S. Pat. No. 9855001, Document 410, *Magnolia Medical Technologies, Inc.* v. *Kurin, Inc.,* C.A. 19-00097-CFC-CJB (D.Del.), filed Jun. 10, 2022, 3 pages.
Patel, R. et al., "Optimized Pathogen Detection with 30-Compared to 20-Milliliter Blood Culture Draws," Journal of Clinical Microbiology, 49(12):4047-4051 (2011).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Preliminary Amendment of U.S. Appl. No. 17/591,237, filed Feb. 2, 2022, 12 pages.
Preliminary Amendment of U.S. Appl. No. 17/591,239, filed Feb. 2, 2022, 12 pages.
Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Request for Ex Parte Reexamination for U.S. Pat. No. 10,039,483 Under 35 U.S.C. § 302 and 37 C.F.R. § 1.510 filed Mar. 22, 2023, 84 pages.
Request for Ex Parte Reexamination for U.S. Pat. No. 10,052,053 Under 35 U.S.C. § 302 and 37 C.F.R. § 1.510, filed Dec. 6, 2024, 144 pages.
Request for Ex Parte Reexamination for U.S. Pat. No. 11,529,081 Under 35 U.S.C. § 302 and 37 C.F.R. § 1.510, filed Jan. 21, 2025, 179 pages.
Request for Ex Parte Reexamination for U.S. Pat. No. 11,653,863 Under 35 U.S.C. § 302 and 37 C.F.R. § 1.510, filed Jan. 21, 2025, 180 pages.
Request for Ex Parte Reexamination for U.S. Pat. No. 11,903,709 Under 35 U.S.C. § 302 and 37 C.F.R. § 1.510, filed Jan. 21, 2025, 176 pages.
Request for Ex Parte Reexamination for U.S. Pat. No. 9,855,002 Under 35 U.S.C. § 302 and 37 C.F.R. § 1.510, filed Dec. 6, 2024, 147 pages.
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Schuur, J., "Blood Cultures: When Do they Help and When Do They Harm?" Brigham & Women's Hospital, Department of Emergency Medicine, (Jun. 21-23, 2012), 42 pages.

Shen, H., et al.; "A microfluidic chip based sequential injection system with trapped droplet liquid-liquid extraction and chemiluminescence detection," Lab Chip; 6(10):1387-1389 (Oct. 2006).
Sheppard, C. A., et al.; "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1):11-19 (2000).
Sibley, C. D., et al.; "Molecular Methods for Pathogen and Microbial Community Detection and Characterization: Current and Potential Application in Diagnostic Microbiology," Infection, Genetics and Evolution 12:505-521 (2012).
Skoglund et al., "Estimated Clinical and Economic Impact through Use of a Novel Blood Collection Device To Reduce Blood Culture Contamination in the Emergency Department: a Cost-Benefit Analysis," J Clin Microbiol. (Jan. 2019); 57(1):e01015-18, 10 pages.
Stay Order, Document 515, *Magnolia Medical Technologies, Inc.* v. *Kurin, Inc.,* C.A. 19-00097-CFC-CJB, filed Aug. 4, 2023, 1 page.
Stay Order, Document 516, *Magnolia Medical Technologies, Inc.* v. *Kurin, Inc.,* C.A. 19-00097-CFC-CJB, filed Aug. 4, 2023, 2 pages.
Steed et al., "Study Demonstrates Reduction in Blood Culture Contamination Rates with Novel Blood Culture Collection Device," Clinical Lab Products Magazine (Feb. 2018), 2 pages.
Stohl, S. et al., "Blood Cultures at Central Line Insertion in the Intensive Care Unit: Comparison with Peripheral Venipuncture," Journal of Clinical Microbiology, 49(7):2398-2403 (2011).
Supplementary European Search Report for EP Application No. 13845555.5, dated Jul. 12, 2016, 6 pages.
Supplementary European Search Report for European Application No. 13797732.8, mailed Dec. 7, 2015, 5 pages.
Supplementary European Search Report for European Application No. 13860741.1, mailed Jun. 7, 2016, 5 pages.
Tang, M. et al., "Closed Blood Conservation Device for Reducing Catheter-Related Infections in Children After Cardiac Surgery," Critical Care Nurse, 34(5):53-61 (2014).
Tompkins et al., "Getting to Zero: Impact of A Device To Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
Transcript of Jury Trial Proceedings of Jul. 25, 2022, Document 434, *Magnolia Medical Technologies, Inc.* v. *Kurin, Inc.,* C.A. 19-00097-CFC-CJB (D. Del.), filed Jul. 25, 2022, 402 pages.
Transcript of Jury Trial Proceedings of Jul. 27, 2022, Document 438, *Magnolia Medical Technologies, Inc.* v. *Kurin, Inc.,* C.A. 19-00097-CFC-CJB (D. Del.), filed Jul. 27, 2022, 412 pages.
U.S. Appl. No. 62/439,426, filed Dec. 27, 2016, Inventor Rogers, et al.; 126 pages.
Vent Definition & Meaning—Merriam-Webster (https://www.merriam-webster.com/dictionary/vent, accessed Mar. 21, 2023); 16 pages.
Vent, n.2: Oxford English Dictionary (https://www.oed.com/view/Entry/222207?&print, accessed Feb. 16, 2023); 12 pages.
Verdict Form Phase 1 (Redacted), Document 437, *Magnolia Medical Technologies, Inc.* v. *Kurin, Inc.,* C.A. 19-00097-CFC-CJB (D. Del.), filed Jul. 26, 2022, 3 pages.
Verdict Form Phase 2 (Redacted), Document 443, *Magnolia Medical Technologies, Inc.* v. *Kurin, Inc.,* C.A. 19-00097-CFC-CJB (D. Del.), filed Jul. 29, 2022, 5 pages.
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23: pp. 63-66 (2012).
Weinbaum, F. I. et al., "Doing It Right the First Time: Quality Improvement and the Contaminant Blood Culture," Journal of Clinical Microbiology, 35(3):563-565 (1997).
Weinstein, M.P., "Current Blood Culture Methods and Systems: Clinical Concepts, Technology, and Interpretation of Results," Clinical Infectious Diseases, 23:40-46 (1996).

(56)         References Cited

OTHER PUBLICATIONS

Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).

Weinstein, M.P., "Minireview: Blood Culture Contamination: Persisting Problems and Partial Progress," Journal of Clinical Microbiology, 41(6):2275-2278 (2003).

Ziegler, et al., "Controlled Clinical Laboratory Comparison of Two Supplemented Aerobic and Anaerobic Media Used in Automated Blood Culture Systems To Detect Bloodstream Infections," J. Clinical Microbiology, 36(3):657-661 (1998).

Zimmerman et al., "Reducing Blood Culture Contamination Using an Initial Specimen Diversion Device," Am. J. Infection Control, vol. 47, No. 7, pp. 822-826 (Jan. 2019).

Zimmon, D. S. et al., "Effect of Portal Venous Blood Flow Diversion on Portal Pressure," J Clin Invest, 65(6): 1388-1397 (1980).

Zundert, A V., "New Closed IV Catheter System," Acta Anaesth. Belg., 56:283-285 (2005).

Office Action for U.S. Appl. No. 17/869,256, mailed May 5, 2025, 24 pages.

Declaration of Dr. Erik K. Antonsson, Ph.D., P.E., Nae, U.S. Pat. No. 9,855,002, dated Dec. 5, 2024, 141 pages.

International Search Report and Written Opinion for International Application No. PCT/US2020/017261, mailed May 14, 2020, 13 pages.

Office Action for Canadian Application No. 3101972, mailed May 13, 2025, 4 pages.

Office Action for Chinese Application No. 202080025953.7, mailed May 24, 2025, with English language translation, 12 pages.

Office Action for Chinese Application No. 202310257287.5, mailed Apr. 23, 2025, with English translation, 21 pages.

Office Action for Ex Parte Re-examination of U.S. Appl. No. 90/019,756, mailed Jun. 17, 2025, 38 pages.

Office Action for Ex Parte Re-examination of U.S. Appl. No. 90/019,757, mailed Jun. 17, 2025, 27 pages.

Office Action for Israeli Application No. 313917, mailed May 29, 2025, 4 pages.

Office Action for Japanese Application No. 2024-014849, mailed Apr. 30, 2025, with English translation, 9 pages.

Office Action for Japanese Application No. 2024-115518, mailed Jun. 11, 2025, with English Translation, 6 pages.

Office Action for Japanese Application No. 2024-187934, mailed Apr. 28, 2025, with English translation, 12 pages.

Office Action for U.S. Appl. No. 16/785,170, mailed Sep. 14, 2022, 11 pages.

Appellant/Patent Owner (Magnolia's) Opening Brief on Appeal, *Magnolia Medical Technologies, Inc. v. Kurin, Inc.*; Appeal No. 24-2001 (Fed. Cir.); from C.A. 19-00097-CFC-CJP (D. Del.), dated Aug. 26, 2024, Document 10, 71 pages.

Appellant/Patent Owner (Magnolia's) Reply Brief on Appeal, *Magnolia Medical Technologies, Inc. v. Kurin, Inc.*; Appeal No. 24-2001 (Fed. Cir.); from C.A. 19-00097-CFC-CJB (D. Del.), dated Jan. 7, 2025, Document 25, 44 pages.

Appellee/Requester (Kurin's) Brief on Appeal, *Magnolia Medical Technologies, Inc. v. Kurin, Inc.*; Appeal No. 24-2001 (Fed. Cir.); from C.A. 19-00097-CFC-CJB (D. Del.), dated Nov. 12, 2024, Document 21, 89 pages.

Judgment in favor of Kurin, Inc. against Magnolia Medical Technologies, Inc.; C.A. 19-00097-CFC-CJB (D. Del.), dated Jun. 10, 2024; Exhibit 1026, 3 pages.

Memorandum Opinion (concerning claim construction) in Magnolia Medical Technologies, Inc. v. Kurin, Inc .; C.A. 1:19-cv-00097-CFC-CJB (D. Del.), dated May 20, 2020, Exhibit 1030, 14 pages.

Office Action for U.S. Appl. No. 17/902,207, mailed Jul. 24, 2025, 15 pages.

Order Granting Kurin's Motion for Judgment of Non-Infringement as a Matter of Law; C.A. 19- 00097-CFC-CJB (D. Del.), dated May 14, 2024, Exhibit 1024, 2 pages.

Patent Trial and Appeal Board Decision in Ex Parte Reexamination U.S. Appl. No. 90/019,177, dated May 20, 2025, Exhibit 1003, 22 pages.

Request for Ex Parte Reexamination for U.S. Patent No. U.S. Pat. No. 10,039,483 Under 35 U.S.C. § 302 and 37 C.F.R. § 1.510, filed Jul. 21, 2025, 66 pages.

Office Action for European Application No. 23182529.0, mailed Jul. 29, 2025, 6 pages.

Office Action for Israeli Application No. 286263, mailed Aug. 5, 2025, 3 pages.

Office Action for U.S. Appl. No. 17/516,887, mailed Aug. 13, 2025, 24 pages.

Office Action for U.S. Appl. No. 19/175,765, mailed Aug. 8, 2025, 11 pages.

Partial Judgment of Infringement of U.S. Appl. No. 10/039,483, Document 512 (Exhibit 1022), *Magnolia Medical Technologies, Inc. v. Kurin, Inc.*, C.A. 19-00097-CFC-CJB (D. Del.), dated Jul. 26, 2023, 2 pages.

AU Application No. 2020234829, Office Action mailed Sep. 11, 2025; Applicant Magnolia Medical Technologies, Inc.; 3 pages.

AU Application No. 2024205062, Office Action mailed Sep. 8, 2025; Applicant Magnolia Medical Technologies, Inc.; 2 pages.

Becton, Dickinson and Company "Bd Bactec™ Blood Culture System," [Retrieval Date Unknown] available online URL:https://www.bd.com/en-US/products-and-solutions/products/product-families/bd-bactec-blood-culture-system; 9 pages (Publication Date Unknown).

Buzard, B.A., et al.; "Evaluation of an Initial Specimen Diversion Device (ISDD) on Rates of Blood Culture Contamination in the Emergency Department," Jun. 22, 2020; Kans J Med.; 14(1):73-76 (Mar. 19, 2021).

Biomerieux "Bact/Alert® Culture Media: Strong Outside, Strong Inside," PRN 054364 Rev.01A; [Online Retrieval Date Unknown]; URL: https://www.biomerieux.com/US/en/our-offer/clinical-products/bact-alert-culture-media-bottles.html; 10 pages (Publication Date Unknown ).

CA Application No. 3132981, Office Action mailed Aug. 22, 2025; Applicant Magnolia Medical Technologies, Inc .; 5 pages.

Callado, G.Y., et al.; "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis.; 10(9):ofad433; pp. 1-10. doi: 10.1093/ofid/ofad433 (Aug. 11, 2023).

CN Application No. 201811146373.4, Office Action mailed Jul. 28, 2025; Applicant Magnolia Medical Technologies, Inc., with English Translation; 36 pages.

Declaration of Dr. Morten Jensen under 37 C.F.R. § 1.132, U.S. Pat. No. 10,052,053; dated Oct. 1, 2025, 79 pages.

Declaration of Dr. Morten Jensen under 37 C.F.R. § 1.132, U.S. Pat. No. 11,529,081, dated Nov. 25, 2025, 75 pages.

Declaration of Dr. Morten Jensen under 37 C.F.R. 1.132, U.S. Pat. No. 9,855,002; dated Oct. 1, 2025, 61 pages.

ENA (Emergency Nurses Association) "Clinical Practice Guideline: Synopsis—Prevention of Blood Culture Contamination," last updated Jan. 9, 2023 [Retrieval Date Unknown] accessed online URL:https://www.guidelinecentral.com/guideline/308349/#section-420; 1 page (May 8, 2018).

EP Application No. 25164992.7, Extended European Search Report mailed Aug. 26, 2025; Applicant Magnolia Medical Technologies, Inc.; 8 pages.

IL Application No. 309638, Office Action mailed Aug. 11, 2025; Applicant Magnolia Medical Technologies, Inc et al.; 3 pages. (English Only).

Joint Claim Construction Brief for Kurin, Inc's Asserted Patent of U.S. Pat. Nos. 12,138,052, Document 153; *Magnolia Medical Technologies, Inc. v. Kurin, Inc.*, C.A. 1:24-cv- 01124-CFC (D. Del.); filed Mar. 10, 2025; 31 pages.

Joint Motion for Entry of Partial Judgment of Non-Infringement of U.S. Pat. Nos. 9,855,002 and 10,052,053, with Proposed Partial Judgment, Document 247; *Magnolia Medical Technologies, Inc. v. Kurin, Inc.*, C.A. 1:24-cv-01124-CFC (D. Del.); filed Jul. 25, 2025, 7 pages.

(56) References Cited

OTHER PUBLICATIONS

JP Application No. 2022-184274, Office Action Appeal Decision No. 2024-016403 mailed Nov. 7, 2025, Applicant Magnolia Medical Technologies, Inc., with English translation; 73 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Sep. 5, 2025; Applicant Magnolia Medical Technologies, Inc., with English Translation; 10 pages.
KURIN "Changing Blood Culture Collection in Hospitals Across America, Clinical Evidence, Studies" [Retrieved online Sep. 15, 2025] URL:https://www.kurin.com/studies/; 22 pages (Publication Date Unknown).
Kurin "Changing Blood Culture Collection in Hospitals Across America," [Retrieved online Sep. 15, 2025] URL:https://www.kurin.com/clinical-guidelines/; 11 pages (Publication Date Unknown).
Kurin "False Positive Blood Cultures—Improve the accuracy of blood culture," [Retrieved online Sep. 15, 2025] URL:https://www.kurin.com/false-positive-blood-cultures/; 5 pages (Publication Date Unknown).
Kurin "Kurin® Jet™ Blood Culture Collection Ordering Information," Brochure [Retrieval Date Unknown] available online URL: https://www.kurin.com/kurin-jet/ 2 pages (Publication Date Unknown).
Kurin "Kurin Launches Kurin Jet, Redefining the Blood Culture Contamination Device Market," [Retrieval Date Unknown] URL:https://www.kurin.com/kurin-launches-kurin-jet-redefining-the-blood-culture-contamination-device-market/; 5 pages (Publication Date Unknown).
Kurin "Kurin Lock® with Flash Technology: Better than conventional diversion," [Retrieved online Sep. 26, 2025] URL:https://www.kurin.com/kurin-jet/; 10 pages (Publication Date Unknown).
Kurin "Lowering the 3% Blood Culture Contamination Rate Benchmark," [Retrieved online Sep. 15, 2025] URL:https://www.kurin.com/3-percent-standard/; 4 pages (Publication Date Unknown).
Kurin "The Financial and Clinical Costs of False Positive Blood Cultures," [Retrieved online Sep. 15, 2025] URL:https://www.kurin.com/false-positives-blood-culture-cost/; 5 pages (Publication Date Unknown).
Magnolia Medical Technologies, Inc.; "Newly Released CLSI National Blood Culture Guidelines Identify Best Practices and Evidence-Based Technology Solutions Such as Steripath® to Improve Patient Safety and Outcomes," [Retrieved online Sep. 15, 2025] URL: https://magnolia-medical.com/news/newly-released-clsi-national-blood-culture-guidelines-identify-best-practices-and-evidence-based-technology-solutions-such-as-steripath-to-improve-patient-safety-and-outcomes/; 5 pages (May 5, 2022).
Mohajer, M.A., et al.; "The Impact of Initial Specimen Diversion Systems on Blood Culture Contamination," Open Forum Infect Dis .; 10(5):ofad182; pp. 1-6. doi: 10.1093/ofid/ofad182 (Apr. 5, 2023).
Order *Magnolia Medical Technologies, Inc.*, v. *Kurin, Inc.*, C.A. No. 1:24-cv-01124-CFC (D. Del.); Document 390, dated Nov. 17, 2025; 6 pages.
Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012.06.007, 13 pages (Sep. 2012).
U.S. Appl. No. 17/591,237, Final Office Action mailed Aug. 20, 2025; Inventor Bullington, Gregory J et al.; 24 pages.
U.S. Appl. No. 18/242,900, Non-Final Office Action mailed Oct. 23, 2025; Inventor Bullington, Gregory J et al.; 12 pages.
U.S. Appl. No. 18/680,331, Final Office Action mailed Nov. 24, 2025; Inventor Bullington, Gregory J et al.; 9 pages.
U.S. Appl. No. 18/680,348, Final Office Action mailed Nov. 24, 2025; Inventor Bullington; Gregory J et al.; 8 pages.
U.S. Appl. No. 18/680,377, Final Office Action mailed Nov. 25, 2025; Inventor Bullington, Gregory J., et al.; 14 pages.
U.S. Appl. No. 18/680,439, Final Office Action mailed Nov. 25, 2025; Inventor Bullington, Gregory J., et al.; 10 pages.

U.S. Appl. No. 18/680,466, Final Office Action mailed Aug. 20, 2025; Inventor Bullington, Gregory J. et al.; 10 pages.
U.S. Appl. No. 19/175,765, Final Office Action mailed Nov. 26, 2025; Inventor Bullington, Gregory J. et al.; 14 pages.
U.S. Appl. No. 90/015,399, Order Granting Request for Ex Parte Reexamination mailed Oct. 21, 2025; Inventor Bullington, Gregory J., et al.; 43 pages.
U.S. Appl. No. 90/019,756, Ex Parte Reexamination Interview Summary mailed Sep. 17, 2025, Inventor Patton, Richard G.; 7 pages.
U.S. Appl. No. 90/019,756, Ex Parte Reexamination Non-Final Action mailed Nov. 10, 2025; Inventor Patton, Richard G.; 44 pages.
U.S. Appl. No. 90/019,757, Ex Parte Reexamination Final Action mailed Nov. 28, 2025; Inventor Patton, Richard G.; 46 pages.
U.S. Appl. No. 90/019,757, Ex Parte Reexamination Interview Summary mailed Sep. 17, 2025, Inventor Patton, Richard G.; 7 pages.
U.S. Appl. No. 90/019,823, Ex Parte Reexamination Interview Summary mailed Nov. 25, 2025; Inventor Bullington, Gregory J.; 31 pages.
U.S. Appl. No. 90/019,823, Ex-Parte Reexamination mailed Aug. 25, 2025; Inventor Bullington, Gregory J. et al.; 30 pages.
U.S. Appl. No. 90/019,823, Response to Office Action in Ex Parte Reexamination filed Nov. 25, 2025; Inventor Bullington, Gregory J.; 211 pages.
U.S. Appl. No. 90/019,824, Ex Parte Reexamination Non-Final Action mailed Nov. 4, 2025; Inventor Bullington, Gregory J., et al.; 22 pages.
U.S. Appl. No. 90/019,825, Ex Parte Reexamination Non-Final Action mailed Nov. 17, 2025; Inventor Bullington, Gregory J., et al.; 25 pages.
Valleywise Health Medical Center Case Study "In anticipation of CMS changes, AZ hospital identifies solution to blood culture contaminations with new Kurin Jet™," Brochure; 1 page (Publication Date Unknown).
Widmer, A.F., et al.; "Sterilization of skin and catheters before drawing blood cultures," J Clin Microbiol .; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).
Zwang, O., et al.; "Analysis of strategies to improve cost effectiveness of blood cultures," J Hosp Med.; 1(5):272-276. doi: 10.1002/jhm.115 (Sep. 2006).
AU Application No. 2013267448, Office Action mailed Nov. 5, 2016; Applicant Magnolia Medical Technologies, Inc.; 3 pages.
AU Application No. 2017216493, Office Action mailed Sep. 19, 2018; Applicant Magnolia Medical Technologies, Inc.; 2 pages.
AU Application No. 2019204941, Office Action mailed Jul. 15, 2019; Applicant Magnolia Medical Technologies, Inc.; 4 pages.
AU Application No. 2020213415, Office Action mailed May 21, 2021; Applicant Magnolia Medical Technologies, Inc.; 3 pages.
CA Application No. 2875118, Office Action mailed Apr. 7, 2020; Applicant Magnolia Medical Technologies, Inc et al.; 4 pages.
CA Application No. 2875118, Office Action mailed Mar. 21, 2019; Applicant Magnolia Medical Technologies, Inc et al.; 5 pages.
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 2932536, Office Action mailed Jul. 13, 2021; Applicant Magnolia Medical Technologies, Inc.; 4 pages.
CN Application No. 201380040468.7, Office Action mailed Apr. 12, 2017; Applicant Magnolia Medical Technologies, Inc., with English Translation; 8 pages.
CN Application No. 201380071681.4, Office Action mailed Aug. 16, 2016; Applicant Magnolia Medical Technologies, Inc., with English Translation; 16 pages.
CN Application No. 201380071681.4, Office Action mailed Jun. 28, 2017; Applicant Magnolia Medical Technologies, Inc., with English Translation; 22 pages.

(56)           References Cited

OTHER PUBLICATIONS

CN Application No. 201711078173.5, Office Action mailed Feb. 3, 2020; Applicant Magnolia Medical Technologies, Inc., with English Translation; 14 pages.
CN Application No. 201880088771.7, Office Action mailed May 7, 2022; Applicant Magnolia Medical Technologies, Inc., with English Translation; 5 pages.
CN Application No. 202011295348.X, Office Action mailed Nov. 29, 2023; Applicant Magnolia Medical Technologies, Inc., with English Translation; 10 pages.
CN Application No. 202080094860.X, Office Action mailed Jan. 10, 2025; Applicant Magnolia Medical Technologies, Inc., with English Translation; 20 pages.
EP Application No. 13859067.4, Extended European Search Report mailed Aug. 16, 2017; Applicant Magnolia Medical Technologies, Inc.; 6 pages.
EP Application No. 13859067.4, Extended European Search Report mailed Jan. 27, 2017; Applicant Magnolia Medical Technologies, Inc.; 4 pages.
EP Application No. 13859067.4, Extended European Search Report mailed Jun. 7, 2016; Applicant Magnolia Medical Technologies, Inc.; 4 pages.
EP Application No. 16200112.7, Extended European Search Report mailed Feb. 15, 2018; Applicant Magnolia Medical Technologies, Inc.; 3 pages.
EP Application No. 16200112.7, Extended European Search Report mailed Mar. 1, 2017; Applicant Magnolia Medical Technologies, Inc.; 6 pages.
EP Application No. 16843182.3, Extended European Search Report mailed Mar. 26, 2019; Applicant Magnolia Medical Technologies, Inc.; 4 pages.
EP Application No. 18813278.1, Extended European Search Report mailed Feb. 17, 2021; Applicant Magnolia Medical Technologies, Inc.; 4 pages.
EP Application No. 20167572.5, Extended European Search Report mailed Sep. 30, 2020; Applicant Magnolia Medical Technologies, Inc.; 10 pages.
EP Application No. 23173044.1, Extended European Search Report mailed Oct. 27, 2023; Applicant Magnolia Medical Technologies, Inc.; 8 pages.
GB Application No. 1506837.2, Office Action mailed Jul. 19, 2017; Applicant Magnolia Medical Technologies, Inc.; 6 pages.
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 273025, Office Action mailed Dec. 4, 2022; Applicant Magnolia Medical Technologies, Inc et al., with English Translation; 6 pages.
IL Application No. 303591, Office Action mailed Feb. 25, 2024; Applicant Magnolia Medical Technologies, Inc et al.; 4 pages.
IN Application No. 11068/DELNP/2014, Office Action mailed Sep. 28, 2020; Applicant Magnolia Medical Technologies, Inc., with English Translation; 6 pages.
JP Application No. 2015-515178, Office Action mailed Feb. 16, 2017; Applicant Magnolia Medical Technologies, Inc et al., with English Translation; 7 pages.
JP Application No. 2015-545494, Office Action mailed Jun. 19, 2017; Applicant Magnolia Medical Technologies, Inc., with English Translation; 9 pages.
JP Application No. 2017-214629, Office Action mailed Jul. 23, 2019; Applicant Magnolia Medical Technologies, Inc., with English Translation; 8 pages.
JP Application No. 2017-214629, Office Action mailed Sep. 20, 2018; Applicant Magnolia Medical Technologies, Inc., with English Translation; 9 pages.

JP Application No. 2020-075727, Office Action mailed Mar. 28, 2023; Applicant Magnolia Medical Technologies, Inc., with English Translation; 6 pages.
JP Application No. 2020-075727, Office Action mailed May 18, 2022; Applicant Magnolia Medical Technologies, Inc., with English Translation; 11 pages.
JP Application No. 2020-566232, Office Action mailed Sep. 19, 2023; Applicant Magnolia Medical Technologies, Inc., with English Translation; 6 pages.
JP Application No. 2021-552145, Office Action mailed Sep. 11, 2024; Applicant Magnolia Medical Technologies, Inc., with English Translation; 4 pages.
JP Application No. 2022-074696, Office Action mailed Oct. 25, 2023; Applicant Magnolia Medical Technologies, Inc., with English Translation; 7 pages.
JP Application No. 2022-149585, Office Action mailed Sep. 26, 2023; Applicant Magnolia Medical Technologies, Inc., with English Translation; 9 pages.
JP Application No. 2022-212405, Office Action mailed Nov. 29, 2023; Applicant Magnolia Medical Technologies, Inc., with English Translation; 13 pages.
JP Application No. 2022-534220, Office Action mailed Sep. 13, 2024; Applicant Magnolia Medical Technologies, Inc., with English Translation; 8 pages.
PCT Application No. PCT/US2016/050380, International Search Report and Written Opinion mailed Dec. 1, 2016, Applicant Magnolia Medical Technologies, Inc.; 6 pages.
PCT Application No. PCT/US2020/064600, International Search Report and Written Opinion mailed Mar. 18, 2021, Applicant Magnolia Medical Technologies, Inc.; 14 pages.
U.S. Appl. No. 14/264,481, Final Office Action mailed Apr. 13, 2017; Inventor Bullington, Gregory J. et al.; 14 pages.
U.S. Appl. No. 14/264,481, Final Office Action mailed Jul. 14, 2016; Inventor Bullington, Gregory J. et al.; 9 pages.
U.S. Appl. No. 14/264,481, Non-Final Office Action mailed Feb. 26, 2016; Inventor Bullington, Gregory J. et al.; 10 pages.
U.S. Appl. No. 14/264,481, Non-Final Office Action mailed Jul. 1, 2015; Inventor Bullington, Gregory J. et al.; 13 pages.
U.S. Appl. No. 14/264,481, Non-Final Office Action mailed Oct. 21, 2016; Inventor Bullington, Gregory J. et al.; 10 pages.
U.S. Appl. No. 14/264,481, Non-Final Office Action mailed Sep. 7, 2017; Inventor Bullington, Gregory J. et al.; 12 pages.
U.S. Appl. No. 14/712,431, Non-Final Office Action mailed Sep. 14, 2018; Inventor Bullington, Gregory et al.; 10 pages.
U.S. Appl. No. 14/728,318, Final Office Action mailed Dec. 20, 2018; Inventor Bullington, Gregory J. et al.; 26 pages.
U.S. Appl. No. 14/728,318, Final Office Action mailed Jan. 8, 2018; Inventor Bullington, Gregory J. et al.; 36 pages.
U.S. Appl. No. 14/728,318, Non-Final Office Action mailed May 19, 2017; Inventor Bullington, Gregory J. et al.; 26 pages.
U.S. Appl. No. 14/880,397, Final Office Action mailed Sep. 24, 2018; Inventor Bullington, Gregory J. et al.; 5 pages.
U.S. Appl. No. 14/880,397, Non-Final Office Action mailed Apr. 17, 2018; Inventor Bullington, Gregory J. et al.; 6 pages.
U.S. Appl. No. 15/257,185, Non-Final Office Action mailed Aug. 8, 2017; Inventor Bullington, Gregory J. et al.; 5 pages.
U.S. Appl. No. 15/925,159, Final Office Action mailed May 14, 2019; Inventor Bullington, Gregory J. et al.; 13 pages.
U.S. Appl. No. 15/925,159, Non-Final Office Action mailed Nov. 26, 2018; Inventor Bullington, Gregory J. et al.; 11 pages.
U.S. Appl. No. 16/815,521, Non-Final Office Action mailed Oct. 25, 2023; Inventor Bullington, Gregory J. et al.; 9 pages.
U.S. Appl. No. 17/119,732, Non-Final Office Action mailed Aug. 25, 2022; Inventor Bullington, Gregory J. et al.; 30 pages.
U.S. Appl. No. 17/559,081, Non-Final Office Action mailed Jan. 12, 2026; Inventor Bullington, Gregory J. et al.; 10 pages.
U.S. Appl. No. 18/130,207, Non-Final Office Action mailed Aug. 21, 2023; Inventor Bullington, Gregory J. et al.; 7 pages.
U.S. Appl. No. 18/209,327, Non-Final Office Action mailed Dec. 16, 2025; Inventor Patton, Richard G.; 19 pages.
U.S. Appl. No. 18/243,540, Non-Final Office Action mailed Jun. 4, 2025; Inventor Bullington, Gregory J. et al.; 34 pages.

(56)         References Cited

OTHER PUBLICATIONS

U.S. Appl. No. 18/299,680, Non-Final Office Action mailed Aug. 15, 2023; Inventor Bullington, Gregory J. et al.; 5 pages.
U.S. Appl. No. 18/407,010, Non-Final Office Action mailed Dec. 4, 2025; Inventor Bullington, Gregory J. et al.; 7 pages.
U.S. Appl. No. 90/019,756, Order Granting Request for Ex Parte Reexamination mailed Jan. 22, 2025, Inventor Patton, Richard G.; 14 pages.
U.S. Appl. No. 90/019,757, Order Granting Request for Ex Parte Reexamination mailed Jan. 27, 2025, Inventor Patton, Richard G.; 15 pages.

* cited by examiner

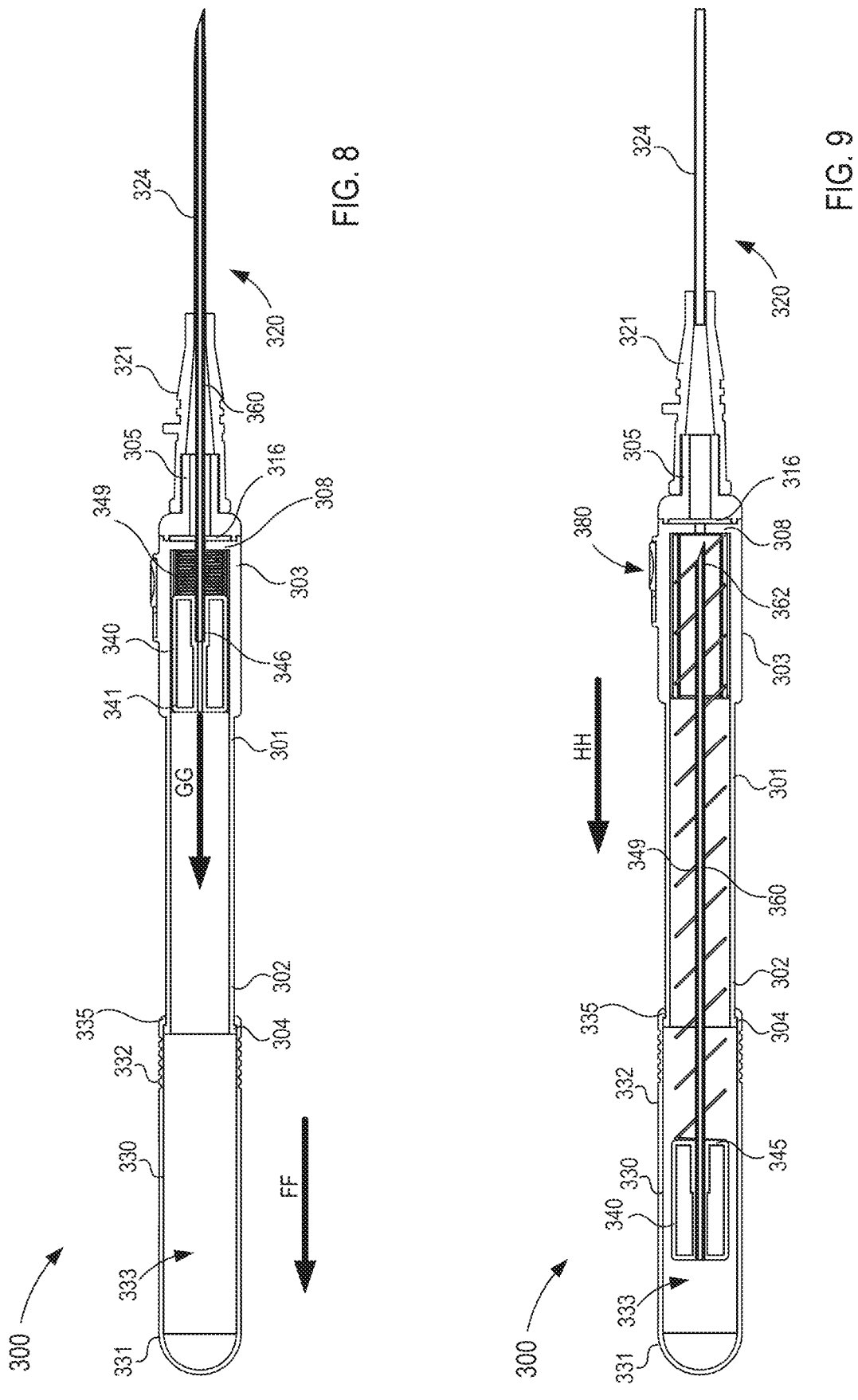

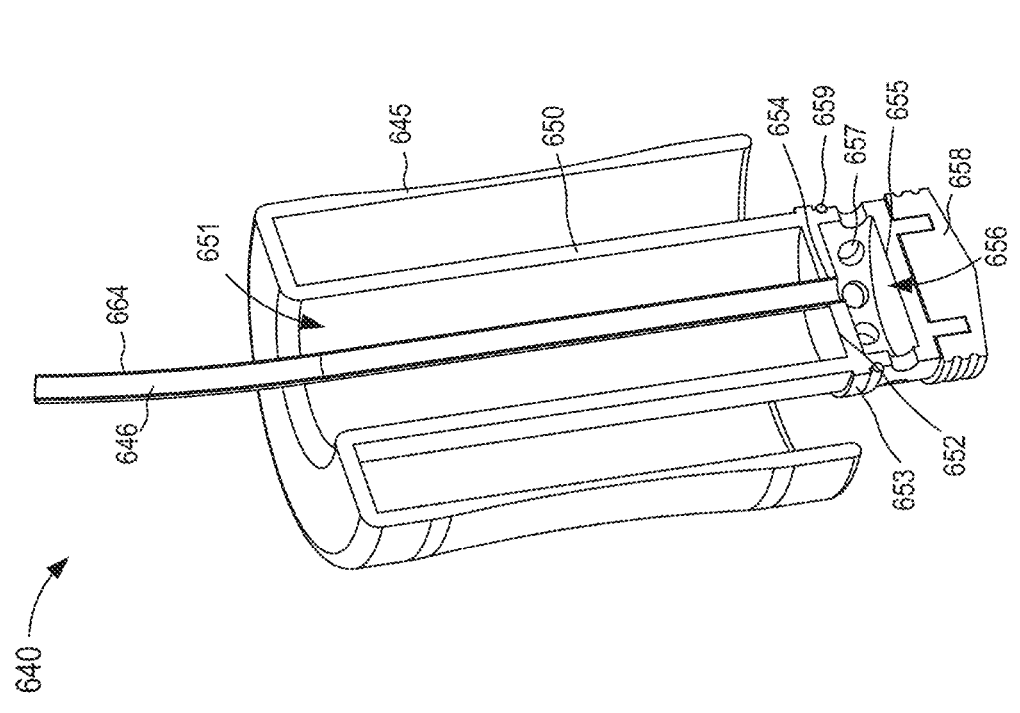
FIG. 27
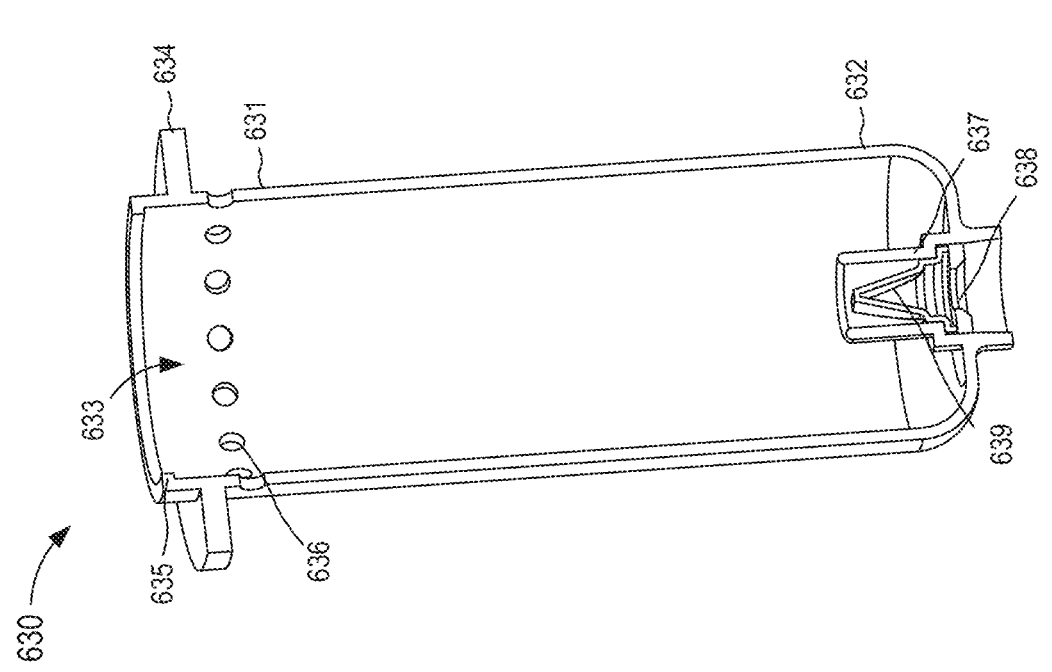
FIG. 26

600

800

813

815

814

812

802

806

846

807

WW

801

840

847

803

805

817

820

822

824

990 —

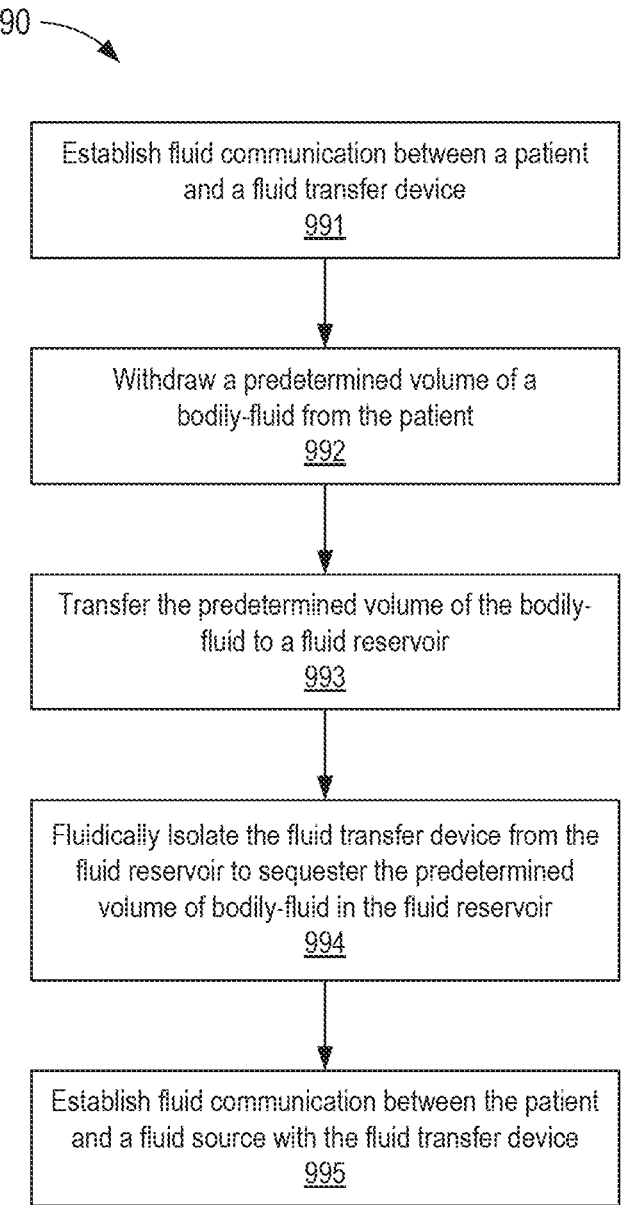

Establish fluid communication between a patient
and a fluid transfer device
991

Withdraw a predetermined volume of a
bodily-fluid from the patient
992

Transfer the predetermined volume of the bodily-
fluid to a fluid reservoir
993

Fluidically isolate the fluid transfer device from the
fluid reservoir to sequester the predetermined
volume of bodily-fluid in the fluid reservoir
994

Establish fluid communication between the patient
and a fluid source with the fluid transfer device
995

FIG. 40

SYSTEMS AND METHODS FOR DELIVERING A FLUID TO A PATIENT WITH REDUCED CONTAMINATION

CROSS-REFERENCE TO RELATED APPLICATIONS

This application is a continuation of U.S. patent application Ser. No. 18/931,922, filed Oct. 30, 2024, entitled, "Systems and Methods for Delivering a Fluid to a Patient with Reduced Contamination," which is a continuation of U.S. patent application Ser. No. 18/399,007, filed Dec. 28, 2023, now U.S. Pat. No. 12,133,968, entitled, "Systems and Methods for Delivering a Fluid to a Patient with Reduced Contamination," which is a continuation of U.S. patent application Ser. No. 16/789,034, filed Feb. 12, 2020, now U.S. Pat. No. 11,890,452, entitled, "Systems and Methods for Delivering a Fluid to a Patient with Reduced Contamination," which is a continuation of U.S. patent application Ser. No. 16/255,055, filed Jan. 23, 2019, now U.S. Pat. No. 10,596,315, entitled, "Systems and Methods for Delivering a Fluid to a Patient with Reduced Contamination," which is a continuation of U.S. patent application Ser. No. 15/899,856, filed Feb. 20, 2018, now U.S. Pat. No. 10,220,139, entitled, "Systems and Methods for Delivering a Fluid to a Patient with Reduced Contamination," which is a continuation of U.S. patent application Ser. No. 14/838,794, filed Aug. 28, 2015, now U.S. Pat. No. 9,931,466, entitled, "Systems and Methods for Delivering a Fluid to a Patient with Reduced Contamination," which is a divisional of U.S. patent application Ser. No. 14/049,326, filed Oct. 9, 2013, now U.S. Pat. No. 9,149,576, entitled, "Systems and Methods for Delivering a Fluid to a Patient with Reduced Contamination," which claims priority to and the benefit of U.S. Provisional Patent Application No. 61/712,468, filed Oct. 11, 2012, entitled, "Systems and Methods for Delivering a Fluid to a Patient with Reduced Contamination," the disclosures of which are incorporated herein by reference in their entireties.

BACKGROUND

Embodiments described herein relate generally to delivering a fluid to a patient, and more particularly to devices and methods for delivering a parenteral fluid to a patient with reduced contamination from microbes or other contaminants exterior to the body and/or the fluid source, such as dermally residing microbes.

Human skin is normally habituated in variable small amounts by certain bacteria such as coagulase-negative *Staphylococcus* species, *Propionibacterium acnes, Micrococcus* species, Streptococci *Viridans* group, *Corynebacterium* species, and *Bacillus* species. These bacteria for the most part live in a symbiotic relationship with human skin but in some circumstances can give rise to serious infections in the blood stream known as septicemia. Septicemia due to these skin residing organisms is most often associated with an internal nidus of bacterial growth at the site of injured tissue, for example a damaged, scarred heart valve, or a foreign body (often an artificial joint, vessel, or valve). Furthermore, there are predisposing factors to these infections such as malignancy, immunosuppression, diabetes mellitus, obesity, rheumatoid arthritis, psoriasis, and advanced age. In some instances, these infections can cause serious illness and/or death. Moreover, these infections can be very expensive and difficult to treat and often can be associated with medical related legal issues.

In general medical practice, blood is drawn from veins (phlebotomy) for two main purposes; (1) donor blood in volumes of approximately 500 mL is obtained for the treatment of anemia, deficient blood clotting factors including platelets and other medical conditions; and (2) smaller volumes (e.g., from a few drops to 10 mL or more) of blood are obtained for testing purposes. In each case, whether for donor or testing specimens, a fluid communicator (e.g., catheter, cannula, needle, etc.) is used to penetrate and enter a vein (known as venipuncture) enabling withdrawing of blood into a tube or vessel apparatus in the desired amounts for handling, transport, storage and/or other purposes. The site of venipuncture, most commonly the antecubital fossa, is prepared by cleansing with antiseptics to prevent the growth of skin residing bacteria in blood withdrawn from the vein. It has been shown venipuncture needles dislodge fragments of skin including hair and sweat gland structures as well as subcutaneous fat and other adnexal structures not completely sterilized by skin surface antisepsis. These skin fragments can cause septicemia in recipients of donor blood products, false positive blood culture tests and other undesirable outcomes. Furthermore, methods, procedures and devices are in use, which divert the initial portion of venipuncture blood enabling exclusion of these skin fragments from the venipuncture specimen in order to prevent septicemia in recipients of donor blood products, false positive blood culture tests and other undesirable outcomes.

Venipuncture is also the most common method of accessing the blood stream of a patient to deliver parenteral fluids into the blood stream of patients needing this type of medical treatment. Fluids in containers are allowed to flow into the patient's blood stream through tubing connected to the venipuncture needle or through a catheter that is placed into a patient's vasculature (e.g. peripheral IV, central line, etc.). During this process, fragments of incompletely sterilized skin can be delivered into the blood stream with the flow of parenteral fluids and/or at the time of venipuncture for introduction and insertion of a peripheral catheter. These fragments are undesirable in the blood stream and their introduction into the blood stream of patients (whether due to dislodging of fragments by venipuncture needle when inserting a catheter or delivered through tubing attached to needle or catheter) is contrary to common practices of antisepsis. Further, these microbes can be associated with a well-known phenomenon of colonization by skin residing organisms of the tubing and tubing connectors utilized to deliver parenteral fluids. The colonization is not typically indicative of a true infection but can give rise to false positive blood culture tests, which may result in unnecessary antibiotic treatment, laboratory tests, and replacement of the tubing apparatus with attendant patient risks and expenses. Furthermore, the risk of clinically significant serious infection due to skin residing organisms is increased.

As such, a need exists for improved fluid transfer devices, catheter introduction techniques and devices, as well as methods for delivering a parenteral fluid to a patient that reduce microbial contamination and inadvertent injection of undesirable external microbes into a patient's blood stream.

SUMMARY

Devices and methods for delivering a fluid to a patient and/or introducing a peripheral catheter with reduced contamination from dermally residing microbes or other contaminants exterior to the body and/or an external fluid source are described herein. In some embodiments, an apparatus includes a cannula assembly, a housing, a fluid reservoir, a flow control mechanism, and an actuator. The housing has a proximal end portion and a distal end portion and defines an inner volume therebetween. The housing includes an inlet port removably coupled to the cannula assembly. The fluid reservoir is fluidically coupled to the housing and configured to receive and isolate a first volume of bodily fluid withdrawn from a patient. The flow control mechanism is at least partially disposed in the inner volume and is configured to move relative to the housing between a first configuration and a second configuration. The flow control mechanism defines a fluid flow path between the cannula assembly and the fluid reservoir in the first configuration. The actuator is operably coupled to the flow control mechanism to move the flow control mechanism from the first configuration, in which the inlet port is placed in fluid communication the fluid reservoir such that bodily fluid can flow from the cannula assembly, through the inlet port via the fluid flow path and to the fluid reservoir, to the second configuration, in which the fluid reservoir is fluidically isolated from the cannula assembly.

BRIEF DESCRIPTION OF THE DRAWINGS

FIGS. 8 and 9 are cross-sectional views of the fluid transfer device taken along the line $X_1$-$X_1$ in FIG. 4, in a second and third configuration, respectively.

FIG. 26 is a cross-sectional perspective view of a fluid reservoir included in the fluid transfer device taken along the line $X_7$-$X_7$ in FIG. 25.

FIG. 27 is a cross-sectional perspective view of a flow control mechanism included in the fluid transfer device taken along the line $X_8$-$X_8$ in FIG. 25.

FIG. 40 is a flowchart illustrating a method of delivering a fluid to a patient using a fluid transfer device according to an embodiment.

DETAILED DESCRIPTION

Figure 1:
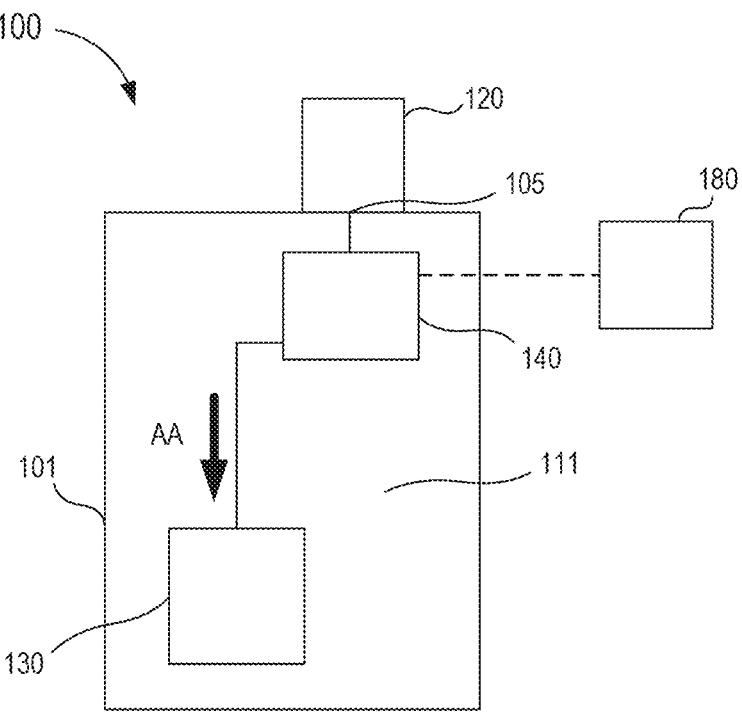
FIGS. 1 and 2 are schematic illustrations of a fluid transfer device according to an embodiment.

Devices and methods for delivering a fluid to a patient with reduced contamination from dermally residing microbes or other contaminants exterior to the body are described herein. In some embodiments, an apparatus includes a cannula assembly, a housing, a fluid reservoir, a flow control mechanism, and an actuator. The housing has a proximal end portion and a distal end portion and defines an inner volume therebetween. The housing includes an inlet port configured to be removably coupled to the cannula assembly. The fluid reservoir is fluidically coupled to the housing and configured to receive and isolate a first volume of bodily fluid withdrawn from a patient. The flow control mechanism is at least partially disposed in the inner volume and is configured to move relative to the housing between a first configuration and a second configuration. The flow control mechanism defines a fluid flow path between the cannula assembly and the fluid reservoir in the first configuration. The actuator is operably coupled to the flow control mechanism to move the flow control mechanism from the first configuration, in which the inlet port is placed in fluid communication the fluid reservoir such that bodily fluid can flow from the cannula assembly, through the inlet port via the fluid flow path and to the fluid reservoir, to the second configuration, in which the fluid reservoir is fluidically isolated from the cannula assembly.

In some embodiments, a device for delivering a fluid to a patient with reduced contamination includes a housing, a fluid reservoir, and a flow control mechanism. The housing has a proximal end portion and a distal end portion and defines an inner volume therebetween. The housing includes a first port configured to be removably coupled to a cannula assembly, and a second port configured to be fluidically coupled to a fluid source. The fluid reservoir is fluidically coupleable to the cannula assembly and configured to receive and isolate a predetermined volume of bodily fluid withdrawn from the patient. The flow control mechanism is at least partially disposed in the inner volume of the housing and is configured to move between a first configuration and a second configuration. When in the first configuration, the first port is placed in fluid communication with the fluid reservoir such that bodily fluid can flow from the cannula assembly, through the first port and to the fluid reservoir. When in the second configuration, the fluid reservoir is fluidically isolated from the cannula assembly and fluid can flow from the fluid source, in the second port, through the flow control mechanism, out the first port and to the cannula assembly.

In some embodiments, a method of delivering a fluid to a patient using a fluid transfer device includes establishing fluid communication between the patient and the fluid transfer device. Once in fluid communication, a predetermined volume of a bodily fluid is withdrawn from the patient. The predetermined volume of bodily fluid is transferred to a fluid reservoir. The fluid transfer device is fluidically isolated from the fluid reservoir to sequester the predetermined volume of bodily fluid in the fluid reservoir. The method further includes establishing fluid communication between the patient and a fluid source with the fluid transfer device.

In some embodiments, an apparatus includes a housing, a cannula assembly, a flow control mechanism, and a fluid reservoir. The flow control mechanism is configured to move relative to the housing between a first configuration and a second configuration. The cannula assembly is coupled to the housing and fluidically coupled to the fluid reservoir when the flow control mechanism is in the first configuration. The fluid reservoir is fluidically isolated from the cannula assembly when the flow control mechanism is in a second configuration such that the cannula assembly can be fluidically coupled to an external fluid reservoir and/or an external fluid source.

As referred to herein, "bodily fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

Figure 2:
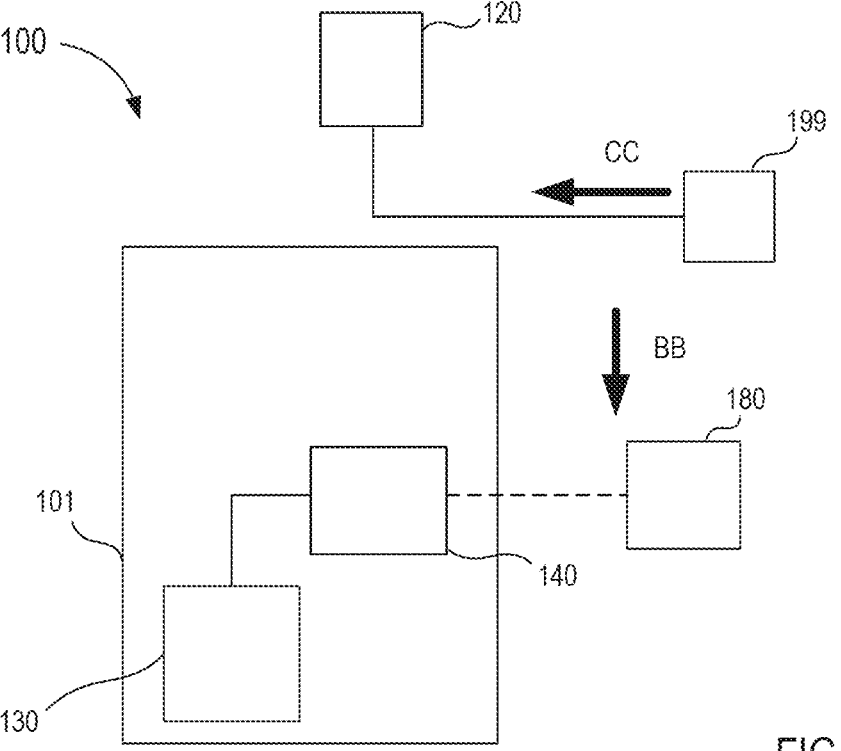

FIGS. 1 and 2 are schematic illustrations of a fluid transfer device 100 according to an embodiment, in a first and second configuration, respectively. Generally, the fluid transfer device 100 (also referred to herein as "transfer device") is configured to facilitate the insertion of a piercing member (e.g., a needle, a trocar, a cannula, or the like) into a patient to withdrawal and isolate a predetermined amount of bodily fluid from the patient containing, for example, dermally residing microbes. The fluid transfer device 100 is further configured to facilitate the delivery of parenteral fluid to the patient that does not substantially contain, for example, the dermally residing microbes. In other words, the transfer device 100 is configured to transfer and fluidically isolate the predetermined amount of bodily fluid, including dermally residing microbes dislodged from a venipuncture, within a collection reservoir and deliver parenteral fluids to the patient that are substantially free from the dislodged dermally residing microbes and/or other undesirable external contaminants.

The transfer device 100 includes a housing 101, a cannula assembly 120, a fluid reservoir 130, a flow control mechanism 140, and an actuator 180. The housing 101 can be any suitable shape, size, or configuration and is described in further detail herein with respect to specific embodiments. As shown in FIG. 1, the housing 101 defines an inner volume 111 that can movably receive and/or movably house at least a portion of the flow control mechanism 140, as described in further detail herein. A portion of the housing 101 can be, at least temporarily, physically and fluidically coupled to the cannula assembly 120. For example, in some embodiments, a distal end portion of the housing 101 can include an inlet port 105 or the like configured to physically and fluidically couple to a lock mechanism (not shown in FIGS. 1 and 2) included in the cannula assembly 120. In such embodiments, the lock mechanism can be, for example, a Luer-Lok® or the like that can engage the port. In some embodiments, the housing 101 can be monolithically formed with at least a portion of the cannula assembly 120. In other words, in some embodiments, the inlet port 105 can be monolithically formed with a portion of the cannula assembly 120 to define a fluid flow path between a portion of the housing 101 the cannula assembly 120. In this manner, a portion of the housing 101 can receive a bodily fluid from and/or deliver a parenteral fluid to a patient via a cannula included in the cannula assembly 120, as described in further detail herein.

The cannula assembly 120 can be any suitable configuration. For example, in some embodiments, the cannula assembly 120 includes an engagement portion and a cannula portion (not shown in FIGS. 1 and 2). In such embodiments, the engagement portion can physically and fluidically couple the cannula assembly 120 to the housing 101 (e.g., it can be the lock mechanism physically and fluidically coupled to the inlet port 105 as described above). The cannula portion can be configured to be inserted into a portion of a patient to deliver a fluid to or receive a fluid from the patient. For example, in some embodiments, the cannula portion can include a distal end with a sharp point configured to pierce a portion of the patient to dispose the cannula portion, at least in part, within a vein of the patient. In other embodiments, a piercing member (e.g., a lumen defining needle) can be movably disposed within the cannula assembly 120 to facilitate the insertion of the cannula portion 120 into the portion of the patient.

As shown in FIG. 1, the housing 101 can house and/or define the fluid reservoir 130. Similarly stated, in some embodiments, the fluid reservoir 130 can be disposed within and/or at least partially defined by the inner volume 111 of the housing 101. The fluid reservoir 130 can be configured to receive a predetermined amount of the bodily fluid and fluidically isolate the bodily fluid from a volume outside the fluid reservoir 130, as described in further detail herein. While shown in FIGS. 1 and 2 as being disposed within the inner volume 111 of the housing 101, in some embodiments, the fluid reservoir 130 can be disposed substantially outside the housing 101. In such embodiments, the fluid reservoir 130 can be physically and fluidically coupled to a portion of the housing 101. For example, in some embodiments, the fluid reservoir 130 can be coupled to an outlet port (not shown in FIGS. 1 and 2). In other embodiments, the fluid reservoir 130 can be operably coupled to the housing 101 via an intervening structure, such as, for example, a Luer-Lok® and/or flexible sterile tubing. In still other embodiments, the fluid reservoir 130 can be monolithically formed with at least a portion of the housing 101.

The flow control mechanism 140 included in the transfer device 100 is disposed, at least partially, within the inner volume 111 of the housing 101 and can be moved between a first configuration (FIG. 1) and a second configuration (FIG. 2). The flow control mechanism 140 can be any suitable mechanism configured to control or direct a flow of a fluid. For example, in some embodiments, the flow control mechanism 140 can include a valve (e.g., a check valve or the like) that allows a flow of a fluid in a single direction. In other embodiments, a valve can selectively control a flow of a fluid in multiple directions. In still other embodiments, the flow control mechanism 140 can define one or more lumens configured to selectively receive a flow of a fluid. In such embodiments, the flow control mechanism 140 can be moved relative to the housing 101 to selectively place a lumen in fluid communication with a portion of the transfer device 100 (e.g., the housing 101, the cannula assembly 120, and/or the fluid reservoir 130). For example, in some embodiments, a portion of the flow control mechanism 140 can be movably disposed, at least temporarily, within the cannula assembly 120 to selectively place the fluid reservoir 130 in fluid communication with the cannula assembly 120. In some embodiments, the portion of the flow control mechanism 140 can include a piercing member such as, for example, a needle configured to extend beyond a distal end of the cannula assembly 120 (not shown in FIGS. 1 and 2) to pierce the skin of a patient and facilitate the insertion of the cannula assembly 120 into a vein of the patient.

In some embodiments, the transfer device 100 can include an actuator 180 operably coupled to the flow control mechanism 140 and configured to move the flow control mechanism 140 between the first and the second configuration. For example, in some embodiments, the actuator 180 can be a push button, a slider, a toggle, a pull-tab, a handle, a dial, a lever, an electronic switch, or any other suitable actuator. In this manner, the actuator 180 can be movable between a first position corresponding to the first configuration of the flow control mechanism 140, and a second position, different from the first position, corresponding to the second configuration of the flow control mechanism 140. In some embodiments, the actuator 180 can be configured for uni-directional movement. For example, the actuator 180 can be moved from its first position to its second position, but cannot be moved from its second position back to its first position. In this manner, the flow control mechanism 140 is prevented from being moved to its second configuration before its first configuration, as described in further detail herein.

In use, the flow control mechanism 140 can be in the first configuration to place the fluid reservoir 130 in fluid communication with the cannula assembly 120, as indicated by the arrow AA in FIG. 1. In this manner, the fluid reservoir 130 can receive a flow of bodily fluid that can include dermally residing microbes dislodged during a venipuncture event (e.g., when the cannula assembly 120 and/or the flow control mechanism 140 pierces the skin of the patient). In some embodiments, the fluid reservoir 130 can be configured to receive a predetermined volume of the bodily fluid. With a desired amount of bodily fluid transferred to the fluid reservoir 130, a user (e.g., a doctor, physician, nurse, technician, phlebotomist, etc.) can manipulate the actuator 180 to move the flow control mechanism 140 from the first configuration to the second configuration. For example, the flow control mechanism 140 can be in the first configuration when the flow control mechanism 140 is in a distal position relative to the housing 101 (FIG. 1) and the actuator 180 can move the flow control mechanism 140 in a proximal direction relative to the housing 101 to place the flow control mechanism in the second configuration, as indicated by the arrow BB in FIG. 2. Moreover, when in the second configuration, the flow control mechanism 140 no longer facilitates the fluidic coupling of the fluid reservoir 130 to the cannula assembly 120. Thus, the fluid reservoir 130 is fluidically isolated from the cannula assembly 120.

While shown in FIGS. 1 and 2 as being moved in the proximal direction (e.g., in the direction of the arrow BB), in other embodiments, the actuator 180 can move the flow control mechanism 140 between the first configuration and the second configuration in any suitable manner or direction. For example, in some embodiments, the flow control mechanism 140 can be moved in a rotational motion between the first configuration and the second configuration. In other embodiments, the flow control mechanism 140 can be moved in a transverse motion (e.g., substantially perpendicular to the direction of the arrow BB). In such embodiments, the rotational or transverse motion can be such that the flow control mechanism 140 selectively defines one or more fluid flow paths configured to receive a fluid from a patient or to deliver a fluid to the patient, as described in further detail herein.

In some embodiments, the movement of the flow control mechanism 140 to the second configuration can substantially correspond to a physical and fluidic decoupling of at least a portion of the housing 101 from the cannula assembly 120 such that an external fluid reservoir 199 (e.g., also referred to herein as "fluid source") can be physically and fluidically coupled to the cannula assembly 120. For example, as shown in FIG. 2, in some embodiments, the housing 101 can be moved in the proximal direction (e.g., in the direction of the arrow BB) to be physically and fluidically decoupled from the cannula assembly 120. In some embodiments, the proximal movement of the flow control mechanism 140 urges the housing 101 to move in the proximal direction. In other embodiments, a user (e.g., a physician, phlebotomist, or nurse) can move the housing 101 in the proximal direction. In this manner, the external fluid reservoir 199 can be fluidically coupled to the cannula assembly 120. Expanding further, with the predetermined amount of bodily fluid transferred to the fluid reservoir 130, the external fluid reservoir 199 can be fluidically coupled to the cannula assembly 120 to deliver a flow of a parenteral fluid that is substantially free from dermally residing microbes dislodged during the venipuncture event, as indicated by the arrow CC in FIG. 2. Similarly stated, the dermally residing microbes that are dislodged during the venipuncture event can be entrained in the flow of the bodily fluid delivered to the fluid reservoir 130. Thus, when the flow control mechanism 140 is moved to the second configuration and the fluid reservoir 130 is fluidically isolated from the cannula assembly 120, the external fluid reservoir 199 can deliver the flow of parenteral fluid substantially free from dermally residing microbes.

Figure 3:
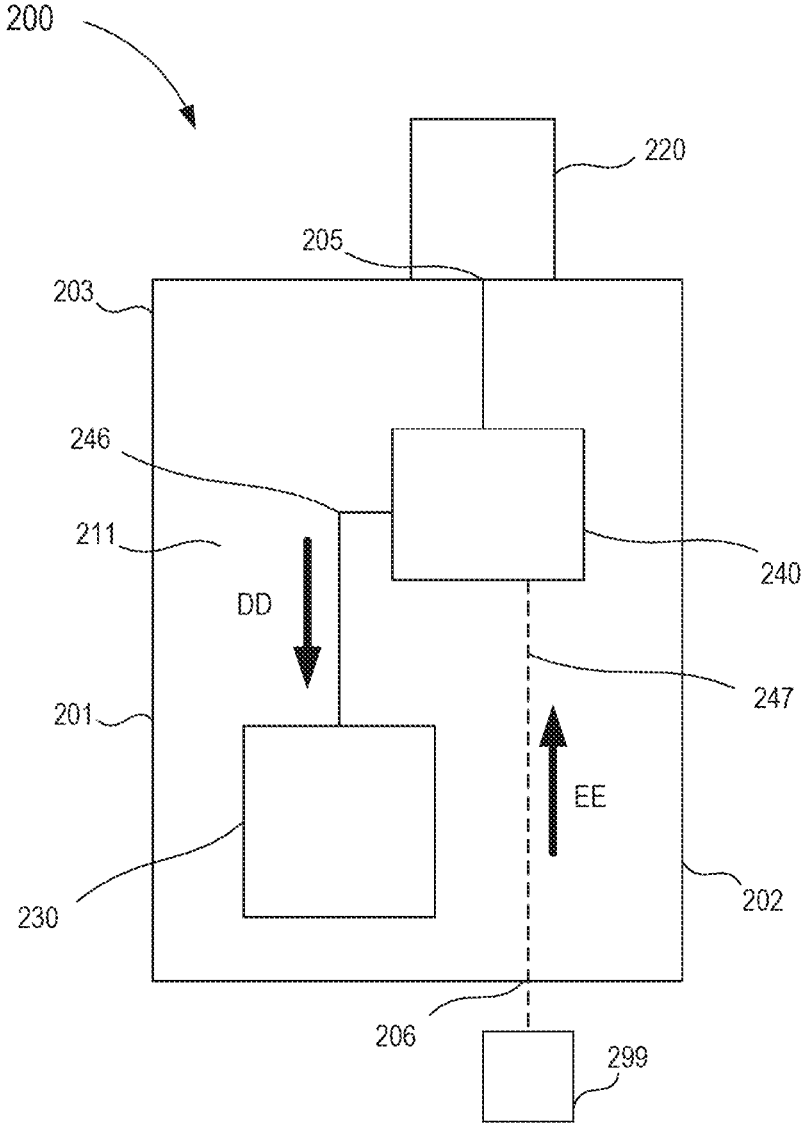
FIG. 3 is a schematic illustration of a fluid transfer device according to an embodiment.
Figure 4:
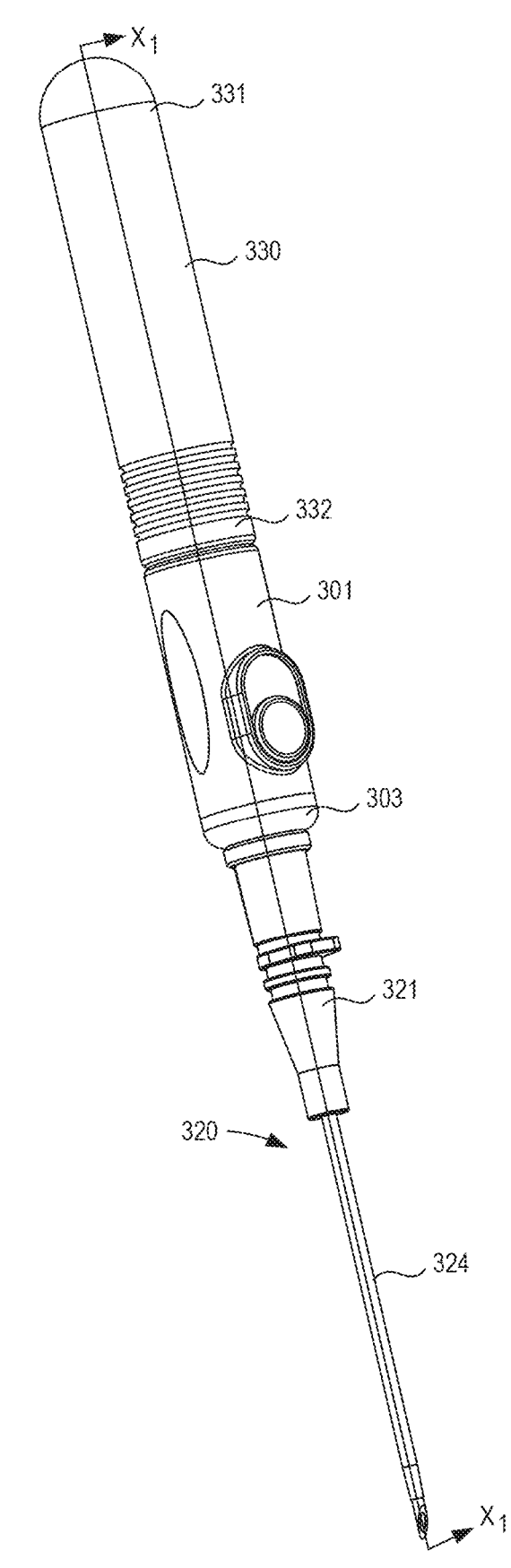
FIG. 4 is a perspective view of a fluid transfer device according to an embodiment.

While the housing 101 is shown in FIG. 2 as being moved in the proximal direction such that the external fluid reservoir 199 can be physically and fluidically coupled to the cannula assembly 120, in other embodiments, a housing need not be decoupled from a cannula assembly. For example, FIG. 3 is a schematic illustration of a transfer device 200 according to an embodiment. The transfer device 200 includes a housing 201, a cannula assembly 220, a fluid reservoir 230, and a flow control mechanism 240.

As shown in FIG. 3, the housing 201 includes a proximal end portion 202 and a distal end portion 203 and defines an inner volume 211 therebetween. The distal end portion 203 can be physically and fluidically coupled to the cannula assembly 220, as described above in reference to FIG. 1. For example, in some embodiments, the distal end portion 203 can include an inlet port 205 (also referred to herein as "first port") or the like that can be physically and fluidically coupled to the cannula assembly 220. The proximal end portion 202 includes an outlet port 206 (also referred to herein as "second port") that can be physically and fluidically coupled to an external fluid reservoir 299. The external fluid reservoir 299 can be any suitable fluid reservoir and can be coupled to the second port 206 via an adhesive, a resistance fit, a mechanical fastener, any number of mating recesses, a threaded coupling, and/or any other suitable coupling or combination thereof. For example, in some embodiments, the external fluid reservoir 299 can be substantially similar to known fluid reservoirs configured to deliver a parenteral fluid (e.g., a fluid source). In some embodiments, the external fluid reservoir 299 is monolithically formed with the second port 206. In still other embodiments, the external fluid reservoir 299 can be operably coupled to the second port 206 via an intervening structure (not shown in FIG. 3), such as, for example, a flexible sterile tubing. More particularly, the intervening structure can define a lumen configured to place the external fluid reservoir 299 in fluid communication with the second port 206.

The housing 201 can house or define at least a portion of the fluid reservoir 230. Similarly stated, the fluid reservoir 230 can be at least partially disposed within the inner volume 211 of the housing 201. The fluid reservoir 230 can receive and fluidically isolate a predetermined amount of the bodily fluid, as described above in reference to FIGS. 1 and 2. Similarly, the flow control mechanism 240 is at least partially disposed within the inner volume 211 of the housing 201 and can be moved between a first configuration and a second configuration. More specifically, the flow control mechanism 240 defines a first lumen 246 that fluidically couples the cannula assembly 220 to the fluid reservoir 230 when the flow control mechanism 240 is in the first configuration and a second lumen 247 that fluidically couples the cannula assembly 220 to the external fluid reservoir 299 when the flow control mechanism 240 is in the second configuration.

In use, the flow control mechanism 240 can be placed in the first configuration to fluidically couple the cannula assembly 220 to the fluid reservoir 230 via the first lumen 246. In this manner, a flow of a bodily fluid can be delivered to the fluid reservoir 230, as indicated by the arrow DD in FIG. 3. More specifically, the bodily fluid can flow from the cannula assembly 220, through the first port 205 (e.g., the inlet port) and into the fluid reservoir 230. As described above in the previous embodiment, the flow of the bodily fluid can contain dermally residing microbes dislodged by a venipuncture event (e.g., the insertion of a portion of the cannula assembly 220 into a vein of the patient).

With a predetermined amount of bodily fluid disposed within the fluid reservoir 230, the flow control mechanism 240 can be moved (e.g., by an actuator and/or manual intervention from the user) to the second configuration to fluidically isolate the fluid reservoir 230 from the cannula assembly 220. More specifically, the flow control mechanism 240 can be moved from the first configuration to fluidically isolate the first lumen 246 from the cannula assembly 220 and/or the fluid reservoir 230, thereby fluidically isolating the fluid reservoir 230 from the cannula assembly 220. In addition, the movement of the flow control mechanism 240 to the second configuration can place the second lumen 247 in fluid communication with the cannula assembly 220 and the outlet port 206 (e.g., the second port) disposed at the proximal end portion 202 of the housing 201. Thus, the external fluid reservoir 299 can be fluidically coupled (as described above) to the second port 206 to deliver a flow of parenteral fluid to the patient via the second lumen 247 and the cannula assembly 220, as indicated by the arrow EE. For example, the flow of parenteral fluid can flow from the external fluid reservoir 299 (e.g., a fluid source), in the second port 206, through the second lumen 247 defined by the flow control mechanism 240, out the first port 205 and to the cannula assembly 220 to be delivered to the patient. Moreover, the flow of the parenteral fluid is substantially free from dermally residing microbes and/or other undesirable external contaminants.

In some embodiments, the transfer device 200 can be configured such that the first amount of bodily fluid needs to be conveyed to the fluid reservoir 230 before the transfer device 200 will permit the flow of the parenteral fluid to be conveyed through the transfer device 200 to the patient. In this manner, the transfer device 200 can be characterized as requiring compliance by a health care practitioner regarding the collection of the predetermined amount of bodily fluid prior to the delivery of the parenteral fluid. Similarly stated, the transfer device 200 can be configured to prevent a health care practitioner from delivering the parenteral fluid to the patient without first diverting or transferring the predetermined amount of bodily fluid to the fluid reservoir 230. In this manner, the health care practitioner is substantially prevented from introducing (whether intentionally or unintentionally) bodily surface microbes and/or other undesirable external contaminants into, for example, the flow of the parenteral fluid and/or the blood stream of the patient. In other embodiments, the fluid transfer device 200 need not include a forced-compliance feature or component.

FIGS. 4-10 illustrate a transfer device 300 according to an embodiment. The transfer device 300 includes a housing 301, a cannula assembly 320, a fluid reservoir 330, a flow control mechanism 340, and an actuator 380. The transfer device 300 can be any suitable shape, size, or configuration. For example, while shown in FIG. 4 as being substantially cylindrical, the transfer device 300 can be square, rectangular, polygonal, and/or any other non-cylindrical shape. Moreover, any portion of the transfer device 300 can include any feature or finish configured to enhance the ergonomics of the transfer device 300. For example, the housing 301 can include a portion configured to form a grip configured to be engaged by a user's hand.

Figure 5:
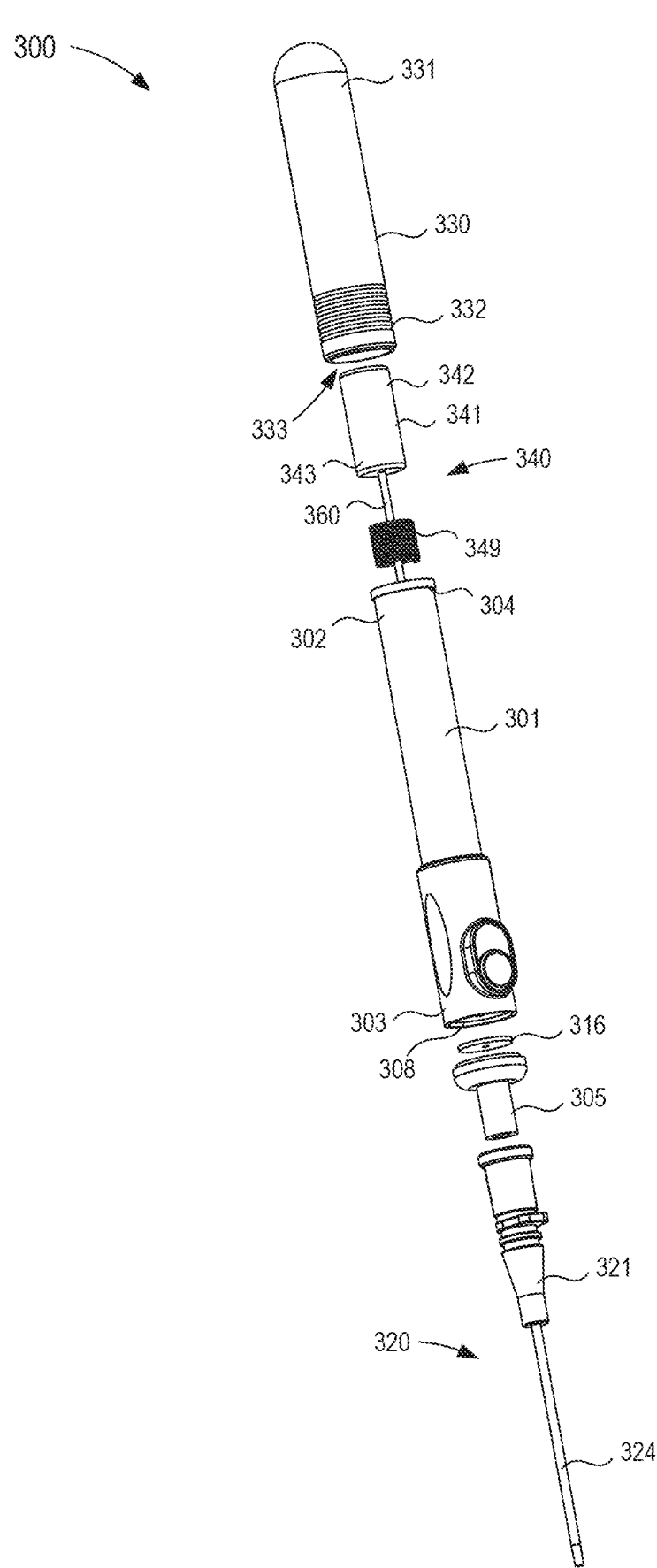
FIG. 5 is an exploded view of the fluid transfer device of FIG. 4.
Figures 6, 7:
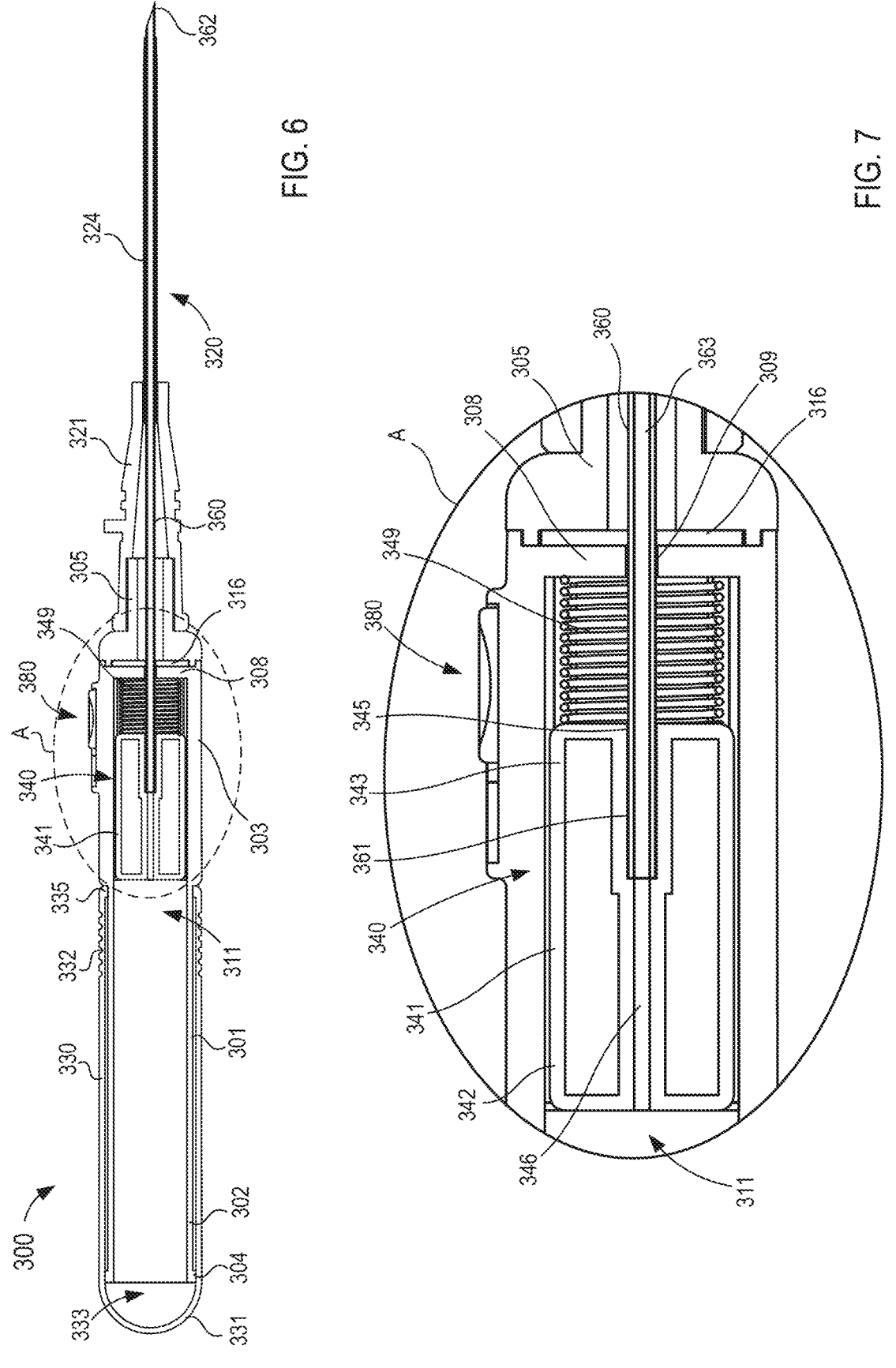
FIG. 6 is a cross-sectional view of the fluid transfer device taken along the line $X_1$-$X_1$ in FIG. 4, in a first configuration.
FIG. 7 is an enlarged view of a portion of the fluid transfer device labeled as region A in FIG. 6.

The housing 301 includes a proximal end portion 302 and a distal end portion 303 and defines an inner volume 311 therebetween (see e.g., FIG. 6). As shown in FIG. 5, the proximal end portion 302 of the housing 301 includes a protrusion 304 that selectively engages a portion of the fluid reservoir 330, as described in further detail herein. The distal end portion 303 of the housing 301 is coupled to a port 305. More specifically, the port 305 can be coupled to the distal end portion 303 in any suitable manner such as, for example, via a friction fit, a threaded coupling, a mechanical fastener, an adhesive, any number of mating recesses, and/or any combination thereof. In other embodiments, the port 305 can be monolithically formed with the housing 301. Moreover, the port 305 can be coupled to the distal end portion 303 of the housing 301 such that a seal member 316 is disposed between the port 305 and a distal wall 308 of the housing 301. In this manner, when the port 305 is coupled to the housing 301, the seal member 316 can engage the distal wall 308 of the housing 301 and the port 305 to selectively form a substantially fluid tight seal, as described in further detail herein.

As shown in FIG. 6, the port 305 is removably coupled to a lock mechanism 321 of the cannula assembly 320. The lock mechanism 321 of the cannula assembly 320 can be, at least temporarily, coupled to the port 305 to selectively place the housing 301 in fluid communication with the cannula assembly 320. For example, in some embodiments, the lock mechanism 321 can be a Luer-Lok® that receives a portion of the port 305 to physically and fluidically couple the cannula assembly 320 to the housing 301. In other embodiments, the lock mechanism 321 and the port 305 can be removably coupled in any suitable manner.

As shown in FIGS. 5 and 6, the fluid reservoir 330 defines an inner volume 333 between a proximal end portion 331 and a distal end portion 332. More specifically, the inner volume 333 is closed at the proximal end portion 331 of the fluid reservoir 330 such that at the proximal end, the inner volume 333 is fluidically isolated from a volume outside the fluid reservoir 330. Conversely, the distal end portion 332 of the fluid reservoir 330 is open such that at the distal end, the inner volume 333 can be in fluid communication with a volume outside the fluid reservoir 330. The distal end portion 332 of the fluid reservoir 330 is movably disposed about the proximal end portion 302 of the housing 301, as shown in FIG. 6. Similarly stated, the proximal end portion 302 of the housing 301 is movably disposed within the inner volume 333 defined by the fluid reservoir 330 such that the inner volume 311 defined by the housing 301 is in fluid communication with the inner volume 333 of the fluid reservoir 330. Moreover, the distal end portion 332 of the fluid reservoir 330 includes a protrusion 335 that can be placed in contact with the protrusion 304 disposed at the proximal end portion 302 of the housing 301 to substantially limit the movement of the fluid reservoir 330 relative to the housing 301, as described in further detail herein.

The flow control mechanism 340 included in the transfer device 300 is at least partially disposed within the inner volume 311 of the housing 301 and is configured to be moved between a first configuration and a second configuration. Expanding further, the flow control mechanism 340 is in the first configuration when disposed in a distal position relative to the housing 301 (see e.g., FIG. 6) and is in the second configuration when disposed in a proximal position relative to the housing 301 (see e.g., FIG. 9). As shown in FIGS. 6 and 7, the flow control mechanism 340 includes a first member 341 and a second member 360. The first member 341 includes a proximal end portion 342 and a distal end portion 343 and defines a lumen 346 therethrough. The first member 341 can be any suitable shape, size, or configuration. For example, as shown in FIG. 5, the first member 341 can be substantially cylindrical and can have a diameter substantially corresponding to the diameter of the inner volume 311 of the housing 301.

The second member 360 of the flow control mechanism 340 includes a proximal end portion 361 and a distal end portion 362 and defines a lumen 363 therethrough. As shown in FIG. 6, at least a portion of the second member 360 is movably disposed within the cannula assembly 320. More specifically, the second member 360 can be substantially cylindrical and can have a diameter substantially corresponding to the inner diameter of the cannula 324 included in the cannula assembly 320. As shown in the enlarged view of FIG. 7, the proximal end portion 361 of the second member 360 is configured to extend through the port 305 and the seal member 316 (described above), and through an opening 309 defined in the distal wall 308 to allow the second member 360 to be coupled to the first member 341. Expanding further, the proximal end portion 361 of the second member 360 is disposed within the lumen 346 defined by the first member 341. In some embodiments, the proximal end portion 361 of the second member 360 can form a friction fit with the walls of the first member 341 that define the lumen 346, thereby coupling the second member 360 to the first member 341. In other embodiments, the second member 360 can be coupled to the first member 341 via an adhesive or the like.

The distal end portion 362 of the second member 360 is configured to extend beyond a distal end of the cannula 324 included in the cannula assembly 320, when the flow control mechanism 340 is in the first configuration. Furthermore, the distal end portion 362 of the second member 360 can include a sharp point that can facilitate the insertion of the transfer device 300 (e.g., the flow control mechanism 340 and the cannula assembly 320) into a portion of a patient. For example, the distal end portion 362 of the second member 360 can be used to access a vein of the patient and facilitate the introduction of the cannula 324 into the vein. Moreover, with the cannula 324 and the distal end portion 362 of the second member 360 disposed within the vein of the patient the transfer device 300 can be configured to transfer a portion of a bodily fluid from the patient to the fluid reservoir 330 to prevent injection of dislodged dermally residing microbes that have been incompletely sterilized by surface antisepsis and/or other undesirable external contaminants.

As shown in FIG. 8, the transfer device 300 can be moved to a second configuration to begin a flow of bodily fluid (e.g., blood) from the patient to the transfer device 300. More specifically, the fluid reservoir 330 can be moved in the proximal direction relative to the housing 301 to place the transfer device 300 in the second configuration, as indicated by the arrow FF. The arrangement of the fluid reservoir 330 and the housing 301 is such that the proximal motion of the fluid reservoir 330, relative to the housing 301, increases the inner volume 333 defined by the fluid reservoir 330. Expanding further, the proximal end portion 302 of the housing 301 can be disposed within the inner volume 333 of the fluid reservoir 330 such that the protrusion 304 engages an inner surface of the fluid reservoir 330 to define a substantially fluid tight seal. In addition, the protrusion 335 of the fluid reservoir 330 can be placed in contact with the protrusion 304 of the housing 301 to limit the proximal motion of the fluid reservoir 330 relative to the housing 301. In this manner, the proximal motion of the fluid reservoir 330 relative to the housing 301 increases the collective volume of both the inner volume 311 defined by the housing 301 and the inner volume 333 of the fluid reservoir 330.

The increase of volume introduces a negative pressure within the inner volume 333 of the fluid reservoir 330 and within the inner volume 311 of the housing 301. Therefore, with the cannula 324 and the second member 360 of the flow control mechanism 340 disposed within the vein of the patient, the negative pressure urges a flow of bodily fluid (e.g., blood) through the lumen 363 and 346 defined by the second member 360 and first member 341 of the flow control mechanism 340, respectively. As indicated by the arrow GG in FIG. 8, the bodily fluid can flow through the lumen 363 and 346 of the flow control mechanism 340 and enter the collective volume formed and/or defined by the inner volume 311 of the housing 301 and the inner volume 333 of the fluid reservoir 330.

As shown in FIG. 9, when a predetermined amount of bodily fluid is disposed within the fluid reservoir 330, the flow control mechanism 340 can be moved to its second configuration (e.g., the proximal position relative to the housing 301) to place the transfer device 300 a third configuration. More specifically, the flow control mechanism 340 includes a spring 349 that is in contact with the distal wall 308 of the housing 301 and the distal end portion 343 of the first member 341 included in the flow control mechanism 340. As shown in FIGS. 6-8, the spring 349 is maintained in a compressed configuration while the transfer device 300 is in the first and second configuration. As shown in FIG. 9, when the spring 349 is allowed to expand, the spring 349 exerts a force to move the flow control mechanism 340 in the proximal direction, as indicated by the arrow HH. In some embodiments, the expansion of the spring 349 can be in response to the actuator 380. The actuator 380 can be any suitable mechanism configured to selectively interact with the spring 349 such as, for example, a push button. In other embodiments, the actuator 380 can be a slider, a pull-tab, a lever, a toggle, an electronic switch, or the like.

The proximal motion of the flow control mechanism 340 can be such that both the first member 341 and the second member 360 of the flow control mechanism 340 are disposed within the collective volume defined by the fluid reservoir 330 and the housing 301. Similarly stated, the spring 349 moves the flow control mechanism 340 in the proximal direction a sufficient distance to move the distal end portion 362 of the second member 360 through the port 305, the seal member 316, and the distal wall 308 to be disposed within the housing 301. Furthermore, the seal member 316 can be configured such that as the distal end portion 362 passes beyond the distal wall 308 of the housing 301, the seal member 316 acts to seal the opening 309 through which the second member 360 was disposed. Thus, when the flow control mechanism 340 is completely disposed within the collective volume defined by the housing 301 and the fluid reservoir 330 (e.g., the combination of the inner volume 311 and the inner volume 333, respectively), the seal member 316 seals the distal end portion 303 of the housing 301 and the fluid reservoir 330 is substantially fluidically isolated from the cannula assembly 320.

Figure 10:
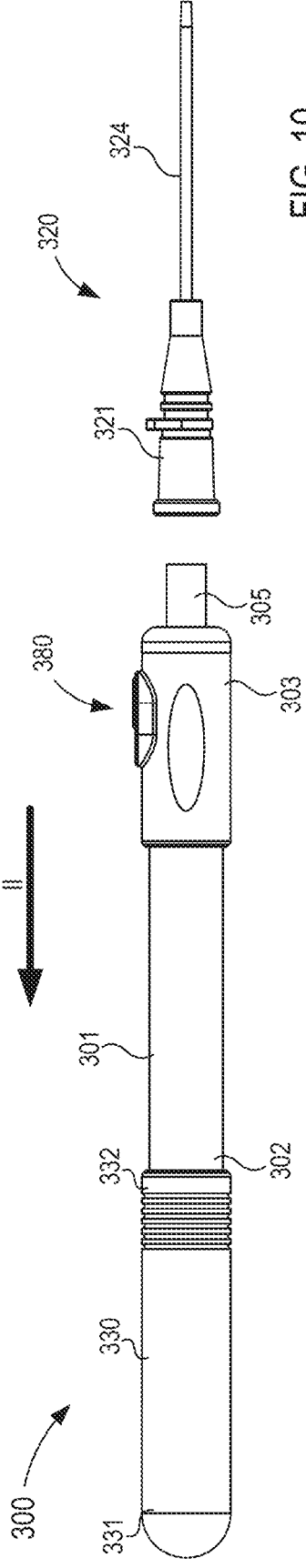
FIG. 10 is a side view of the fluid transfer device of FIG. 4 in a fourth configuration.

With the fluid reservoir 330 fluidically isolated from the cannula assembly 320, the transfer device 300 can be placed in a fourth configuration, as shown in FIG. 10. More specifically, the housing 301 and the fluid reservoir 330 can be collectively moved in the proximal direction such that the port 305 is physically decoupled from the lock mechanism 321 of the cannula assembly 320, as indicated by the arrow II. In this manner, the fluid reservoir 330 can contain and fluidically isolate a portion of the bodily fluid (e.g., blood) that includes, for example, dermally residing microbes dislodged during the venipuncture event (e.g., the insertion of the distal end portion 362 of the second member 360 of the flow control mechanism 340). Furthermore, with the port 305 decoupled from the lock mechanism 321 of the cannula assembly 320, the cannula assembly 320 can be physically and fluidically coupled to an external fluid reservoir (not shown in FIG. 10) that can deliver a flow of a parenteral fluid that is substantially free from the dermally residing microbes.

Figure 11:
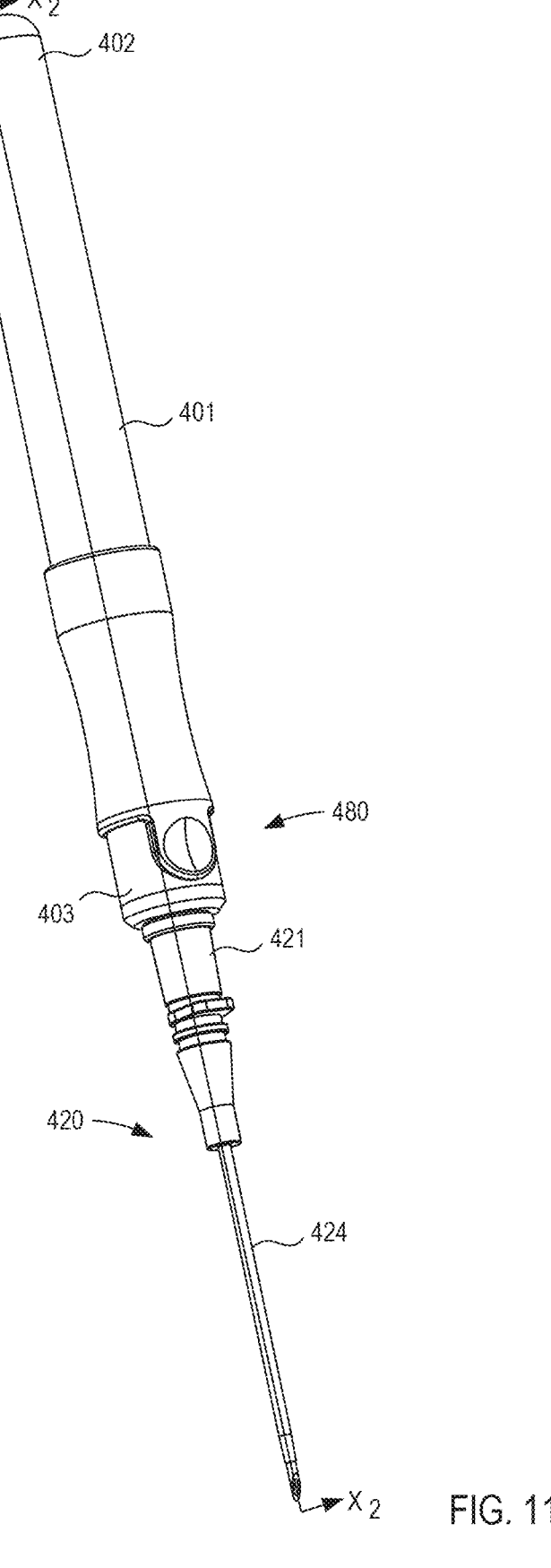
FIG. 11 is a perspective view of a fluid transfer device according to an embodiment.
Figure 12:
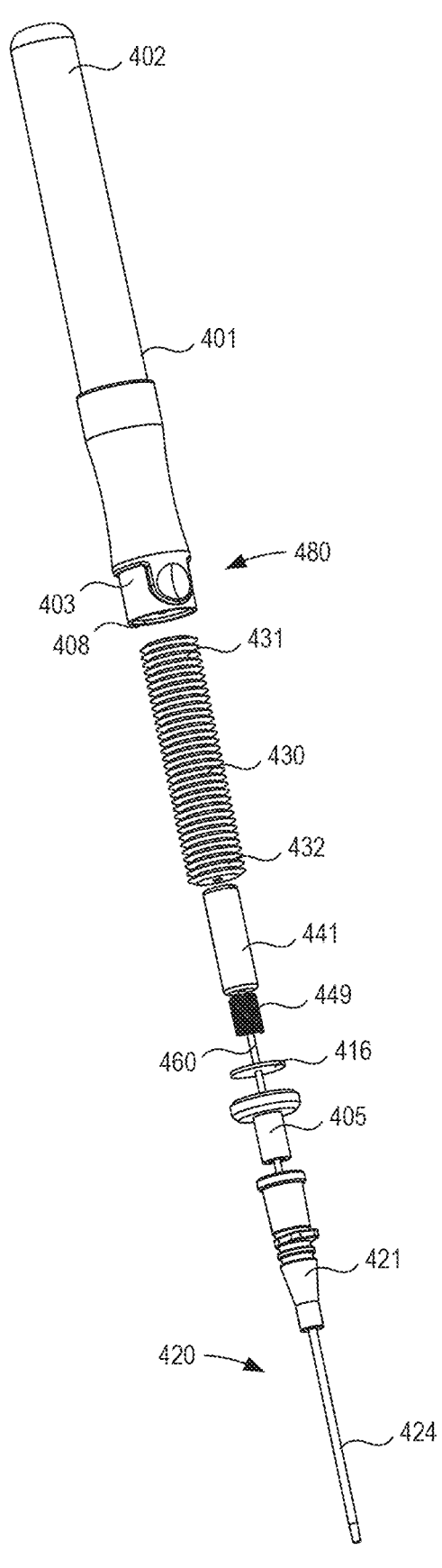
FIG. 12 is an exploded view of the fluid transfer device of FIG. 11.

While the fluid reservoir 330 is shown in FIGS. 4-10 as being disposed about a portion of the housing 301, in some embodiments, a transfer device can include a fluid reservoir the is substantially enclosed within a housing. For example, FIGS. 11-15 illustrate a transfer device 400 according to an embodiment. The transfer device 400 includes a housing 401, a cannula assembly 420, a fluid reservoir 430, a flow control mechanism 440, and an actuator 480. As shown in FIGS. 11 and 12, the overall size and shape of the transfer device 400 can be substantially similar to the overall size and shape of the transfer device 300 described above in reference to FIG. 4. In addition, the cannula assembly 420, the flow control mechanism 440, and the actuator 480 can be substantially similar in form and function to the cannula assembly 320, the flow control mechanism 340, and the actuator 380 included in the transfer device 300, described above in reference to FIGS. 4-10. Therefore, the cannula assembly 420, the flow control mechanism 440, and the actuator 480 are not described in further detail herein.

The housing 401 of the transfer device 400 includes a proximal end portion 402 and a distal end portion 403 and defines an inner volume 411 therebetween. More specifically, the housing 401 is substantially closed at the proximal end portion 402 such that at the proximal end, the inner volume 411 is fluidically isolated from a volume outside the housing 401. The distal end portion 403 of the housing 401 is coupled to a port 405. The port 405 is substantially similar to the port 305 described above, and can be coupled to the distal end portion 403 of the housing 401 such that a seal member 416 is disposed between the port 405 and a distal wall 408 of the housing 401. In this manner, the seal member 416 can form a substantially fluid tight seal between the distal wall 408 and the port 405 (described in detail with reference the port 305 shown in FIGS. 6 and 7). Furthermore, the port 405 can be configured to removably couple the housing 401 to the cannula assembly 420. For example, the port 405 can be, at least temporarily, physically and fluidically coupled to a lock mechanism 421 included in the cannula assembly 420. In this manner, the housing 401 and the cannula assembly 420 can be selectively placed in fluid communication.

Figures 13, 14:
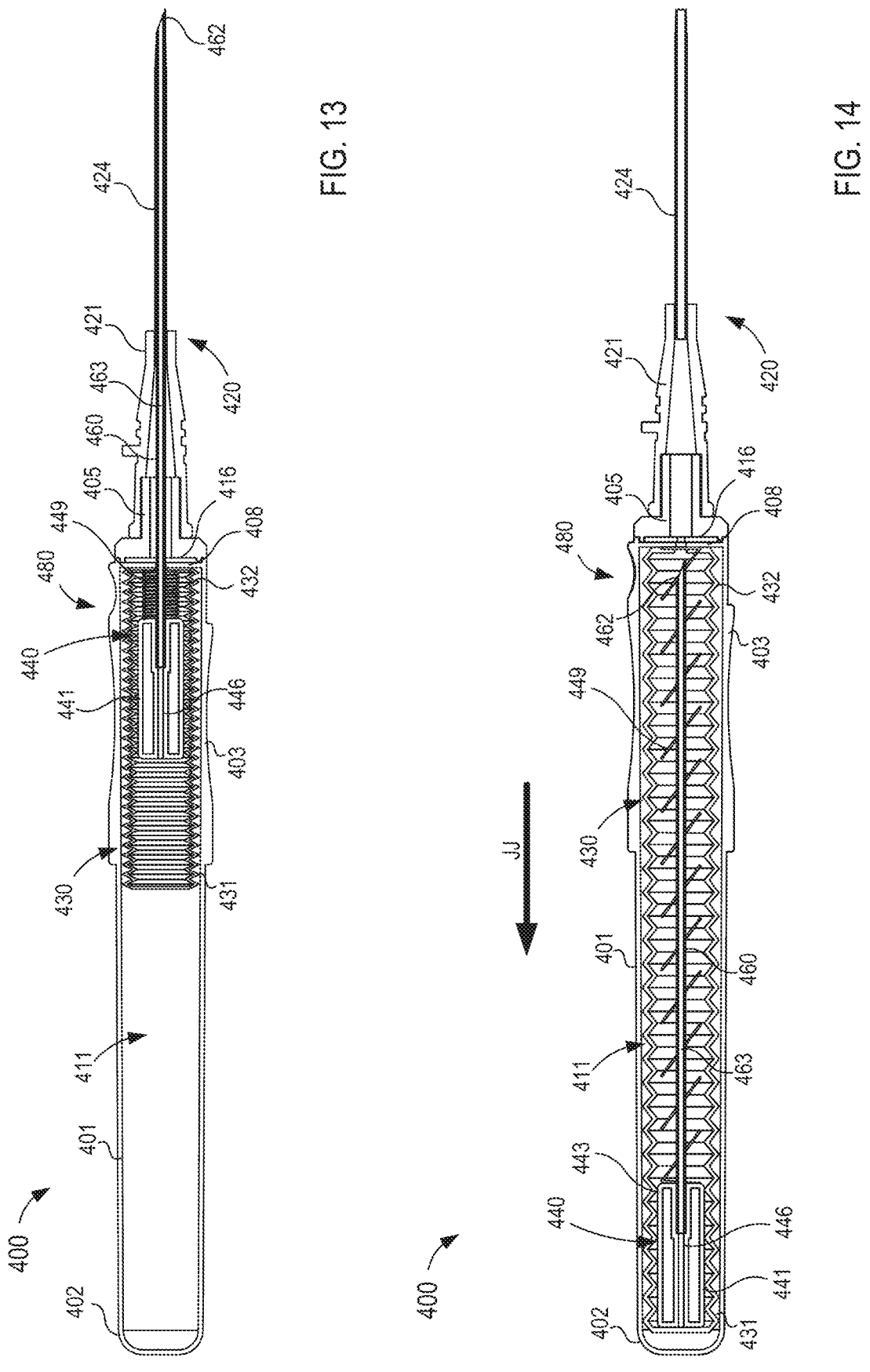
FIGS. 13 and 14 are cross-sectional views of the fluid transfer device taken along the line $X_2$-$X_2$ in FIG. 11, in a first and second configuration, respectively.

The fluid reservoir 430 included in the transfer device 400 is movably disposed within the inner volume 411 defined housing 401. More specifically, the fluid reservoir 430 is configured to move within the housing 401 between a first configuration (FIG. 13) and a second configuration (FIG. 14). The fluid reservoir 430 defines an inner volume 433 between a proximal end portion 431 and a distal end portion 432. The inner volume 433 is configured to selectively receive at least a portion of the flow control mechanism 440. Furthermore, the flow control mechanism 440 can moved between a first position and a second position to move the fluid reservoir 430 between the first configuration and the second configuration, as described in further detail herein.

As shown in FIG. 13, the flow control mechanism 440 is in the first position when disposed in a distal position relative to the housing 401. While in the first position, a first member 441 of the flow control mechanism 440 is completely contained within the inner volume 433 and a second member 460 is configured to extend from the first member 441 through the distal end portion 432 of the fluid reservoir 430. The second member 460 of the flow control mechanism 460 further extends through the housing 401 and the port 405 to be at least partially disposed within the cannula assembly 420 (as described above in detail with reference to the second member 360 shown in FIGS. 6 and 7). In this manner, a distal end portion 462 of the second member 460 can extend beyond a cannula 424 of the cannula assembly 420 to facilitate the insertion of the cannula 424 into a portion of a patient. Moreover, with the distal end portion 462 of the second member 460 disposed within the portion of the patient, a lumen 463 defined by the second member 460 and a lumen 446 defined by the first member 441 can place the fluid reservoir 430 in fluid communication with the portion of the patient.

In use, the transfer device 400 can be moved from the first configuration (FIG. 13) to the second configuration (FIG. 14) to facilitate the flow of a bodily fluid (e.g., blood) into the fluid reservoir 430. More specifically, the flow control mechanism 440 includes a mechanical actuator 449 (e.g., a spring) that is in contact with the distal wall 408 of the housing 401 and the first member 441 of the flow control mechanism 440. As shown in FIG. 13, the mechanical actuator 449 is maintained in a compressed configuration while the transfer device 400 is in the first configuration. Similarly stated, the flow control mechanism 440 is in the first position relative to the housing 401 when the mechanical actuator 449 is in the compressed configuration. As shown in FIG. 14, when the mechanical actuator 449 is allowed to expand, the mechanical actuator 449 exerts a force to move the flow control mechanism 440 in the proximal direction, as indicated by the arrow JJ. In some embodiments, the expansion of the mechanical actuator 449 can be in response to an actuation of the actuator 480.

The proximal motion of the flow control mechanism 440 moves within the inner volume 433 to place the first member 441 in contact with the proximal end portion 441 of the fluid reservoir 430. In this manner, the flow control mechanism 440 urges the proximal end portion 431 of the fluid reservoir 430 to move in the direction of the arrow JJ (e.g., the proximal direction). Moreover, the distal end portion 432 of the fluid reservoir 430 can be coupled to the distal wall 408 of the housing 401 such that as the proximal end portion 431 moves in the proximal direction, the fluid reservoir 430 expands. Similarly stated, the fluid reservoir 430 can form a bellows in which the proximal motion of the flow control mechanism 440 moves the fluid reservoir 430 from a compressed configuration (e.g., the first configuration) to an expanded configuration (e.g., the second configuration).

The movement of the proximal end portion 431 relative to the distal end portion 432 increases the inner volume 433 defined by the fluid reservoir 430 and introduces a negative pressure within the inner volume 433. Moreover, with the lumen 446 of the first member 441 and the lumen 463 of the second member 460 in fluid communication with the fluid reservoir 430, at least a portion of the negative pressure is transferred through the flow control mechanism 440. Therefore, while the flow control mechanism 440 is being moved to the second position (FIG. 14), the negative pressure urges a flow of bodily fluid (e.g., blood) through the lumen 463 and 446 defined by the second member 460 and first member 441 of the flow control mechanism 440, respectively. Expanding further, as shown in FIG. 14, the proximal motion of the flow control mechanism 440 is such that the second member 460 is retracted to a proximal position relative to the distal wall 408 of the housing 401. Prior to being disposed in the proximal position relative to the distal wall 408, however, the lumen 463 is maintained in fluid communication with the portion of the patient via the cannula 424. In this manner, the flow control mechanism 440 transfers the bodily fluid to the fluid reservoir 430 while being moved in the proximal direction and prior to being disposed in the second position. Thus, when the second member 460 is retracted to the proximal position relative to the distal wall 408, the flow control mechanism 440 has transferred a predetermined amount of bodily fluid to the fluid reservoir 430 and the seal member 416 can act to fluidically isolate the fluid reservoir 430. Similarly stated, the flow control mechanism 440 is configured to transfer the predetermined amount of bodily fluid to the fluid reservoir 430 concurrently with the proximal motion of both the flow control mechanism 440 and the fluid reservoir 430.

Figure 15:
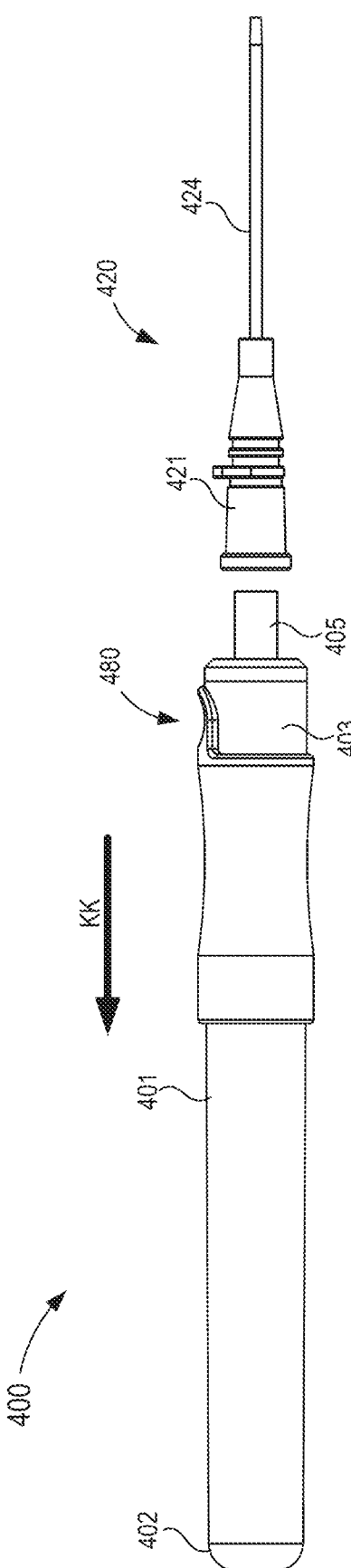
FIG. 15 is a side view of the fluid transfer device of FIG. 11 in a third configuration.

With the fluid reservoir 430 fluidically isolated from the cannula assembly 420, the transfer device 400 can be placed in a third configuration, as shown in FIG. 15. More specifically, the housing 401 and the fluid reservoir 430 can be collectively moved in the proximal direction to physically decouple the port 405 from the lock mechanism 421 of the cannula assembly 420, as indicated by the arrow KK. In some embodiments, the actuator 480 can facilitate the decoupling of the port 405 from the lock mechanism 421. In other embodiments, a second actuator (not shown) can be engaged to decouple the port 405 from the lock mechanism 421. In other embodiments, an actuator need not be engaged to decouple the port 405 from the lock mechanism 421.

With the port 405 decoupled from the lock mechanism 421, the fluid reservoir 430 can contain and fluidically isolate a portion of the bodily fluid (e.g., blood) that includes, for example, dermally residing microbes dislodged during the venipuncture event (e.g., the insertion of the distal end portion 462 of the second member 460 of the flow control mechanism 440). Furthermore, with the port 405 decoupled from the lock mechanism 421, the cannula assembly 420 can be physically and fluidically coupled to an external fluid reservoir (not shown in FIG. 15) that can deliver a flow of a parenteral fluid that is substantially free from the dermally residing microbes, as described above.

Figure 16:
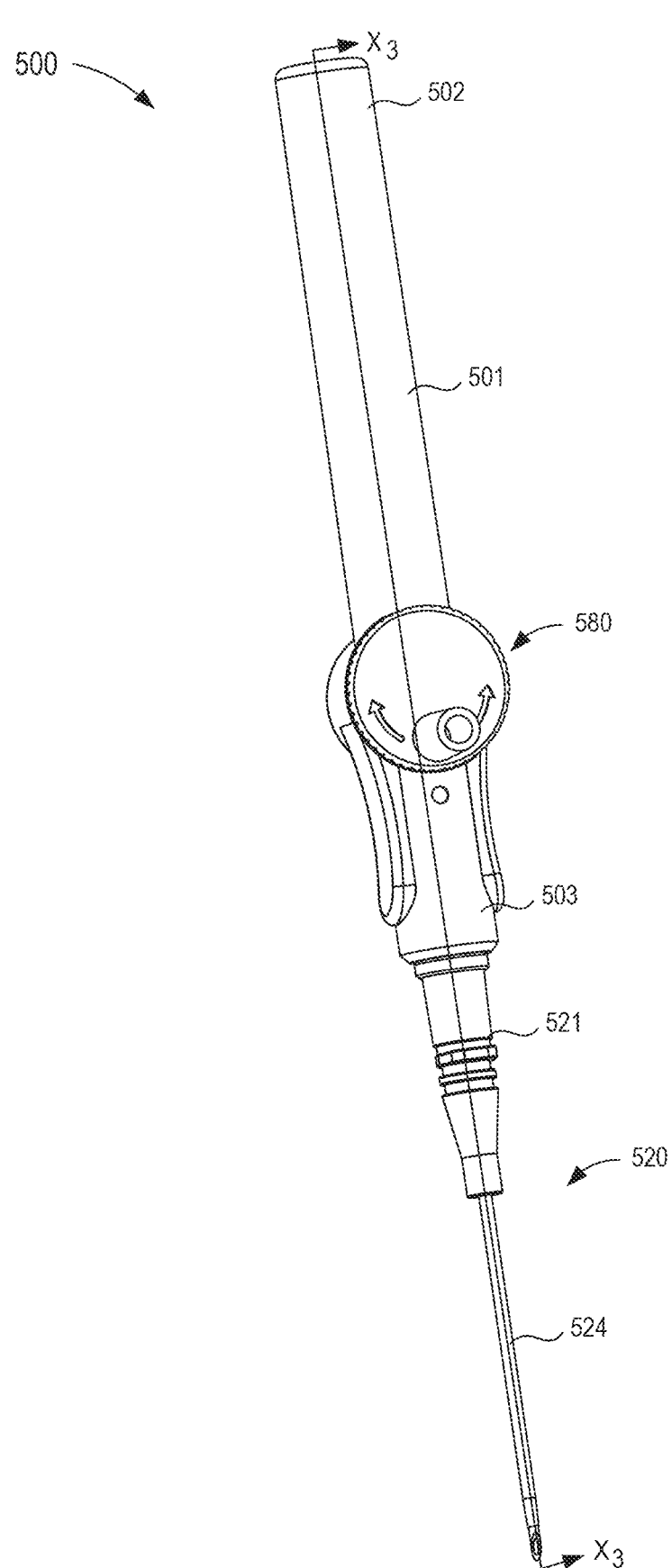
FIG. 16 is a perspective view of a fluid transfer device according to an embodiment.
Figure 17:
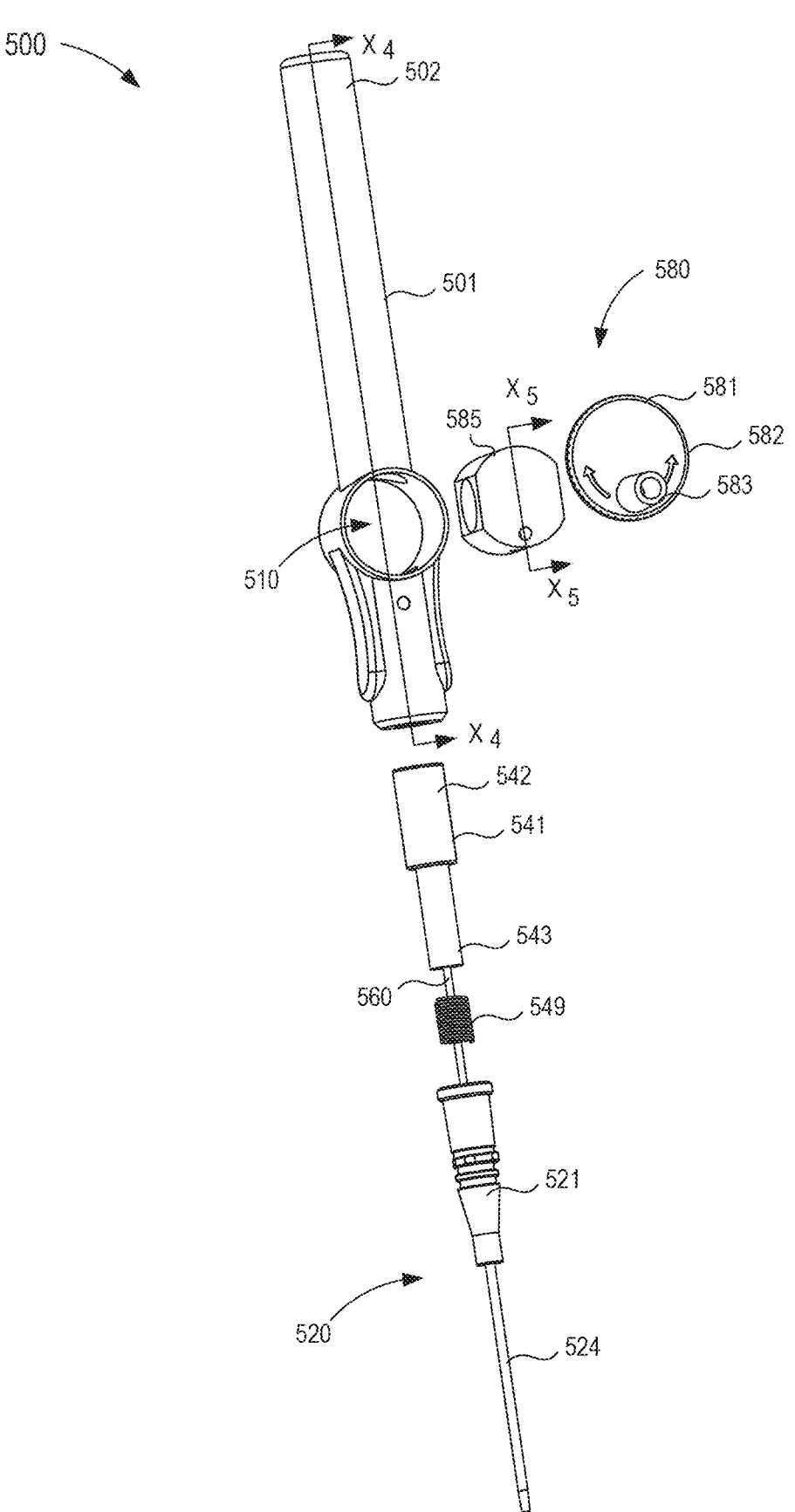
FIG. 17 is an exploded view of the fluid transfer device of FIG. 16.

While the fluid reservoir 430 is shown in FIGS. 11-15 as being disposed within the inner volume 411 of the housing 401, in some embodiments, a fluid reservoir can be physically and fluidically coupled to a portion of the transfer device. For example, FIGS. 16-23 illustrate a transfer device 500 according to an embodiment. The transfer device 500 includes a housing 501, a cannula assembly 520, a flow control mechanism 540, and an actuator mechanism 580. As shown in FIGS. 16 and 17, the overall size and shape of the transfer device 500 can be substantially similar to the overall size and shape of the transfer device 300 described above in reference to FIG. 4. In other embodiments, the overall size and shape of the transfer device 500 can be square, rectangular, polygonal, and/or any other non-cylindrical shape. In addition, the cannula assembly 520 can be substantially similar in form and function to the cannula assembly 320 included in the transfer device 300, described above in reference to FIGS. 4-10. Therefore, the cannula assembly 520 is not described in further detail herein.

Figures 18, 19:
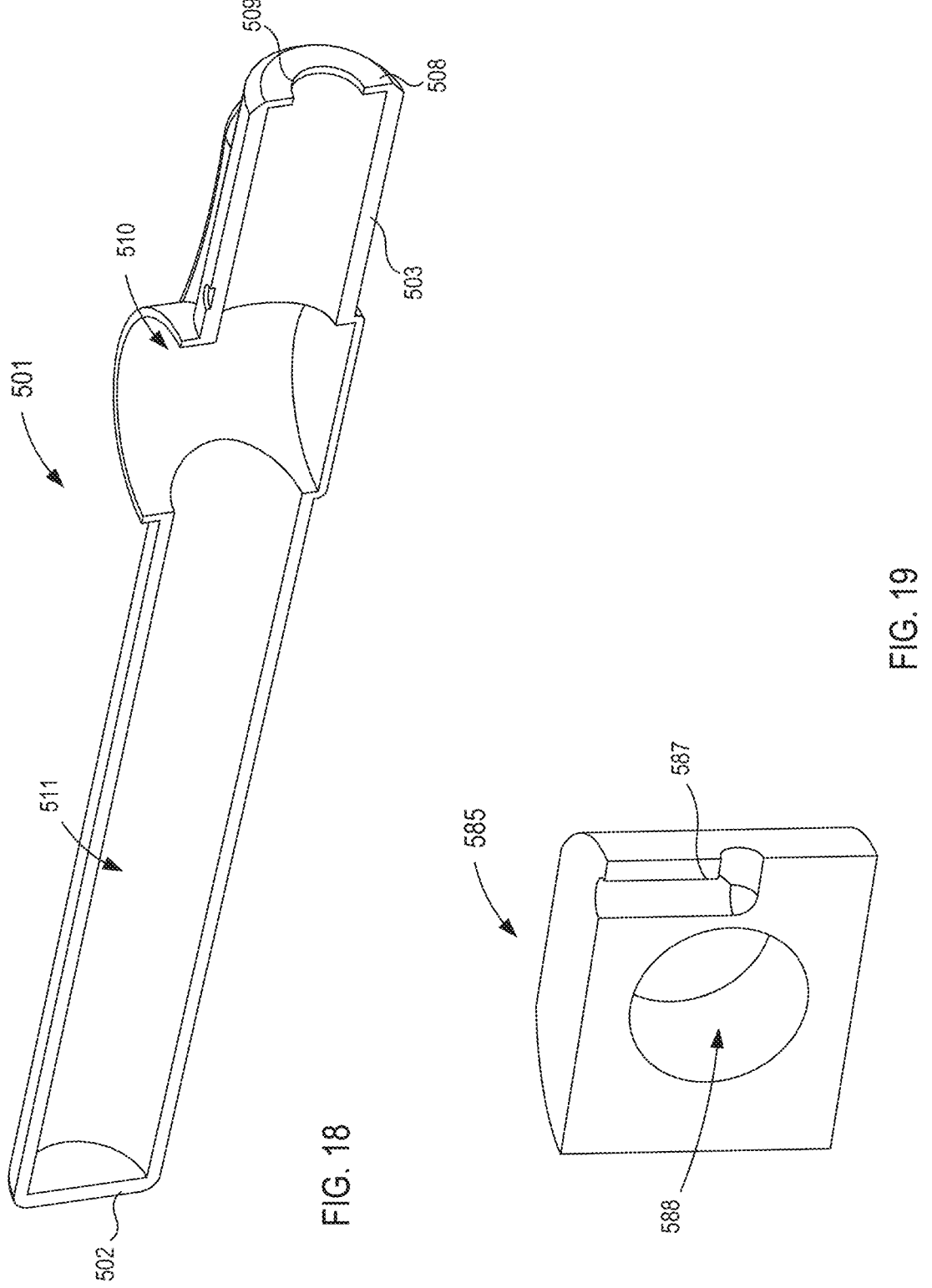
FIG. 18 is a cross-sectional perspective view of a housing included in the fluid transfer device taken along the line $X_4$-$X_4$ in FIG. 17.
FIG. 19 is a cross-sectional perspective view of a portion of a flow control mechanism included in the fluid transfer device taken along the line $X_5$-$X_5$ in FIG. 17.

As shown in FIG. 18, the housing 501 of the transfer device 500 includes a proximal end portion 502 and a distal end portion 503 and defines an inner volume 511 therebetween. The housing 501 is substantially closed at the proximal end portion 502 such that at the proximal end, the inner volume 511 is fluidically isolated from a volume outside the housing 501. The distal end portion 503 of the housing 501 includes a distal wall 508 that defines an opening 509 configured to receive, at least temporarily, a portion of the flow control mechanism 540, as described in further detail herein. The housing 501 further defines an actuator chamber 510 configured to receive at least a portion of the actuator mechanism 580. As shown in FIG. 18, the walls of the housing 501 can be arranged such that the actuator chamber 510 is a bore with a centerline that is substantially perpendicular to a centerline defined by the inner volume 511.

Referring back to FIG. 17, the actuator mechanism 580 includes a first actuator member 581 and a second actuator member 585. As described in further detail herein, the actuator mechanism 580 can be moved between a first configuration (see e.g., FIG. 16) and a second configuration (see e.g., FIG. 21). The first actuator member 581 can be rotatably coupled to the walls of the housing 501 defining the actuator chamber 510. Similarly stated, the first actuator member 581 is configured to be disposed substantially outside the housing 501 and can be rotatably coupled to the walls of the housing 501 that define the actuator chamber 510. The first actuator member 581 includes an engagement portion 582 and a port 583 configured to be physically and fluidically coupled to a fluid reservoir, as described in further detail herein.

As shown in FIG. 19, the second actuator member 585 can be substantially cylindrical and is configured to be disposed within the actuator chamber 510 defined by the housing 501. The second actuator member 585 defines a lumen 587 and a flow control channel 588. The lumen 587 is configured to be in fluid communication with the port 583 of the first actuator member 581. In this manner, the lumen 587 and the port 583 can receive a flow of a bodily fluid when the actuator mechanism 580 is in the first configuration, as described in further detail herein. The flow control channel 588 is configured to receive at least a portion of the flow control mechanism 540 when the actuator mechanism 580 is placed in the second configuration, as described in further detail herein.

Figures 20, 21:
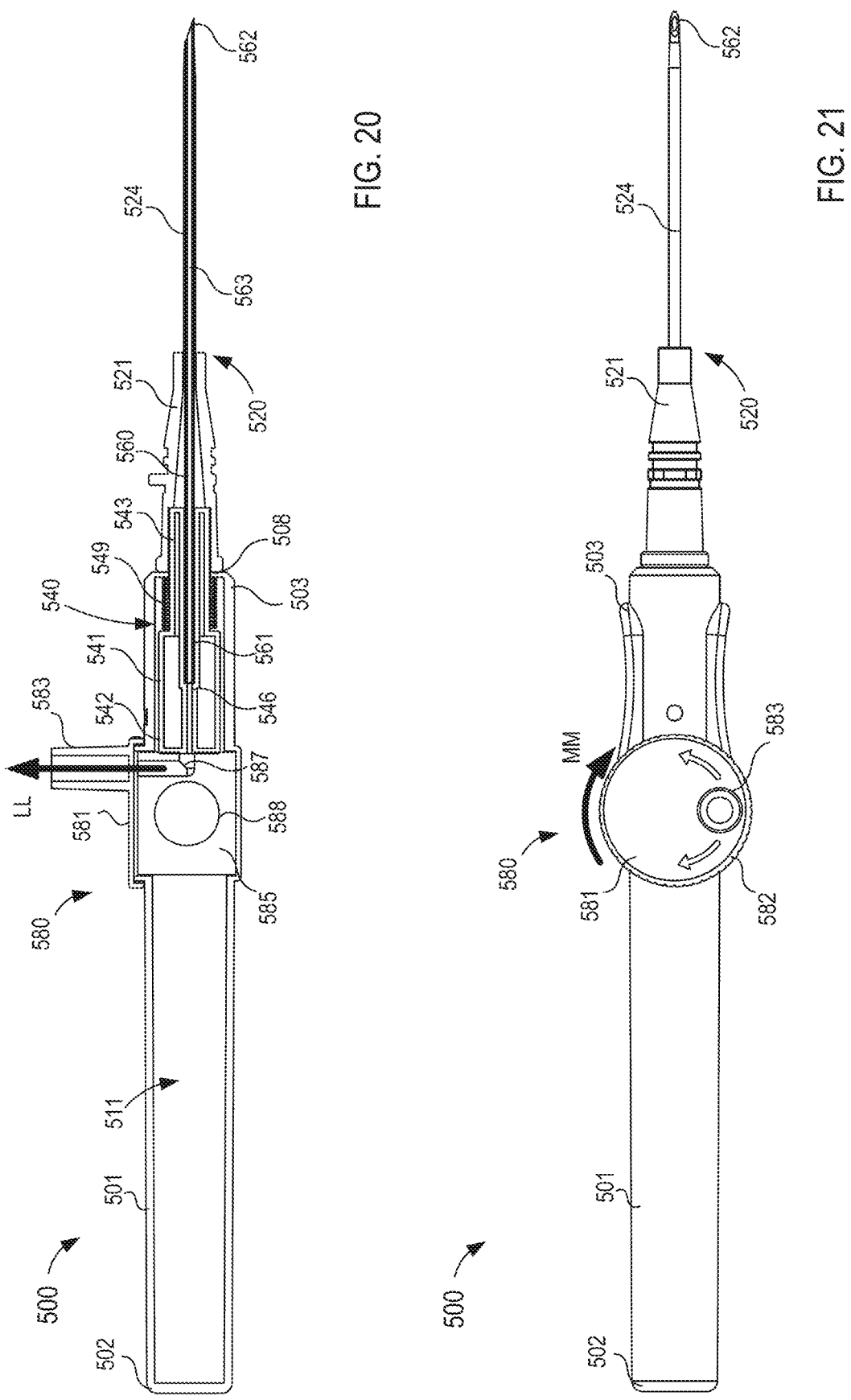
FIG. 20 is a cross-sectional view of the fluid transfer device taken along the line $X_3$-$X_3$ in FIG. 16, in a first configuration.
FIG. 21 is a front view of the fluid transfer device of FIG. 16 in a second configuration.

The flow control mechanism 540 included in the transfer device 500 is at least partially disposed within the inner volume 511 of the housing 501 and is configured to be moved between a first position and a second position. Expanding further, the flow control mechanism 540 is in the first position when disposed in a distal position relative to the housing 501 (see e.g., FIG. 20) and is in the second position when disposed in a proximal position relative to the housing 501 (see e.g., FIG. 22). As shown in FIGS. 17 and 20, the flow control mechanism 540 includes a first member 541 and a second member 560. The first member 541 includes a proximal end portion 542 and a distal end portion 543 and defines a lumen 546 therethrough. The first member 541 can be any suitable shape, size, or configuration. For example, as shown in FIG. 17, the first member 541 can be substantially cylindrical with the proximal end portion 542 having a first diameter that substantially corresponds to the diameter of the flow control channel 588 defined by the second actuator member 585. As shown in FIG. 20, the first member 541 can be configured such that when the flow control mechanism 540 is in the first position, the lumen 546 defined by the first member 541 is in fluid communication with the lumen 587 defined by the second actuator member 585, as described in further detail herein.

The distal end portion 543 of the first member 541 can have a second diameter, smaller than the first diameter, substantially corresponding to an inner diameter of a lock mechanism 521 included in the cannula assembly 520. For example, in some embodiments, the distal end portion 543 can extend through the opening 509 defined by the distal wall 508 of the housing 501 to be disposed within the lock mechanism 521. In some embodiments, the distal end portion 543 can form a friction fit with an inner surface of the lock mechanism 521 to removably couple the flow control mechanism 540 to the cannula assembly 520. Furthermore, with the proximal end portion 542 of the first member 541 disposed in a proximal position relative to the distal wall 508 and with the diameter of the proximal end portion 542 substantially larger than the diameter of the opening 509, the flow control mechanism 540 operatively couples the housing 501 to the cannula assembly 520.

The second member 560 of the flow control mechanism 540 includes a proximal end portion 561 and a distal end portion 562 and defines a lumen 563 therethrough. As shown in FIG. 20, at least a portion of the second member 560 is movably disposed within a cannula 524 of the cannula assembly 520. As described above with respect to the flow control mechanism 340, the proximal end portion 561 of the second member 560 is configured to extend through the lock mechanism 521 to be coupled to the first member 541. Expanding further, the proximal end portion 561 of the second member 560 is disposed within the lumen 546 defined by the first member 541. The distal end portion 562 of the second member 560 is configured to extend beyond a distal end of the cannula 524 included in the cannula assembly 520, when the flow control mechanism 540 is in the first configuration. In this manner, the second member 560 can facilitate the insertion of the transfer device 500 into a portion of a patient (e.g., the distal end can include a sharp point) and can further facilitate a transfer of a bodily fluid from the patient to a fluid reservoir (e.g., via the lumen 563).

For example, as shown in FIG. 20, the transfer device 500 can be in a first configuration when the flow control mechanism 540 is in the first position and the actuator mechanism 580 is in its first configuration. In this manner, the second member 560 of the flow control mechanism 540 and the cannula 524 of the cannula assembly 520 can be inserted into a portion of the patient, such as a vein, to place the transfer device 500 in fluid communication with the portion of the patient. Furthermore, a fluid reservoir (not shown in FIGS. 16-23) can be physically and fluidically coupled to the port 583 of the second actuator member 581. The arrangement of the flow control mechanism 540 and the actuator mechanism 580 is such that when the fluid reservoir is physically and fluidically coupled to the port 583, the fluid reservoir is in fluid communication with the lumen 587 defined by the second actuator member 585 and the two lumen 546 and 563 defined by the first member 541 and the second member 560 of the flow control mechanism 540, respectively. In some embodiments, the fluid reservoir can be, for example, a Vacutainer®. In such embodiments, the fluid reservoir can define a negative pressure such that when fluidically coupled to the port 583, the fluid reservoir introduces a suction force within the portion of the patient (e.g., via the lumen 587, 546, and 563). In this manner, a portion of the suction force can urge a flow of bodily fluid through the lumen 563, 546, and 587 and into the fluid reservoir, as indicated by the arrow LL in FIG. 20. Moreover, the flow of bodily fluid can be such that dermally residing microbes dislodged during a venipuncture event (e.g., the insertion of the flow control mechanism 540 and the cannula 524) become entrained therein and are transferred to the fluid reservoir.

With a predetermined amount of bodily fluid transferred to the fluid reservoir, the fluid reservoir can be decoupled from the port 583 (e.g., physically and fluidically or only fluidically). In this manner, a user can engage the first actuator member 581 to move the actuator mechanism 580 to its second configuration and thereby place the transfer device in a second configuration. For example, as indicated by the arrow MM in FIG. 21, the user (e.g., a physician, a nurse, a phlebotomist, etc.) can rotate the first actuator member 581 in a clockwise direction relative to the housing 501.

The actuator mechanism 580 is such that the rotation of the first actuator member 581 urges the second actuator member 585 to also rotate relative to the housing 501. In this manner, a centerline defined by the flow control channel 587 is rotated from a first configuration in which the centerline is substantially perpendicular to the centerline defined by the inner volume 511 to a second configuration in which the centerline is substantially parallel to the centerline of the inner volume 511. Similarly stated, the second actuator member 585 is rotated such that the centerline defined by the flow control channel 587 is aligned with the centerline defined by the inner volume 511.

Figures 22, 23:
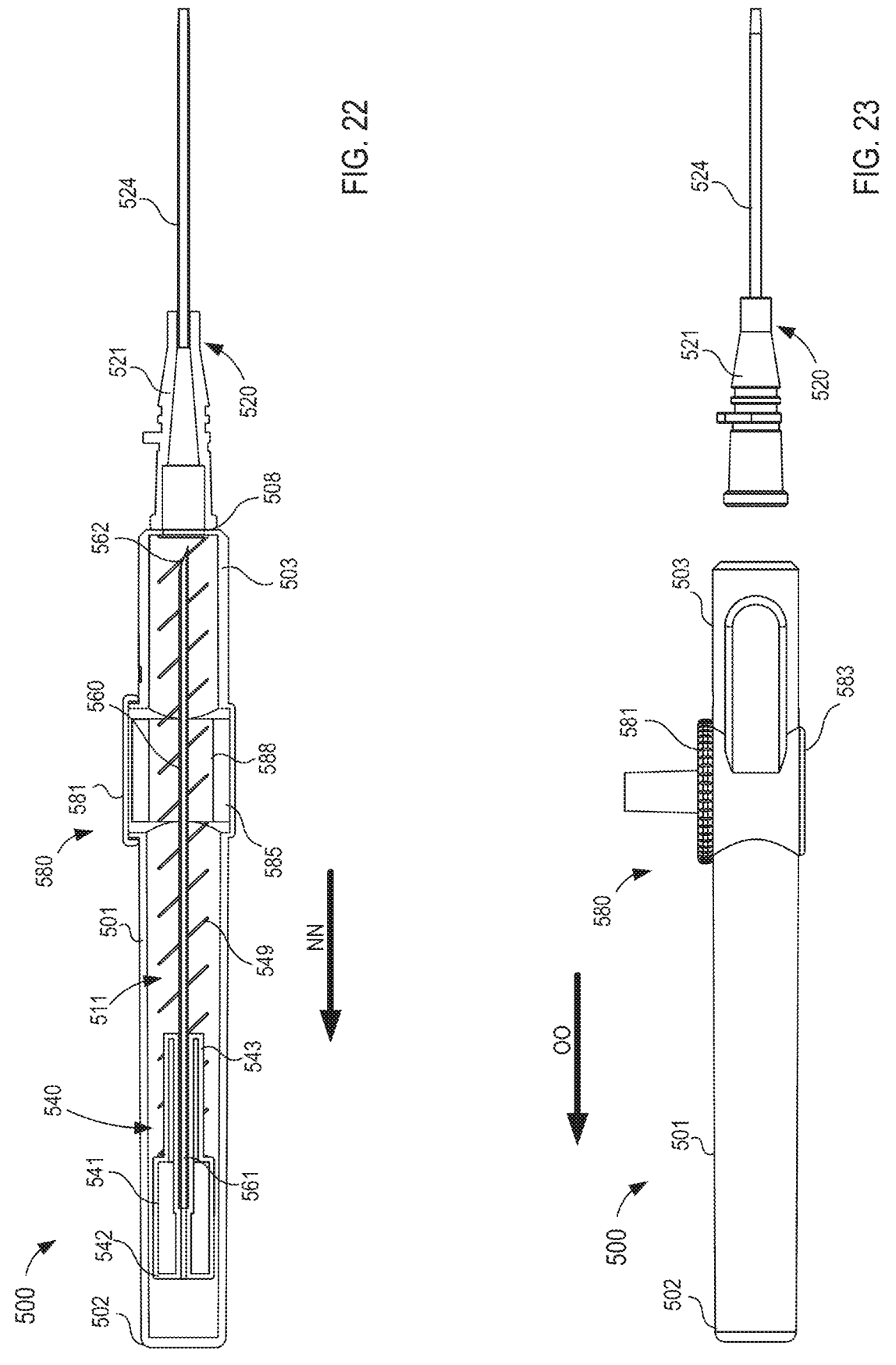
FIG. 22 is a cross-sectional view of the fluid transfer device taken along the line $X_3$-$X_3$ in FIG. 16, in the second configuration.
FIG. 23 is a side view of the fluid transfer device of FIG. 16 in a third configuration.

As shown in FIG. 22, the rotation of the actuator mechanism 580 toward the second configuration can facilitate the movement of the flow control mechanism 540 from the first position toward the second position. More specifically, the flow control mechanism 540 includes a spring 549 that is disposed about the distal end portion 543 of the first member 541 and is in contact with the distal wall 508 of the housing 501 and a surface of the first member 541. The spring 549 is maintained in a compressed configuration while the transfer device 500 is in the first configuration. For example, as shown in FIG. 20, a proximal surface of the first member 541 of the flow control mechanism 540 can be in contact with a surface of the second actuator mechanism 585 such that the second actuator mechanism 585 prevents proximal movement of the flow control mechanism 540. When the actuator mechanism 580 is moved to the second configuration and the flow control channel 587 is aligned with the inner volume 511 (as described above), however, the proximal surface of the first member 541 is no longer in contact with the surface of the second actuator member 585 and the spring 549 is allowed to expand.

The expansion of the spring 549 exerts a force on the first member 541 of the flow control mechanism 540 to move the flow control mechanism 540 in the proximal direction, as indicated by the arrow NN in FIG. 22. In this manner, the flow control mechanism 540 can pass through the flow control channel 587 defined by the second actuator member 585 to be disposed in the second position (e.g., the distal position). The proximal motion of the flow control mechanism 540 is such that both the first member 541 and the second member 560 of the flow control mechanism 540 are disposed within the inner volume 511 defined by the housing 501. Similarly stated, the spring 549 moves the flow control mechanism 540 in the proximal direction a sufficient distance to move the distal end portion 562 of the second member 560 through the opening 509 defined by the distal wall 508 to be disposed within the housing 501.

As shown in FIG. 23, with the flow control mechanism 540 disposed within the housing 501, the distal end portion 543 of the first member 541 is no longer disposed within the lock mechanism 521 of the cannula assembly 520. In this manner, the housing 501 is physically and fluidically decoupled from the cannula assembly 520 and can be moved away from the cannula assembly 520, as indicated by the arrow OO in FIG. 23. Furthermore, with the housing 501 decoupled from the lock mechanism 521, the cannula assembly 520 can be physically and fluidically coupled to an external fluid reservoir (not shown in FIG. 23) that can deliver a flow of a parenteral fluid to the portion of the patient that is substantially free from the dermally residing microbes.

While the transfer devices described above are configured to include a cannula assembly that is physically and fluidically decoupled from a portion of the transfer device to receive a parenteral fluid, in some embodiments, a transfer device can include a cannula assembly configured to remain physically coupled to a portion of the transfer device. For example, FIGS. 24-30 illustrate a transfer device 600 according to an embodiment. The transfer device 600 includes a housing 601, a cannula assembly 620, a fluid reservoir 630, and a flow control mechanism 640. In use, the transfer device 600 can be moved between a first, a second, and a third configuration to receive a predetermined amount of a bodily fluid from a patient and to deliver a flow of a parenteral fluid to the patient that is substantially free from, for example, dermally residing microbes.

Figure 24:
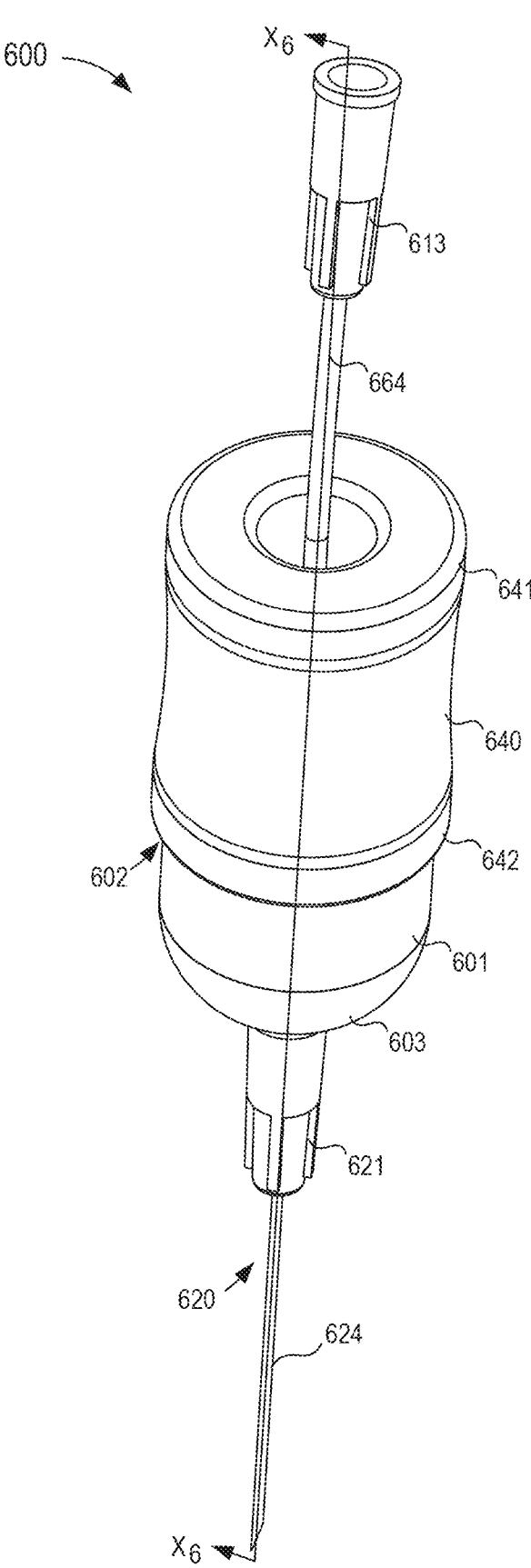
FIG. 24 is a perspective view of a fluid transfer device according to an embodiment.
Figure 25:
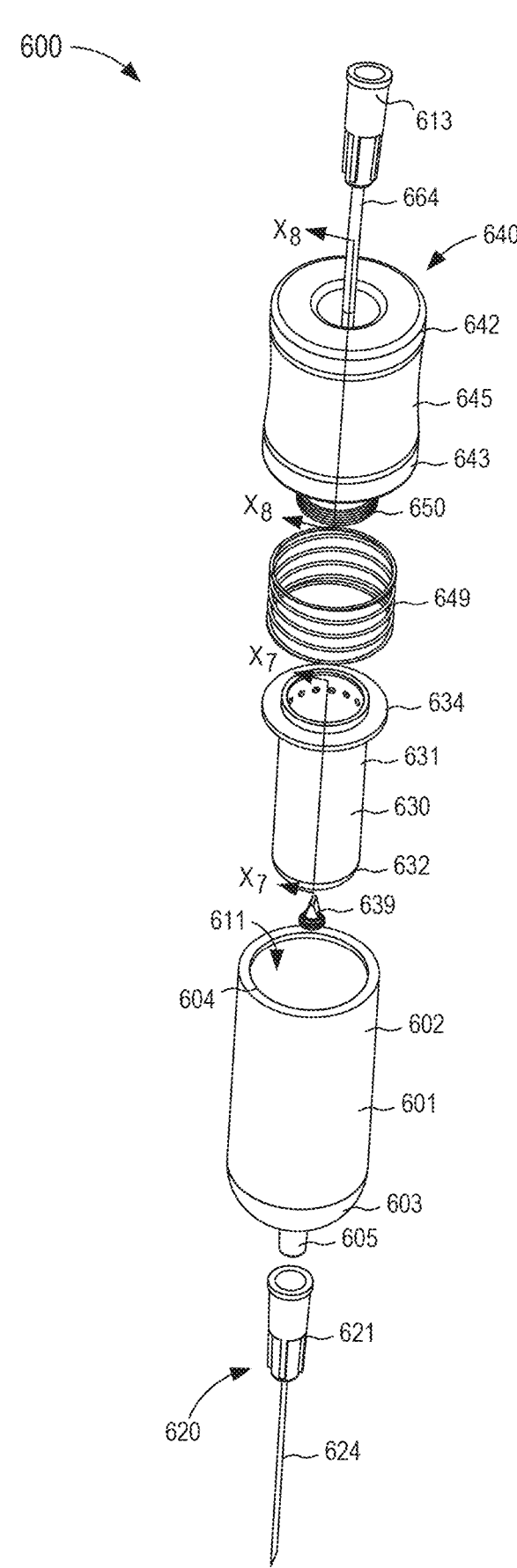
FIG. 25 is an exploded view of the fluid transfer device of FIG. 24.

As shown in FIGS. 24 and 25, the housing 601 includes a proximal end portion 602 and a distal end portion 603 and defines an inner volume 611 therebetween. The proximal end portion 602 is substantially open such that the inner volume 611 can selectively receive the fluid reservoir 630 and at least a portion of the flow control mechanism 640. In addition, the proximal end portion 602 includes a protrusion 604 configured to engage a portion of the flow control mechanism 640, as described in further detail herein.

The distal end portion 603 of the housing 601 includes a distal port 605 and a reservoir seat 618. The reservoir seat 618 is configured to engage, at least temporarily, a portion of the fluid reservoir 630, as described in further detail herein. The distal port 605 is configured to be physically and fluidically coupled to a lock mechanism 621 included in the cannula assembly 620. For example, in some embodiments, the lock mechanism 621 can be a Luer-Lok® configured to receive the port 605. In other embodiments, the port 605 and the lock mechanism 621 can be coupled in any suitable manner such as, for example, a threaded coupling, a friction fit, or the like. In still other embodiments, the port 605 and the lock mechanism 621 can be coupled via an adhesive or the like to fixedly couple the cannula assembly 620 to the housing 601. With the lock mechanism 621 coupled to the port 605, the inner volume 611 of the housing 601 is in fluid communication with a cannula 624 included in the cannula assembly 620, as further described herein.

As described above, the fluid reservoir 630 is disposed within the inner volume 611 of the housing 601. More particularly, the fluid reservoir 630 is movably disposed within the inner volume 611 between a first position in which the fluid reservoir 630 is in a distal position relative to the housing 601 (see e.g., FIG. 28) and a second position in which the fluid reservoir 630 is in a proximal position relative to the housing 601 (see e.g., FIG. 30). As shown in FIG. 26, the fluid reservoir 630 includes a proximal end portion 631 and a distal end portion 632 and defines an inner volume 633 therebetween. The proximal end portion 631 includes a flange 634 and a protrusion 635 and defines a set of openings 636. Furthermore, the proximal end portion 631 of the fluid reservoir 630 is substantially open to receive a portion of the flow control mechanism 640. In this manner, the proximal end portion 631 is configured to engage, interact, or otherwise correspond with a portion of the flow control mechanism 640, as further described herein.

The distal end portion 632 of the fluid reservoir 630 includes a valve seat 637. The valve seat 637 includes a port 638 and receives a valve 639 (see e.g., FIG. 28-30). The valve seat 637 is selectively disposed about the reservoir seat 618 of the housing 601, as described in further detail herein. The valve 639 can be any suitable valve such as, for example, a check valve or the like. In this manner, the distal end portion 632 can be selectively placed in fluid communication with the inner volume 611 when the fluid reservoir 630 is disposed within the housing 601, as described in further detail herein.

As described above, the flow control mechanism 640 can be at least partially disposed within the housing 601. More particularly and as shown in FIG. 27, the flow control mechanism 640 includes an engagement portion 645 configured to be disposed outside the housing 601 and a plunger portion 650 configured to be at least partially disposed within the inner volume 611 defined by the housing 601. As described in further detail herein, the engagement portion 645 can be engaged by a user to move the flow control mechanism 640 between a first configuration and a second configuration.

The plunger portion 650 of the flow control mechanism 640 is configured to extend in a distal direction from a surface of the engagement portion 645. The plunger 650 includes a first surface 652, a second surface 655, a protrusion 653, a first seal member 658, and a second seal member 659. As shown in FIG. 27, the plunger portion 650 is substantially cylindrical and defines a channel 651 that receives, for example, a cannula 664 that defines a lumen 646. More particularly, the cannula 664 is configured to be disposed within an opening 654 defined by the first surface 652 to place the lumen 646 in fluid communication with an inner volume 656 defined between the first surface 652 and the second surface 655. The plunger 650 is further configured to define a set of openings 657 that can selectively place the inner volume 656 in fluid communication with a portion of the housing 601, as described in further detail herein.

Figure 28:
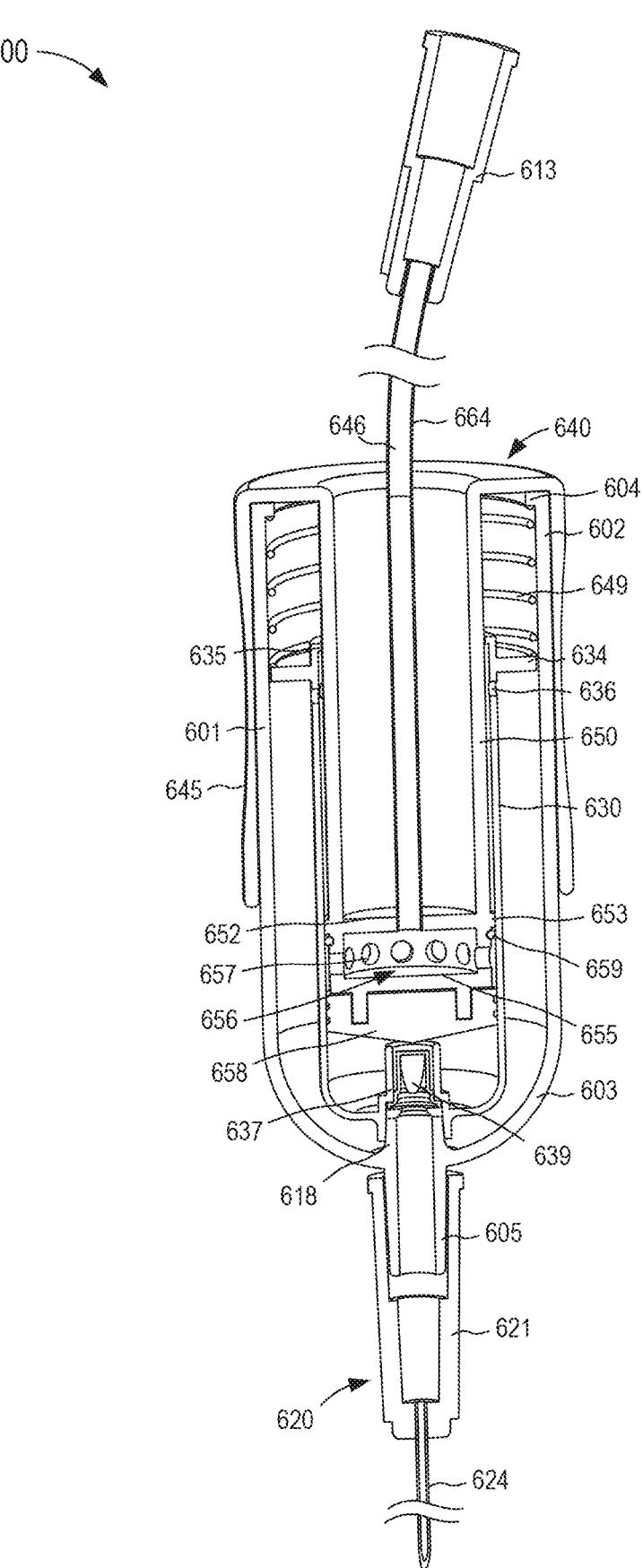
FIGS. 28-30 are cross-sectional views of the fluid transfer device taken along the line $X_6$-$X_6$ in FIG. 24, in a first, second, and third configuration, respectively.
Figure 29:
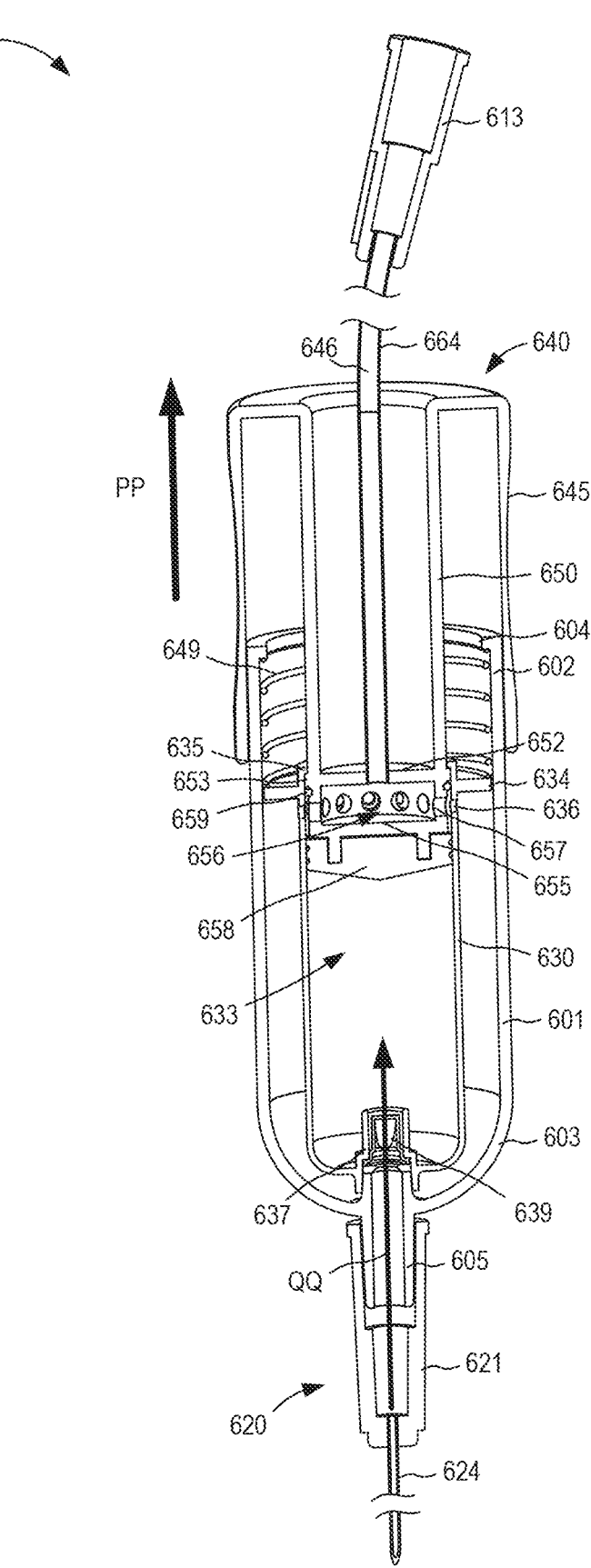
Figure 30:
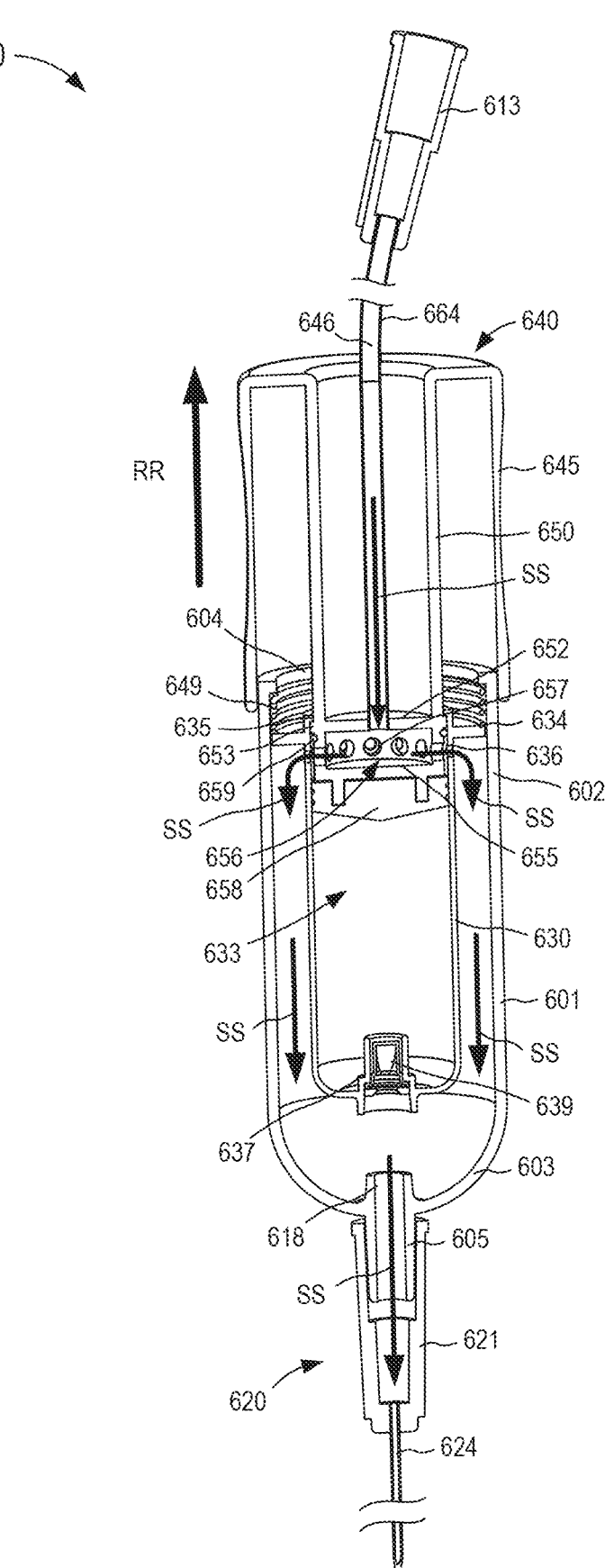

In use, the transfer device 600 can be moved between a first configuration (FIG. 28), a second configuration (FIG. 29), and a third configuration (FIG. 30). Referring to FIG. 28, while in the first configuration, the cannula 624 of the cannula assembly 620 can be inserted into a portion of a patient to place the cannula 624 in fluid communication with, for example, a vein. In some embodiments, the cannula 624 can include a sharp point at a distal end such that the cannula 624 can pierce the portion of the patient. In other embodiments, the cannula assembly 620 can include a trocar (not shown) to facilitate the insertion of the cannula 624. As described above, the cannula assembly 620 is physically and fluidically coupled to the port 605 of the housing 601 such that when the cannula 624 is placed in fluid communication with the vein of the patient, the port 605 is concurrently placed in fluid communication with the vein. With the port 605 in fluid communication with the portion of the patient (e.g., the vein), a user (e.g., a physician, nurse, technician, or the like) can engage the engagement portion 645 of the flow control mechanism 640 to place the transfer device 600 in the second configuration.

As shown in FIG. 29, the transfer device 600 is placed in the second configuration when the plunger portion 650 of the flow control mechanism 640 is moved within the fluid reservoir 630 from a first position (e.g., a distal position) to a proximal position (e.g., a proximal position), as indicated by the arrow PP. More specifically, the transfer device 600 includes a spring 649 configured to engage the protrusion 604 of the housing 601 and the flange 634 of the fluid reservoir 630 to maintain the fluid reservoir 630 in the first position while the flow control mechanism 640 is moved to its second position. Similarly, stated the flow control mechanism 640 is moved in a proximal direction relative to the fluid reservoir 630.

In addition, the first seal member 658 can engage an inner surface of the fluid reservoir 630 such that the proximal movement of the flow control mechanism 640 produces a negative pressure within a portion of the inner volume 633 of the fluid reservoir 630 (e.g., the portion of the inner volume 633 that is disposed distally relative to the first seal member 658). In this manner, the negative pressure introduces a suction force that can be operable placing the valve 639 in an open configuration. Thus, with the cannula 624 and the port 605 in fluid communication with the portion of the patient (e.g., the vein), a flow of bodily fluid (e.g., blood) can pass through the valve 639 and enter the inner volume 633 of the fluid reservoir 630, as indicated by the arrow QQ.

As shown in FIG. 29, the proximal movement of the flow control mechanism 640 relative to the fluid reservoir 630 is configured to stop when the flow control mechanism 640 is in the second position (e.g., the proximal position). More specifically, the protrusion 635 of the fluid reservoir 630 can engage the protrusion 653 of the plunger portion 650 to limit the proximal movement of the flow control mechanism 640 relative to the fluid reservoir 630. Furthermore, when the flow control mechanism 640 is in the second position relative to the fluid reservoir 630, the openings 657 of the plunger portion 650 are in fluid communication with the openings 636 defined by the fluid reservoir 630. Thus, the inner volume 656 defined by the plunger portion 650 of the flow control mechanism 640 is placed in fluid communication with the inner volume 611 of the housing 601, as described in further detail herein.

With the transfer device 600 in the second configuration, a flow of a predetermined amount of bodily fluid can be transferred to the inner volume 633 of the fluid reservoir 630 that can include, for example, dermally residing microbes dislodged during a venipuncture event (e.g., the insertion of the cannula 624 into the vein and/or otherwise accessing the vasculature of the patient). In addition, when the predetermined amount of bodily fluid is transferred to the inner volume 633 of the fluid reservoir 630, the valve 639 can be placed in a closed configuration. For example, in some embodiments, the transfer of the predetermined amount of bodily fluid can be such that the negative pressure within the inner volume 633 is brought into equilibrium with the pressure of the vein, thus allowing the valve 639 to move to the closed configuration. In other embodiments, the valve 639 can be manually actuated by user interference (e.g., engagement of an actuator, a switch, a button, a toggle, or the like). In this manner, the bodily fluid disposed in the inner volume 633 between the first seal member 658 and the distal end portion 632 of the fluid reservoir 630 can be fluidically isolated from a volume outside the inner volume 633. Expanding further, the first seal member 658 prevents a flow of the bodily fluid in the proximal direction and the valve 639, being in the closed configuration, prevents a flow of the bodily fluid in the distal direction. Thus, the predetermined amount of bodily fluid is fluidically isolated from a volume outside the inner volume 633 of the fluid reservoir 630 defined between the first seal member 658 and the distal end portion 632.

As indicated by the arrow RR in FIG. 30, the user can continue to move the flow control mechanism 640 in the proximal direction to place the transfer device 600 in the third configuration. More specifically, with the protrusion 653 of the flow control mechanism 640 in contact with the protrusion 635 of the fluid reservoir 630, the proximal movement of the flow control mechanism 640 is such that the flow control mechanism 640 and the fluid reservoir 630 move, concurrently, in the proximal direction relative to the housing 601. Furthermore, the proximal movement is such that the valve seat 637 is moved in the proximal direction relative to the reservoir seat 618. Similarly stated, the proximal movement of the fluid reservoir 630 is such that the valve seat 637 is no longer disposed about the reservoir seat 618 of the housing 601. In this manner, the port 605 is placed in fluid communication with the inner volume 611 of the housing 601.

With the transfer device 600 in the third configuration, an external fluid source (not shown in FIG. 30) can be placed in fluid communication with a portion of the transfer device 600 to transfer a flow of parenteral fluid to the portion of the patient. For example, in some embodiments, the transfer device 600 can include a proximal lock mechanism 613 that can physically and fluidically couple the transfer device 600 to the external fluid source. The proximal lock mechanism 613 can be any of those described herein. In this manner, the external fluid source can deliver a flow of parenteral fluid to the lumen 646, as indicated by the arrow SS. Moreover, with the lumen 646 in fluid communication with the inner volume 656 defined between the first surface 652 and the second surface 655, the flow of the parenteral fluid can pass through the openings 657 defined by the plunger portion 650 of the flow control mechanism 640. In addition, the first seal member 658 and the second seal member 659 can act to define a fluid flow path that directs the flow of the parenteral fluid to the openings 636 defined by the fluid reservoir 630. In this manner, the flow of parenteral fluid can pass through the openings 636 of the fluid reservoir 630 to enter the inner volume 611 defined by the housing 601. Similarly stated, upon exiting the openings 636, the parenteral fluid can flow within the inner volume 611 defined by the housing 601 and outside of the fluid reservoir 630, as indicated by the arrows SS. Expanding further, the parenteral fluid can flow within the housing 601 in the distal direction and enter the port 605 to transfer the flow parenteral fluid to the cannula assembly 620. Therefore, the external fluid source can deliver a flow of parenteral fluid to the patient that is fluidically isolated from the predetermined amount of bodily fluid disposed in the fluid reservoir 630 and is thus, substantially free from dermally residing microbes and/or other undesirable external contaminants.

In some embodiments, user intervention maintains the transfer device 600 in the third configuration. Expanding further and as described above, the proximal movement of the fluid reservoir 630 is such that a portion of the force applied by the user (e.g., the physician, nurse, technician, or the like) to move the flow control mechanism 640 and fluid reservoir 630 is used to move the spring 649 to a compressed configuration. In such embodiments, the removal of the portion of the force would allow the spring 649 to expand and thereby move the fluid reservoir 630 in the distal direction. In other embodiments, a transfer device can include a catch, protrusion, latch or the like configured to maintain the spring in the compressed configuration.

While the transfer device 600 is shown in FIGS. 24-30 as including a fluid reservoir 630, in other embodiments, a transfer device can include a flow control mechanism with an integrated fluid reservoir. For example, FIGS. 31-34 illustrate a transfer device 700 according to an embodiment. The transfer device 700 includes a housing 701, a cannula assembly 720, and a flow control mechanism 740. In use, the transfer device 700 can be moved between a first configuration and a second configuration to receive a predetermined amount of a bodily fluid from a patient and to deliver a flow of a parenteral fluid to the patient that is substantially free from, for example, dermally residing microbes and/or other undesirable external contaminants.

Figure 31:
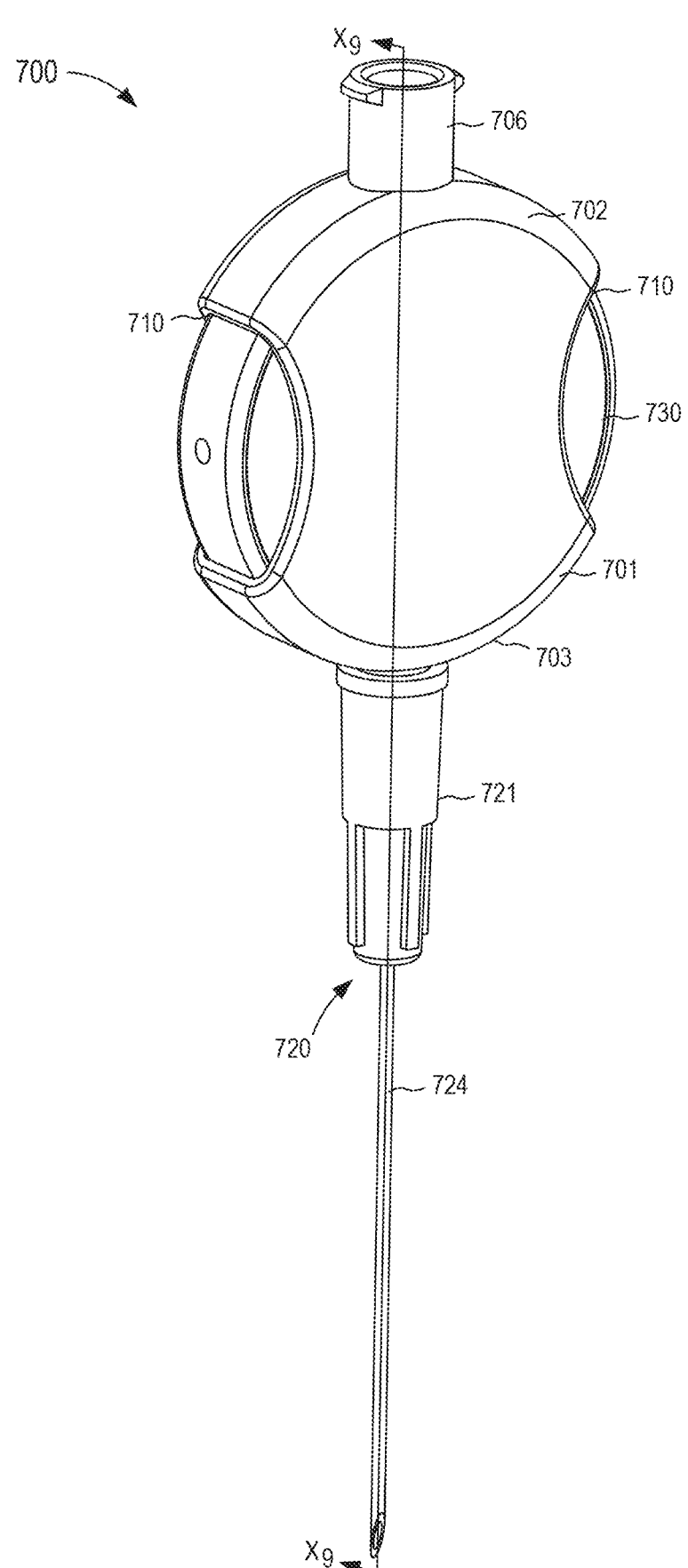
FIG. 31 is a perspective view of a fluid transfer device according to an embodiment.
Figure 32:
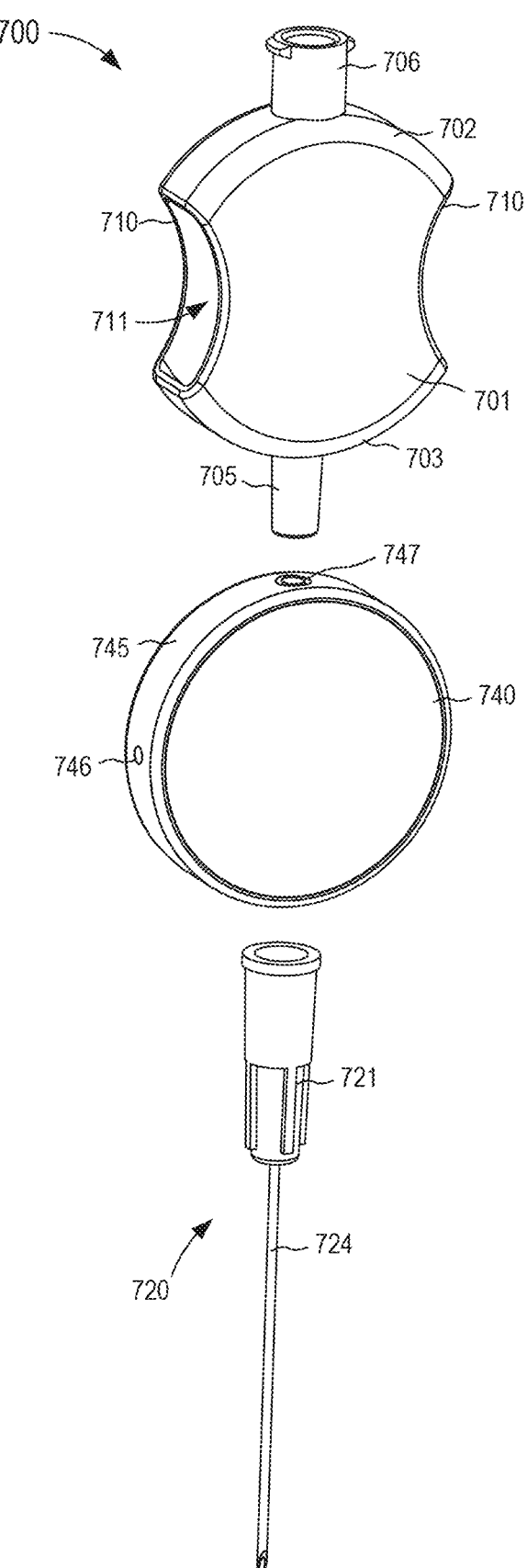
FIG. 32 is an exploded view of the fluid transfer device of FIG. 31.

As shown in FIGS. 31 and 32, the housing 701 includes a proximal end portion 702 having a proximal port 706 and a distal end portion 703 having a distal port 705. The proximal port 706 is configured to be physically and fluidically coupled to an external fluid source, as described in further detail herein. The distal port 705 is configured to be physically and fluidically coupled to a lock mechanism 721 included in the cannula assembly 720. For example, in some embodiments, the lock mechanism 721 can be a Luer-Lok® configured to receive the distal port 705. In other embodiments, the distal port 705 and the lock mechanism 721 can be coupled in any suitable manner such as, for example, a threaded coupling, a friction fit, or the like. In still other embodiments, the distal port 705 and the lock mechanism 721 can be coupled via an adhesive or the like to fixedly couple the cannula assembly 720 to the housing 701. With the lock mechanism 721 coupled to the distal port 705, the distal port 705 is placed in fluid communication with a cannula 724 included in the cannula assembly 720, as further described herein.

The housing 701 defines an inner volume 711 and a set of recess 710. The inner volume 711 is configured to receive at least a portion of the flow control mechanism 740. As shown in FIG. 31, the set of recesses 710 are defined by the housing 701 in a perpendicular orientation relative to the proximal port 706 and distal port 705. Similarly stated, the recesses 710 are perpendicular to a centerline defined by the proximal port 706 and the distal port 705. In this manner, a portion of the flow control mechanism 740 can extend through the recesses 710 when the flow control mechanism 740 is disposed within the inner volume 711 of the housing 701, as described in further detail herein.

Figure 33:
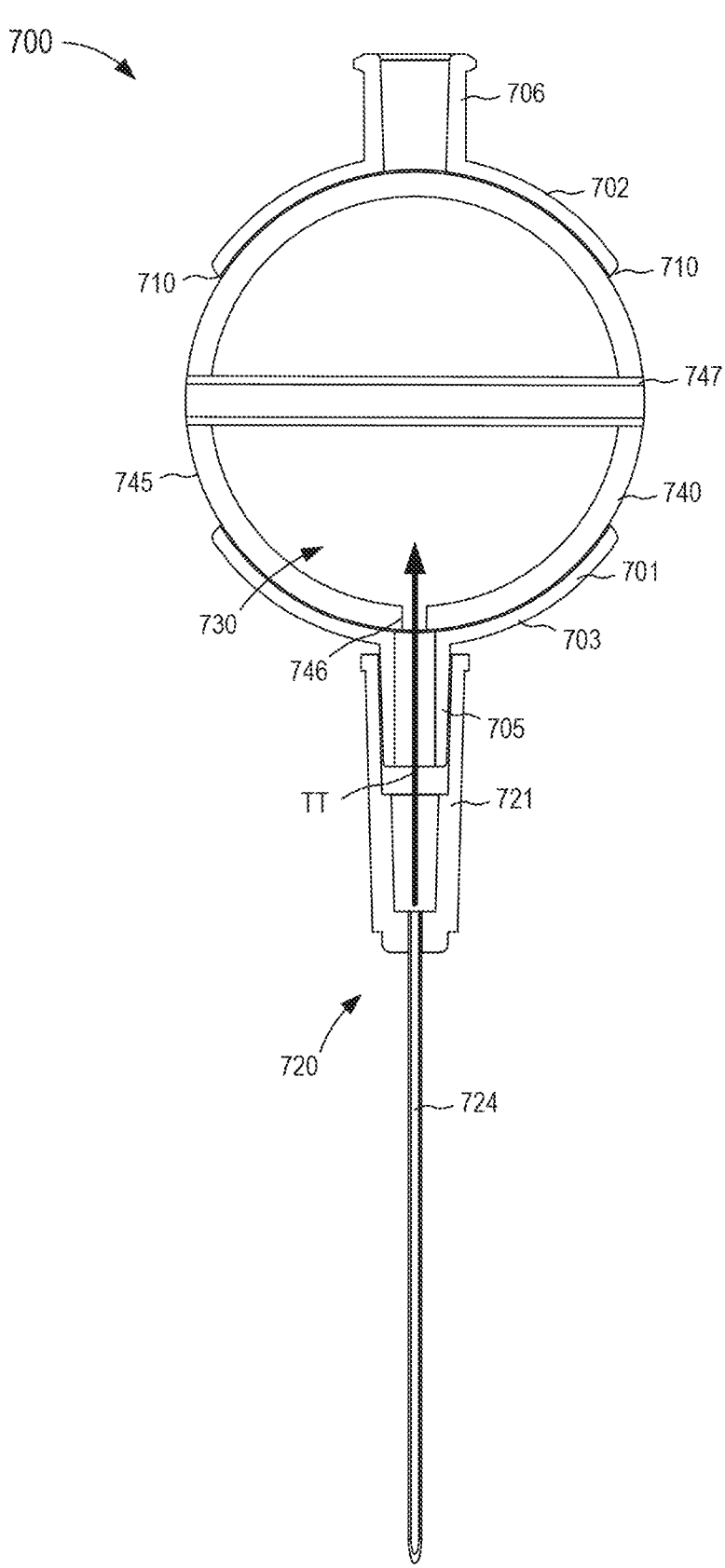
FIGS. 33 and 34 are cross-sectional views of the fluid transfer device taken along the line $X_9$-$X_9$ in FIG. 31, in a first configuration and a second configuration, respectively.

The flow control mechanism 740 defines a first lumen 746, a second lumen 747, and a fluid reservoir 730. The first lumen 746 extends through a portion of the flow control mechanism 740 and is in fluid communication with the fluid reservoir 730. Similarly stated, the first lumen 746 extends through a portion of the flow control mechanism 740 to selectively place the fluid reservoir 730 in fluid communication with a volume substantially outside of the flow control mechanism 740, as described in further detail herein. As shown in FIG. 33, the second lumen 747 extends through the flow control mechanism 740 and is fluidically isolated from the fluid reservoir 730. In this manner, the second lumen 747 can be selectively placed in fluid communication with the proximal port 706 and the distal port 705 of the housing 701 to deliver a flow of parenteral fluid, as described in further detail herein.

The flow control mechanism 740 has a circular cross-sectional shape such that when the flow control mechanism 740 is disposed within the inner volume 711, a portion of the flow control mechanism 740 forms a friction fit with the walls of the housing 701 defining the inner volume 711. For example, in some embodiments, the flow control mechanism 740 is formed from silicone and has a diameter larger than the diameter of the inner volume 711. In this manner, the diameter of the flow control mechanism 740 is reduced when the flow control mechanism 740 is disposed within the inner volume 711. Thus, the outer surface of the flow control mechanism 740 forms a friction fit with the inner surface of the walls defining the inner volume 711. In other embodiments, the flow control mechanism 740 can be any suitable elastomer configured to deform when disposed within the inner volume 711 of the housing 701.

In use, while in the first configuration, the cannula 724 of the cannula assembly 720 can be inserted into a portion of a patient to place the cannula 724 in fluid communication with, for example, a vein. In some embodiments, the cannula 724 can include a sharp point at a distal end such that the cannula 724 can pierce the portion of the patient. In other embodiments, the cannula assembly 720 can include a trocar (not shown) to facilitate the insertion of the cannula 724. As described above, the cannula assembly 720 is physically and fluidically coupled to the distal port 705 of the housing 701 such that when the cannula 724 is placed in fluid communication with the vein of the patient, the distal port 705 is placed in fluid communication with the vein.

As shown in FIG. 33, when the transfer device 700 is in the first configuration, the first lumen 746 of the flow control mechanism 740 is in fluid communication with the distal port 705 of the housing 701. In this manner, the fluid reservoir 730 defined by the flow control mechanism 740 is placed in fluid communication with the vein of the patient and can receive a flow of a bodily fluid (e.g., blood). Moreover, with the flow control mechanism 740 forming a friction fit with the inner surface of the housing 701 (as described above), the flow control mechanism 740 and the housing 701 can form a substantially fluid tight seal about an inlet of the first lumen 746. In this manner, the cannula assembly 720, the distal port 705, and the first lumen 746 collectively define a flow path configured to deliver a flow of bodily fluid from the portion of the patient to the fluid reservoir 730, as indicated by the arrow TT. In addition, the flow of bodily fluid can be such that dermally residing microbes dislodged during a venipuncture event (e.g., the insertion of the cannula 724) are entrained in the flow of bodily fluid and are transferred to the fluid reservoir 740.

With a desired amount of bodily fluid transferred to the fluid reservoir 730, a user can engage the transfer device 700 to move the transfer device 700 from the first configuration to the second configuration. In some embodiments, the desired amount of bodily fluid transferred to the fluid reservoir 730 is a predetermined amount of fluid. For example, in some embodiments, the transfer device 700 can be configured to transfer bodily fluid until the pressure within the fluid reservoir 730 is equilibrium with the pressure of the portion of the body in which the cannula 724 is disposed (e.g., the vein). In some embodiments, at least a portion of the flow control mechanism 740 can be transparent to allow visualization of the bodily fluid flowing into the fluid reservoir 730. The flow control mechanism 740 can include indicators (e.g., 0.1 mL, 0.5 mL, 1 mL, 1.5 mL, 2 mL, 3 mL, 4 mL, 5 mL, etc. graduation marks) to the user can visualize the volume of bodily fluid that has been received in the fluid reservoir 730.

Figure 34:
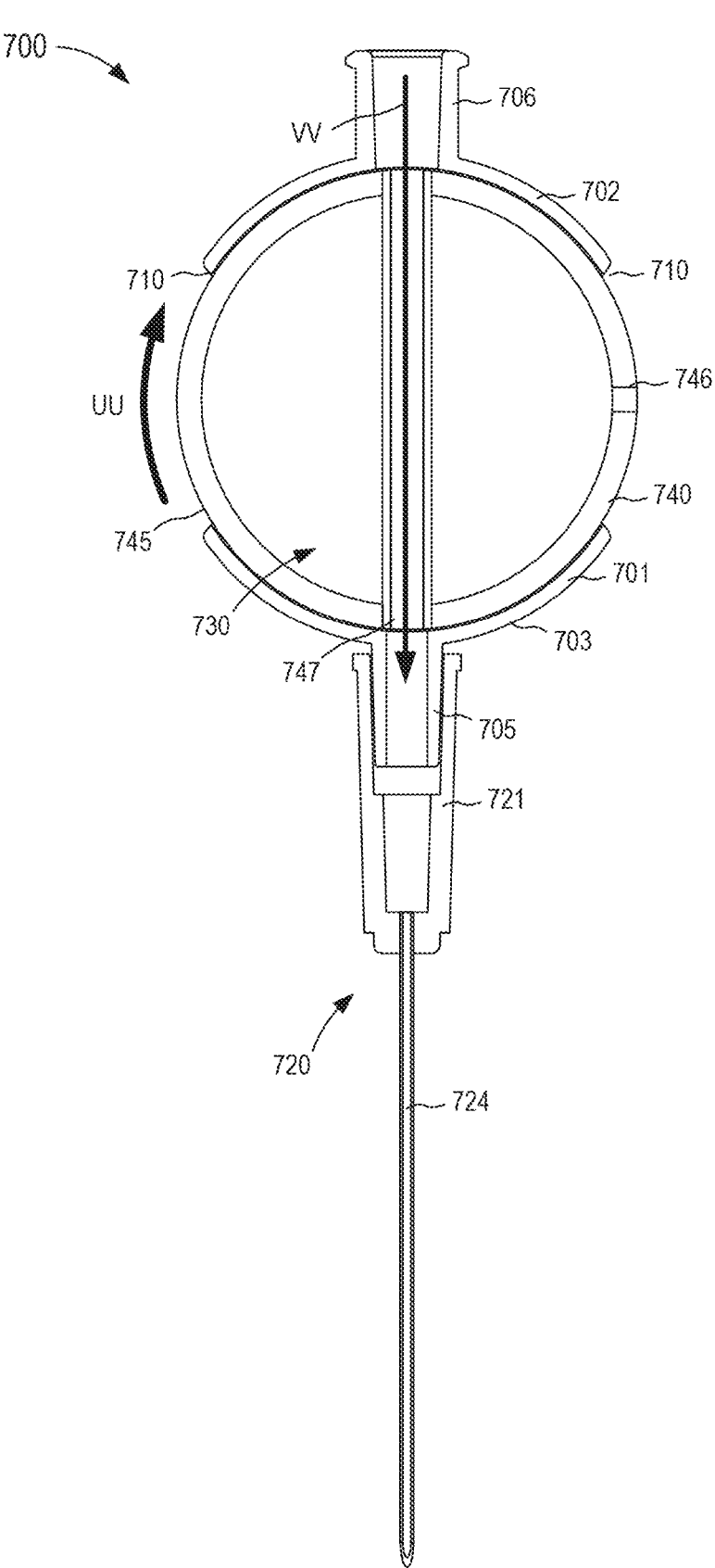

As shown in FIG. 34, the transfer device 700 can be moved from the first configuration to the second configuration by moving the flow control mechanism 740 in the direction of the arrow UU. In this manner, the first lumen 746 is fluidically isolated from the distal port 705. While not shown in FIGS. 31-34, the first lumen 746 can include a valve or seal configured to fluidically isolate the bodily fluid disposed within the fluid reservoir 730 from a volume outside the flow control mechanism 740. In some embodiments, the valve can be, for example, a one-way check valve. Thus, the fluid reservoir 730 can receive the flow of fluid from a volume outside the fluid reservoir 730 but prevent a flow of fluid from the fluid reservoir 730.

When moved to the second configuration, the second lumen 747 defined by the flow control mechanism 740 is placed in fluid communication with the distal port 705 and the proximal port 706 of the housing 701. As described above, the proximal port 706 can be physically and fluidically coupled to an external fluid source (not shown in FIGS. 31-34) such that when the transfer device 700 is in the second configuration, the proximal port 706, the second lumen 747, the distal port 705, and the cannula assembly 720 collectively define a fluid flow path. In this manner, the transfer device 700 can facilitate the delivery of a flow of parenteral fluid from the external fluid source to the portion of the patient (e.g., the vein), as indicated by the arrow VV in FIG. 34. Expanding further, with the predetermined amount of bodily fluid fluidically isolated within the fluid reservoir 730, the transfer device 700 can facilitate the delivery of the flow of parenteral fluid to the patient that is substantially free from, for example, the dermally residing microbes dislodged during the venipuncture event.

Figure 35:
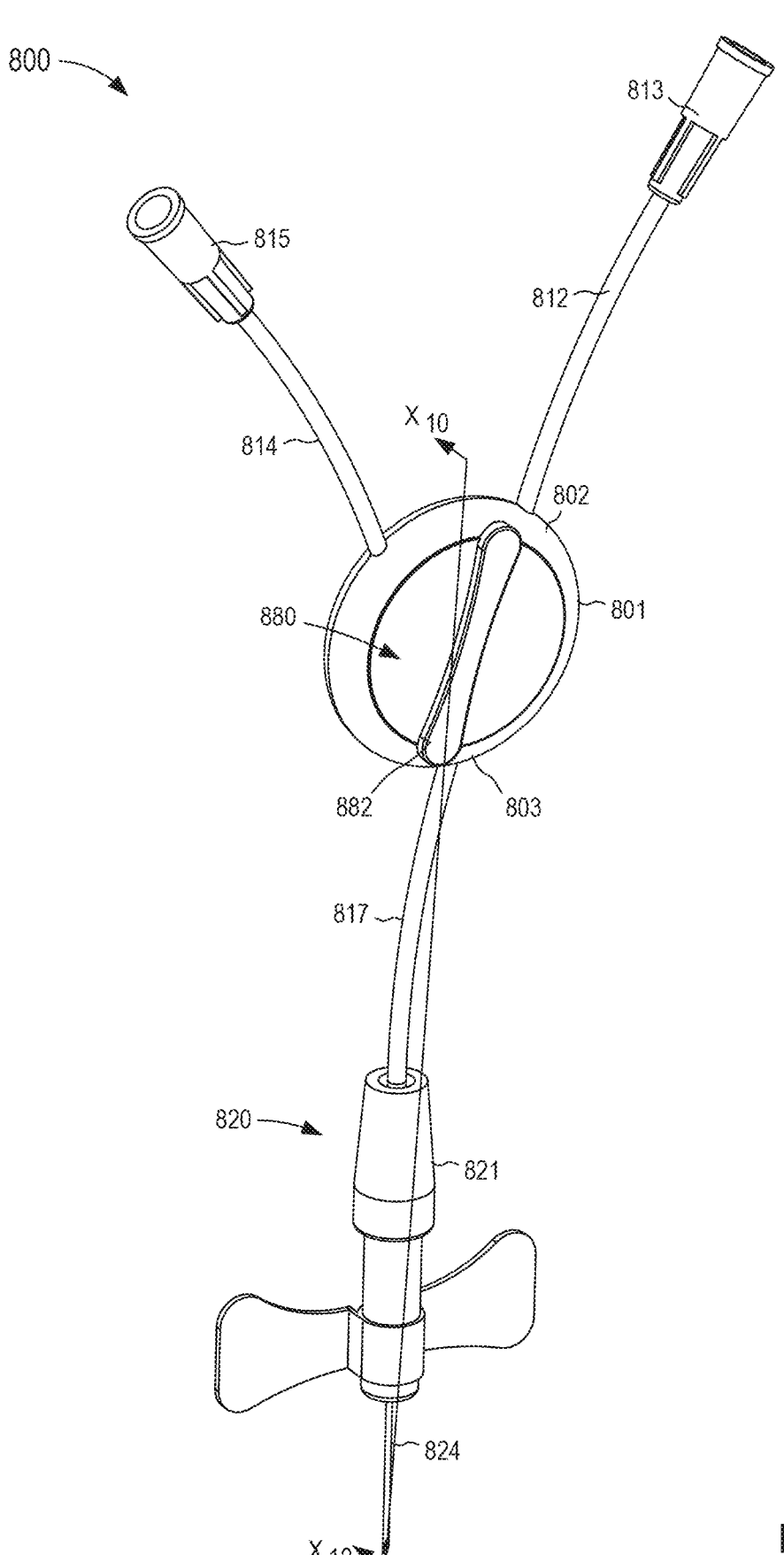
FIG. 35 is a perspective view of a fluid transfer device according to an embodiment.
Figure 36:
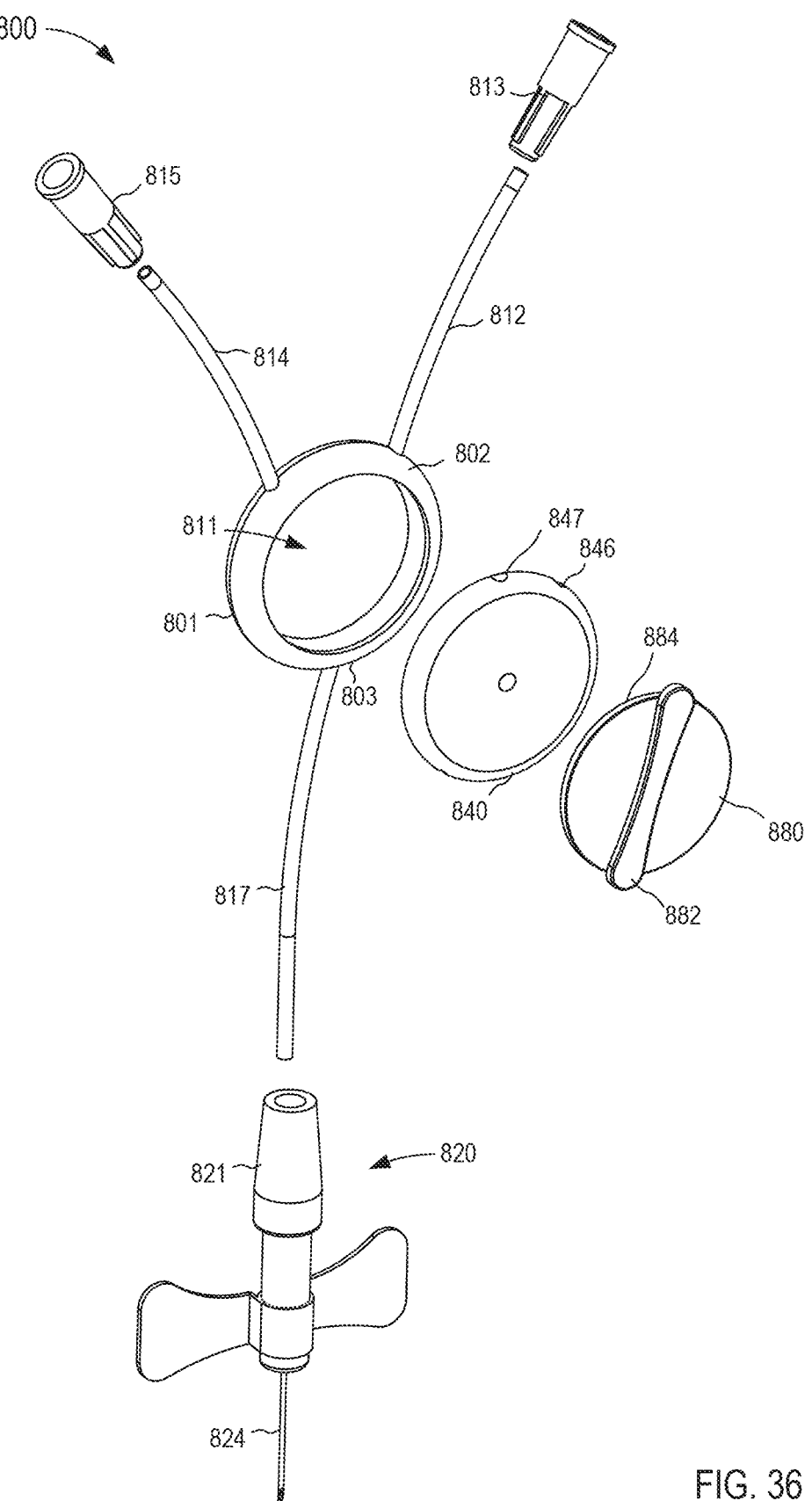
FIG. 36 is an exploded view of the fluid transfer device of FIG. 35.

While the flow control mechanism 740 is shown in FIGS. 31-34 as including the integrated fluid reservoir 730, in other embodiments, a transfer device can be configured to be physically and fluidically coupled to an external fluid reservoir. For example, FIGS. 35-39 illustrate a transfer device 800 according to an embodiment. As shown in FIGS. 35 and 36, the transfer device 800 includes a housing 801, a cannula assembly 820, and a flow control mechanism 880. In use, the transfer device 800 can be moved between a first configuration and a second configuration to receive a predetermined amount of a bodily fluid from a patient and to deliver a flow of a parenteral fluid to the patient that is substantially free from, for example, dermally residing microbes.

Figure 37:
FIG. 37 is a cross-sectional view of the fluid transfer device taken along the line $X_{10}$-$X_{10}$ in FIG. 35, in a first configuration.

The housing 801 includes a proximal end portion 802, a distal end portion 803, and defines an inner volume 811. The inner volume 811 can receive at least a portion of the flow control mechanism 880 and the actuator 880, as further described herein. As shown in FIG. 37, the distal end portion 803 of the housing 801 defines a distal port 805 and the proximal end portion 802 of the housing 801 defines a first proximal port 806, and a second proximal port 807. The distal port 805, the first proximal port 806, and the second proximal port 807 are configured to be in fluid communication with the inner volume 811 defined by the housing 801.

The distal port 805 is configured to receive a distal cannula 817. The distal cannula 817 (e.g., a lumen defining cannula) is configured to be physically and fluidically coupled to a port 822 included in the cannula assembly 820. The port 822 can be any suitable port. For example, in some embodiments, the distal cannula 817 and the port 822 can be coupled via an adhesive or the like to fixedly couple the cannula assembly 820 to the housing 801. With the port 822 of the cannula assembly 820 coupled to the distal cannula 817 and with the distal cannula 817 coupled to the distal port 805, the distal port 805 is in fluid communication with a cannula 824 included in the cannula assembly 820, as further described herein.

The first proximal port 806 and the second proximal port 807 are configured to receive a first proximal cannula 812 and a second proximal cannula 814, respectively (e.g., lumen defining cannulas). Furthermore, the first proximal cannula 812 is physically and fluidically coupled to a first lock mechanism 813 that can further be physically and fluidically coupled to an external fluid reservoir (not shown in FIGS. 35-39). Similarly, the second proximal cannula 814 is physically and fluidically coupled to a second lock mechanism 815 that can further be physically and fluidically coupled to an external fluid source (not shown in FIGS. 35-39). In this manner, the cannula assembly 820, the external fluid reservoir (not shown), and the external fluid source (not shown) can be selectively placed in fluid communication with the inner volume 811 defined by the housing 801, as described in further detail herein.

Referring back to FIG. 36, the actuator mechanism 880 includes an engagement portion 882 and an activation surface 884. The activation surface 844 is configured to contact, mate, or otherwise engage the flow control mechanism 840. The engagement portion 882 can be engaged by a user to rotate the actuator mechanism 880 relative to the housing 801 to move the transfer device 800 between a first configuration and a second configuration, as described in further detail herein.

The flow control mechanism 840 defines a first lumen 846 and a second lumen 847 and is disposed within the inner volume 821 defined by the housing 801. The flow control mechanism 840 defines a circular cross-sectional shape such that when the flow control mechanism 840 is disposed within the inner volume 821, a portion of the flow control mechanism 840 forms a friction fit with the walls of the housing 801 defining the inner volume 821, as described in detail above. The flow control mechanism 840 is operably coupled to and/or otherwise engages the actuator 880. For example, in some embodiments, the actuator mechanism 880 can be coupled to the flow control mechanism 840 via a mechanical fastener and/or adhesive. In other embodiments, the actuator mechanism 880 and the flow control mechanism 840 can be coupled in any suitable manner. Therefore, the flow control mechanism 840 is configured to move concurrently with the actuator mechanism 880 when the actuator mechanism 880 is rotated relative to the housing 801. In this manner, the flow control mechanism 840 can be moved to place the first lumen 846 or the second lumen 847 in fluid communication with the distal port 805, the first proximal port 806, and/or the second proximal port 807, as described in further detail herein.

In use, while in the first configuration, the cannula 824 of the cannula assembly 820 can be inserted into a portion of a patient to place the cannula 824 in fluid communication with, for example, a vein. In some embodiments, the cannula 824 can include a sharp point at a distal end such that the cannula 824 can pierce the portion of the patient. In other embodiments, the cannula assembly 820 can include a trocar (not shown) to facilitate the insertion of the cannula 824. As described above, the cannula assembly 820 is physically and fluidically coupled to the distal port 805 of the housing 801 such that when the cannula 824 is placed in fluid communication with the vein of the patient, the distal port 805 is placed in fluid communication with the vein.

Furthermore, a user (e.g., a physician, a nurse, a technician, or the like) can engage the transfer device 800 to physically and fluidically couple the first lock mechanism 813 to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC. In this manner, the external fluid reservoir can define a negative pressure within an inner volume of the reservoir. Therefore, when the flow control mechanism 840 is in the first configuration, a negative pressure differential introduces a suction force within the first proximal cannula 812, the first lumen 846 defined by the flow control mechanism 840, the distal cannula 817, and the cannula assembly 820. In this manner, the first proximal cannula 812, the first lumen 846 defined by the flow control mechanism 840, the distal cannula 817, and the cannula assembly 820 collectively define a fluid flow path configured to transfer a flow of a bodily fluid to the external fluid reservoir, as indicated by the arrow WW in FIG. 37. In addition, the flow of bodily fluid can be such that dermally residing microbes dislodged during a venipuncture event (e.g., the insertion of the cannula 824) are entrained in the flow of bodily fluid and are transferred to the external fluid reservoir.

Figure 38:
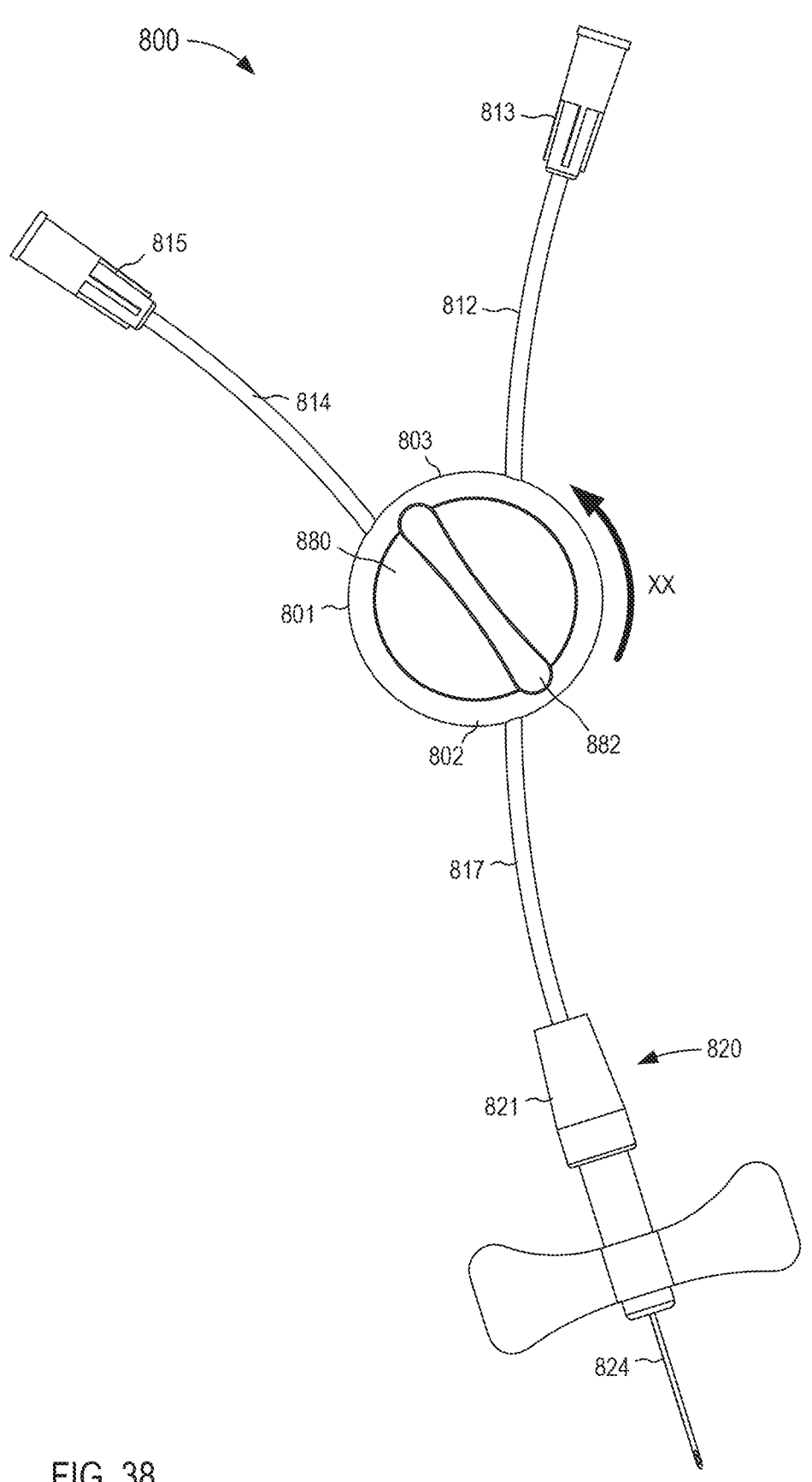
FIG. 38 is a front view of the fluid transfer device of FIG. 35 in a second configuration.

As shown in FIG. 38, in some embodiments, the magnitude of the suction force can be modulated by moving the actuator mechanism 880 in the direction of the arrow XX. For example, in some instances, it can be desirable to limit the amount of suction force introduced to a vein. In such instances, the user can move the actuator mechanism 880 and the flow control mechanism 840 to reduce the size of the fluid pathway (e.g., an inner diameter) between the distal port 805 of the housing 801 and the first lumen 846 of the flow control mechanism 840, thereby reducing the suction force introduced into the vein of the patient.

With the desired amount of bodily fluid transferred to the external fluid reservoir, a user can engage the actuator mechanism 880 to move the transfer device 800 from the first configuration to the second configuration. In some embodiments, the desired amount of bodily fluid transferred to the external fluid reservoir is a predetermined amount of fluid. For example, in some embodiments, the transfer device 800 can be configured to transfer bodily fluid until the pressure within the external fluid reservoir is equilibrium with the pressure of the portion of the body in which the lumen-defining device is disposed (e.g., the vein), as described above. In some embodiments, at least a portion of the external fluid reservoir can be transparent to allow visualization of the bodily fluid flowing into the fluid reservoir. The external fluid reservoir can include indicators (e.g., 0.1 mL, 0.5 mL, 1 mL, 1.5 mL, 2 mL, 3 mL, 4 mL, 5 mL, etc. graduation marks to accommodate identification of diversion volumes ranging from just a few drops or centiliters of blood to a larger volumes) so the user can visualize the volume of bodily fluid that has been received in the external fluid reservoir.

Figure 39:
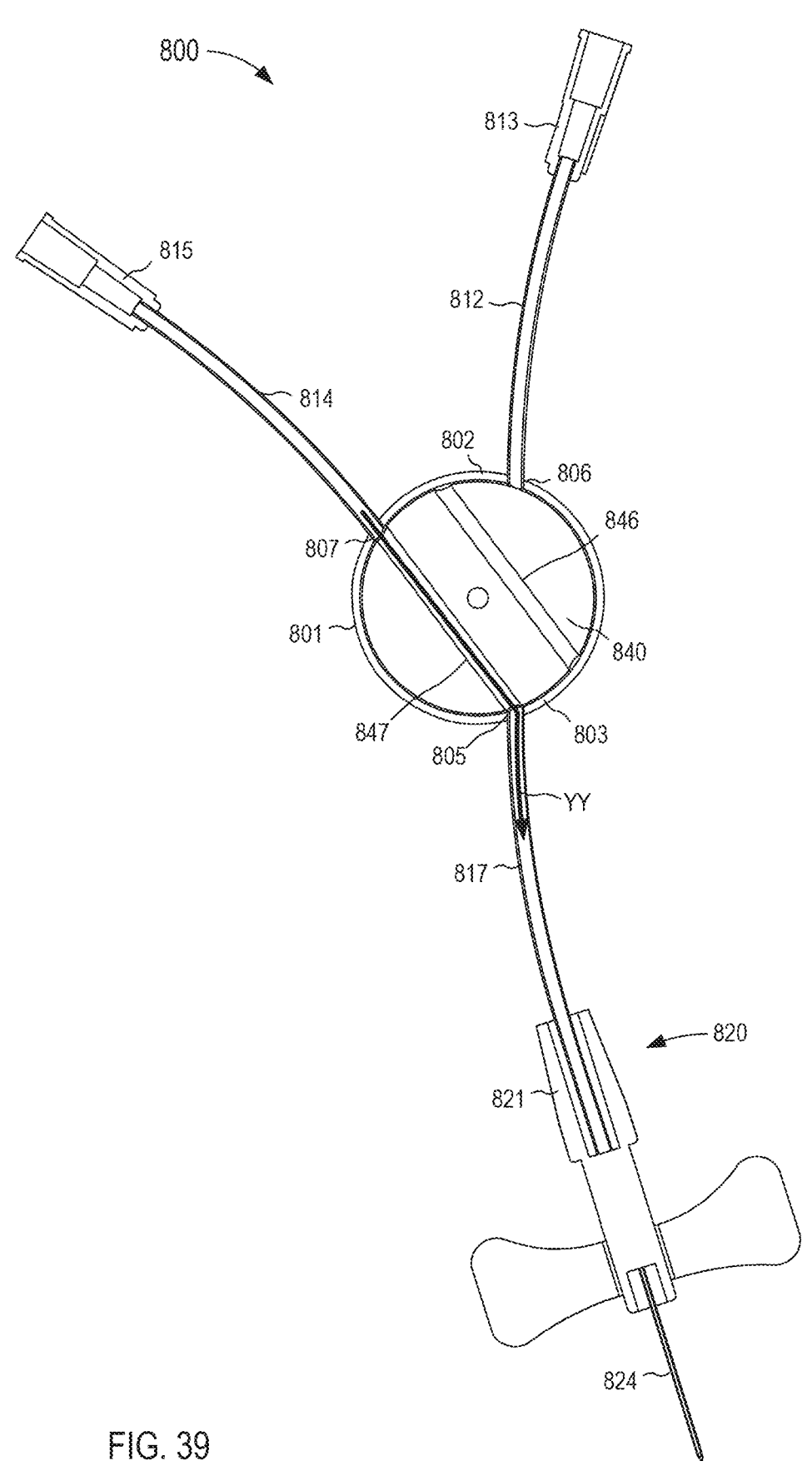
FIG. 39 is a cross-sectional view of the fluid transfer device taken along the line $X_{10}$-$X_{10}$ in FIG. 35, in the second configuration.

The transfer device 800 can be moved from the first configuration to the second configuration by further moving the actuator mechanism 880 in the direction of the arrow XX in FIG. 38. As the actuator mechanism 880 is moved from the first configuration toward the second configuration, the actuator mechanism 880 rotates the flow control mechanism 840 toward its second configuration. In this manner, the first lumen 846 is fluidically isolated from the distal port 805 and the first proximal port 806 and the external fluid reservoir can be physically and fluidically decoupled from the transfer device 800. In addition, the second lumen 847 defined by the flow control mechanism 840 is placed in fluid communication with the distal port 805 and the second proximal port 807, as shown in FIG. 39.

With the transfer device in the second configuration, the second proximal lock mechanism 815 can be physically and fluidically coupled to the external fluid source (not shown in FIGS. 35-39). In this manner, the second proximal cannula 814, the second lumen 847 of the flow control mechanism 840, the distal cannula 817, and the cannula assembly 820 collectively define a fluid flow path. Thus, the transfer device 800 can facilitate the delivery of a flow of parenteral fluid from the external fluid source to the portion of the patient (e.g., the vein), as indicated by the arrow YY in FIG. 39. Expanding further, with the predetermined amount of bodily fluid transfer to the external fluid reservoir and with the external fluid reservoir decoupled from the transfer device 800, the transfer device 800 can facilitate the delivery of the flow of parenteral fluid to the patient that is substantially free from, for example, the dermally residing microbes dislodged during the venipuncture event or otherwise introduced to the fluid flow path to the patient.

FIG. 40 is a flowchart illustrating a method 990 of delivering a fluid to a patient using a fluid transfer device, according to an embodiment. The method 990 includes establishing fluid communication between the patient and the fluid transfer device, at 991. The fluid transfer device can be any of those described herein. As such, the fluid transfer device can include a cannula assembly or the like that can be inserted percutaneously to place the fluid transfer device in fluid communication with the patient (e.g., inserted into a vein of the patient). More specifically, in some embodiments, the cannula assembly of the fluid transfer device can include a sharpened distal end configured to pierce the skin of the patient. In other embodiments, the transfer device can include a flow control mechanism that can include a sharpened distal end portion that is configured to extend beyond a distal end portion of the cannula assembly to pierce the skin of the patient. For example, in some embodiments, the fluid transfer device can include a flow control mechanism that is substantially similar to the flow control mechanism 340 of the transfer device 300 described above with reference to FIGS. 4-10.

With the cannula assembly in fluid communication with the patient, a predetermined volume of a bodily fluid is withdrawn from the patient, at 991. For example, in some embodiments, the fluid transfer device can include a flow control mechanism, such as those described above, that can be moved between a first configuration and a second configuration. In some embodiments, flow control mechanism can be configured to define a fluid flow path between, for example, the cannula assembly and a fluid reservoir included in and/or fluidically coupled to the fluid transfer device. In other embodiments, any portion of fluid transfer device can define at least a portion of the fluid flow path. For example, the fluid transfer device can include a housing or the like that can define at least a portion of the fluid flow path. Thus, the predetermined volume of the bodily fluid is transferred to the fluid reservoir, at 993. In some embodiments, the predetermined volume of the bodily fluid can include, for example, dermally residing microbes that were dislodged during, for example, the venipuncture event (e.g., inserting the cannula assembly into the patient).

Once the predetermined volume of bodily fluid is disposed in the fluid reservoir, the fluid transfer device is fluidically isolated from the fluid reservoir to sequester the predetermined volume of bodily fluid in the fluid reservoir, at 994. For example, in some embodiments, once the predetermined volume of bodily fluid is disposed in the fluid reservoir, the fluid transfer device can be physically and/or fluidically decoupled from the fluid reservoir. In other embodiments, the flow control mechanism (as described above) can be moved from the first configuration to the second configuration to fluidically isolate the fluid reservoir from a volume outside of the fluid reservoir. For example, in some embodiments, the flow control mechanism can define a lumen or the like that can define a fluid flow path between the cannula assembly and the fluid reservoir when in the first configuration. In such embodiments, the flow control mechanism can be transitioned (e.g., moved, rotated, and/or otherwise reconfigured) from the first configuration to the second configuration in which the lumen is removed from fluid communication with the cannula assembly and/or the fluid reservoir, thereby fluidically isolating the fluid reservoir from the cannula assembly. In some embodiments, the flow control mechanism can be configured to transition from the first configuration to the second configuration automatically once the predetermined volume of bodily fluid is disposed in the fluid reservoir.

With the fluid reservoir fluidically isolated from at least a portion of the fluid transfer device, fluid communication is established between the patient and a fluid source via the fluid transfer device, at 995. For example, in some embodiments, the fluid source can be operably coupled to the fluid transfer device to place the fluid source in fluid communication with at least a portion of the fluid transfer device. In some embodiments, the flow control mechanism (described above) can define a second lumen that can place the fluid source in fluid communication with the cannula assembly when in the second configuration. In other embodiments, with the fluid reservoir decoupled from the fluid transfer device that fluid source can be placed in fluid communication with the cannula assembly via any other portion of the fluid transfer device (e.g., a portion of a housing and/or the like). In this manner, a fluid can flow from the fluid source, through the fluid transfer device and into the patient. Moreover, by fluidically isolating the predetermined volume of bodily fluid the flow of fluid from the fluid source can be substantially free of contaminants such as, for example, the dermally residing microbes, as described above.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Additionally, certain steps may be partially completed before proceeding to subsequent steps.

While various embodiments have been particularly shown and described, various changes in form and details may be made. For example, while the actuator 580 is shown and described with respect to FIG. 21 as being rotated in a single direction, in other embodiments, an actuator can be rotated in a first direction (e.g., in the direction of the arrow MM in FIG. 21) and a second direction, opposite the first. In such embodiments, the rotation in the second direction can be configured to move a transfer device through any number of configurations. In other embodiments, the rotation of the actuator in the second direction can be limited.

Although various embodiments have been described as having particular features and/or combinations of components, other embodiments are possible having any combination or sub-combination of any features and/or components from any of the embodiments described herein.

The specific configurations of the various components can also be varied. For example, the size and specific shape of the various components can be different from the embodiments shown, while still providing the functions as described herein. More specifically, the size and shape of the various components can be specifically selected for a desired rate of bodily fluid flow into a fluid reservoir or for a desired rate of parenteral fluid flow into the patient.

The invention claimed is:

1. A device, comprising:
a first port configured to be placed in fluid communication with a patient;
a second port;
a seal;
a channel;
a valve in communication with the channel;
a sequestration chamber between the channel and the seal, the seal configured to facilitate a suction force in the sequestration chamber to draw, when the valve is in a first position, at least a portion of a first volume of fluid to the seal, the sequestration chamber configured to contain the first volume of fluid therein; and
a housing that houses the seal, the valve, the sequestration chamber, and at least a portion of the channel, the housing defining an inner volume that forms at least a portion of a fluid flow path separate from the sequestration chamber, the fluid flow path configured to receive, when the valve is in a second position, a second volume of fluid that bypasses the sequestration chamber and the first volume of fluid contained therein.

2. The device of claim 1, wherein the first volume of fluid is an initial volume of blood received from the patient after venipuncture.

3. The device of claim 2, wherein the initial volume of blood received from the patient after venipuncture includes dermally residing contaminants, and the second volume of fluid is substantially free of dermally residing contaminants.

4. The device of claim 1, wherein the seal and the valve are disposed in the housing and configured such that the suction force draws at least the portion of the first volume of fluid past the valve and to the seal when the valve is in the first position.

5. The device of claim 1, wherein the first volume of fluid is prevented from flowing into the fluid flow path when the valve is in the first position.

6. The device of claim 1, wherein the first port and the second port define at least a portion of the fluid flow path.

7. The device of claim 1, wherein the seal is configured to transition between a first state and a second state, the seal configured to cause the suction force in the channel to draw at least the portion of the first volume of fluid to the seal prior to the seal being in the second state.

8. The device of claim 7, wherein the seal being in the second state causes an equalization of pressure between at least a portion of the channel and a portion of the patient.

9. The device of claim 7, wherein the valve is configured to transition to the second position after the seal is in the second state.

10. The device of claim 1, wherein the housing includes the first port.

11. A device, comprising:
a first port configured to be placed in fluid communication with a patient;
a second port;
a valve movable between a first position and a second position;
a sequestration chamber in communication with the first port;
a seal in communication with the sequestration chamber, the seal configured to facilitate a suction force in the sequestration chamber to draw, when the valve is in the first position, at least a portion of a first volume of fluid through a first fluid flow path and to the seal, the sequestration chamber configured to contain the first volume of fluid therein; and
a housing that defines an inner volume, the inner volume forming at least a portion of a second fluid flow path separate from the sequestration chamber, the second fluid flow path configured to receive, when the valve is in the second position, a second volume of fluid that flows past the sequestration chamber and the first volume of fluid contained therein.

12. The device of claim 11, wherein the first volume of fluid is an initial volume of blood received from the patient after venipuncture.

13. The device of claim 12, wherein the initial volume of blood received from the patient after venipuncture includes dermally residing contaminants, and the second volume of fluid is substantially free of dermally residing contaminants.

14. The device of claim 11, wherein the seal and the valve are disposed in the housing and configured such that the suction force draws at least the portion of the first volume of fluid past the valve and to the seal when the valve is in the first position.

15. The device of claim 11, wherein the first volume of fluid is prevented from flowing into the second fluid flow path when the valve is in the first position.

16. The device of claim 11, wherein the valve is closer to the first port when the valve is in the first position than when the valve is in the second position.

17. The device of claim 11, wherein the first port and the second port define at least a portion of the second fluid flow path.

18. The device of claim 11, wherein the seal is configured to transition between a first state and a second state, the seal configured to cause the suction force in the sequestration chamber to draw the first volume of fluid toward the seal prior to the seal being in the second state.

19. The device of claim 18, wherein the seal being in the second state causes an equalization of pressure between at least a portion of the sequestration chamber and a portion of the patient.

20. The device of claim 18, wherein the valve is configured to transition to a second position when the seal is in the second state.

21. A device, comprising:
a first port configured to be placed in fluid communication with a patient;
a second port;
a valve;
a sequestration chamber in communication with the first port;
a seal configured to facilitate formation of a suction force within the sequestration chamber, the suction force operable to draw, when the valve is in a first position, at least a portion of a first volume of fluid from the first port to the seal, the sequestration chamber configured to contain the first volume of fluid therein; and
a housing defining an inner volume that forms at least a portion of a fluid flow path separate from the sequestration chamber, the fluid flow path configured to receive, when the valve is in a second position, a second volume of fluid that flows past the sequestration chamber and the first volume of fluid contained therein.

22. The device of claim 21, wherein the first volume of fluid is an initial volume of blood received from the patient after venipuncture.

23. The device of claim 22, wherein the first volume of fluid includes dermally residing contaminants, and the second volume of fluid is substantially free of dermally residing contaminants.

24. The device of claim 21, wherein the seal and the valve are disposed in the housing, the valve being at least partially disposed in the fluid flow path in a position between the first port and the seal.

25. The device of claim 21, wherein the seal and the valve are disposed in the housing, the seal and the valve are configured such that the suction force draws at least the portion of the first volume of fluid past the valve and to the seal when the valve is in the first position.

26. The device of claim 21, wherein the first volume of fluid is substantially prevented from flowing from the first port and into the fluid flow path when the valve is in the first position.

27. The device of claim 21, wherein the valve is closer to the first port when the valve is in the first position than when the valve is in the second position.

28. The device of claim 21, wherein the first port and the second port define at least a portion of the fluid flow path.

29. The device of claim 21, wherein the seal is configured to transition between a first state and a second state, the seal configured to facilitate formation of the suction force in the sequestration chamber to draw the first volume of fluid to the seal prior to the seal being in the second state.

30. The device of claim 29, wherein the seal being in the second state causes an equalization of pressure between at least a portion of the sequestration chamber and a portion of the patient.

* * * * *